US009315770B2

(12) United States Patent
Ellis et al.

(10) Patent No.: US 9,315,770 B2
(45) Date of Patent: *Apr. 19, 2016

(54) BACTERIAL HOST STRAIN

(71) Applicant: UCB PHARMA, S.A., Brussels (BE)

(72) Inventors: Mark Ellis, Slough (GB); David Paul Humphreys, Slough (GB)

(73) Assignee: UCB PHARMA, S.A., Brussels (BG)

( * ) Notice: Subject to any disclaimer, the term of this patent is extended or adjusted under 35 U.S.C. 154(b) by 0 days.

This patent is subject to a terminal disclaimer.

(21) Appl. No.: 14/827,408

(22) Filed: Aug. 17, 2015

(65) Prior Publication Data

US 2015/0344840 A1 Dec. 3, 2015

Related U.S. Application Data

(63) Continuation of application No. 13/497,987, filed as application No. PCT/GB2010/001790 on Sep. 23, 2010, now Pat. No. 9,109,216.

(30) Foreign Application Priority Data

Sep. 24, 2009 (GB) .................................. 0916821.2
Sep. 24, 2009 (GB) .................................. 0916822.0

(51) Int. Cl.
C12N 1/21 (2006.01)
C12N 1/20 (2006.01)
C12R 1/19 (2006.01)
C07K 16/24 (2006.01)
C12N 9/52 (2006.01)
C12N 15/70 (2006.01)
C12P 21/02 (2006.01)

(52) U.S. Cl.
CPC ............... *C12N 1/20* (2013.01); *C07K 16/241* (2013.01); *C07K 16/244* (2013.01); *C12N 9/52* (2013.01); *C12N 15/70* (2013.01); *C12P 21/02* (2013.01); *C12R 1/19* (2013.01); *C07K 2317/14* (2013.01); *C07K 2317/55* (2013.01); *Y02P 20/52* (2015.11)

(58) Field of Classification Search
None
See application file for complete search history.

(56) References Cited

U.S. PATENT DOCUMENTS

| 5,264,365 | A | * | 11/1993 | Georgiou et al. | .......... | 435/252.8 |
| 5,508,192 | A | | 4/1996 | Georgiou et al. | | |
| 6,306,619 | B1 | * | 10/2001 | Jones et al. | ...... | 435/23 |
| 7,662,587 | B1 | | 2/2010 | Cheng et al. | | |
| 2006/0204493 | A1 | | 9/2006 | Huang et al. | | |
| 2012/0288894 | A1 | | 11/2012 | Ellis et al. | | |
| 2012/0295309 | A1 | | 11/2012 | Ellis et al. | | |
| 2012/0301920 | A1 | | 11/2012 | Ellis et al. | | |

FOREIGN PATENT DOCUMENTS

| WO | WO 02/48376 | 6/2002 |
| WO | WO 02/061090 | 8/2002 |
| WO | WO 2011/086136 | 7/2011 |
| WO | WO 2011/086138 | 7/2011 |
| WO | WO 2011/086139 | 7/2011 |

OTHER PUBLICATIONS

Baneyx, F. et al. "Construction and Characterization of *Escherichia coli* Strains Deficient in Multiple Secreted Proteases: Protease III Degrades High-Molecular-Weight Substrates In Vivo" *Journal of Bacteriology*, Apr. 1991, pp. 2696-2703, vol. 173, No. 8.
Spiess, C. et al. "A Temperature-Dependent Switch from Chaperone to Protease in a Widely Conserved Heat Shock Protein" *Cell*, Apr. 30, 1999, p. 339-347, vol. 97.
Skorko-Glonek, J. et al. "The proteolytic activity of the HtrA (DegP) protein from *Escherichia coli* at low temperatures" *Microbiology*, 2008, pp. 3649-3658, vol. 154.
Meerman, H. J. et al. "Construction and Characterization of a Set of *E. coli* Strains Deficient in All Known Loci Affecting the Proteolytic Stability of Secreted Recombinant Proteins" *Bio/Technology*, Nov. 1994, pp. 1107-1110, vol. 12.
Written Opinion in International Application No. PCT/GB2010/001790, Feb. 3, 2011, pp. 1-9.
Silber, K. R. et al. "Deletion of the *prc* (*tsp*) gene provides evidence for additional tail-specific proteolytic activity in *Escherichia coli* K-12" *Mol. Gen Genet*, 1994, vol. 242, pp. 237-240.
Chen, C. et al. "High-Level Accumulation of a Recombinant Antibody Fragment in the Periplasm of *Escherichia coli* Requires a Triple-Mutant (*degP prc spr*) Host Strain" *Biotechnology and Bioengineering*, Mar. 5, 2004, pp. 463-474, vol. 85, No. 5.
Database UniProt [Online] EBI Accession No. UNIPROT:B7UFJ2, Subname: Full=Predicted peptidase, outer membrane lipoprotein, Feb. 10, 2009, XP-002630316, p. 1.
Database UniProt [Online] EBI Accession No. UNIPROT:B7LAJ9, Subname: Full=Putative peptidase, outer membrane lipoprotein, Feb. 10, 2009, XP-002630317, p. 1.
Database UniProt [Online] EBI Accession No. UNIPROT:B7LJR7, Subname: Full=Putative peptidase, outer membrane lipoprotein, Feb. 10, 2009, XP-002630318, p. 1.
Database UniProt [Online] EBI Accession No. UNIPROT:C1M6L5, Subname: Full=Putative uncharacterized protein, May 26, 2009, XP-002630319, p. 1.
Hara, H. et al. "Overproduction of Penicillin-Binding Protein 7 Suppresses Thermosensitive Growth Defect at Low Osmolarity due to an *spr* Mutation of *Escherichia coli*" *Microbial Drug Resistance*, Jan. 1, 1996, pp. 63-72, vol. 2, No. 1.

(Continued)

*Primary Examiner* — Jim Ketter
(74) *Attorney, Agent, or Firm* — Saliwanchik, Lloyd & Eisenschenk

(57) ABSTRACT

A recombinant gram-negative bacterial cell comprising one or more of the following mutated protease genes: a) a mutated Tsp gene, wherein the mutated Tsp gene encodes a Tsp protein having reduced protease activity or is a knockout mutated Tsp gene; b) a mutated ptr gene, wherein the mutated ptr gene encodes a Protease III protein having reduced protease activity or is a knockout mutated ptr gene; and c) a mutated DegP gene encoding a DegP protein having chaperone activity and reduced protease activity; wherein the cell is isogenic to a wild-type bacterial cell except for the mutated Tsp gene and/or mutated ptr gene and/or mutated DegP gene and optionally a polynucleotide sequence encoding a protein of interest.

20 Claims, 18 Drawing Sheets

(56) References Cited

OTHER PUBLICATIONS

Aramini, J. et al. "Solution NMR Structure of the NlpC/P60 Domain of Lipoprotein Spr from *Escherichia coli*: Structural Evidence for a Novel Cysteine Peptidase Catalytic Triad" *Biochemistry*, 2008, pp. 9715-9717, vol. 47.

Tadokoro, A. et al. "Interaction of the *Escherichia coli* Lipoprotein Nlpl with Periplasmic Prc (Tsp) Protease" *Journal of Biochemistry*, 2004, pp. 185-191, vol. 135.

Written Opinion in International Application No. PCT/EP2011/050415, Jun. 20, 2011, pp. 1-15.

Hu, X. et al. "Optimisation of production of a domoic acid-binding scFv antibody fragment in *Escherichia coli* using molecular chaperones and functional immobilisation on a mesoporous silicate support" *Protein Expression and Purification*, 2007, pp. 194-201, vol. 52.

O'Dwyer, R. et al. "Microarray-based analysis of recombinant protein production in *E. coli*" *Microbial Cell Factories*, 2006, pp. 1-2 vol. 5, Supp 1.

Maskos, K. et al. "DsbA and DsbC-catalyzed Oxidative Folding of Proteins with Complex Disulfide Bridge Patterns In Vitro and In Vivo" *Journal of Molecular Biology*, 2003, pp. 495-513, vol. 325.

Written Opinion in International Application No. PCT/EP2011/050416, Apr. 26, 2011, pp. 1-7.

Written Opinion in International Application No. PCT/EP2011/050413, Apr. 8, 2011, pp. 17.

Baba, T. et al. "Construction of *Escherichia coli* K-12 in-frame, single-gene knockout mutants: the Keio collection" *Molecular Systems Biology*, 2006, pp. 1-11.

Pan, K.-L. et al. "Roles of DegP in Prevention of Protein Misfolding in the Periplasm upon Overexpression of Penicillin Acylase in *Escherichia coli*" *Journal of Bacteriology*, May 2003, pp. 3020-3030, vol. 185, No. 10.

\* cited by examiner

Figure 1a

Wild type ptr (protease III) 5'.

```
      *   M   P   R   S   T   W   F   K   A   L   L   L   V
     TGA ATG CCC CGC AGC ACC TGG TTC AAA GCA TTA TTG TTG TTA GTT

A   L   W   A   P   L   S
     GCC CTT TGG GCA CCC TTA AGT
```

Mutated Δ ptr (protease III) 5'.

```
         EcoR I
         ~~~~~~~~
      *   I   P   R   S   T   W   F   K   A   L   L   L   V
     TGA ATT CCC CGC AGC ACC TGG TTC AAA GCA TTA TTG TTG TTA GTT

Ase I
                         ~~~~~~~~
      A   L   W   A   H   *   C
     GCC CTT TGG GCA CAT TAA TGT
```

Figure 1b

Wild type Tsp 5'.

```
      M   N   M   F   F   R   L   T   A   L   A   G   L   L   A
     ATG AAC ATG TTT TTT AGG CTT ACC GCG TTA GCT GGC CTG CTT GCA

I   A   G   Q   T   F   A
     ATA GCA GGC CAG ACC TTC GCT
```

Mutated Δ Tsp 5'.

```
         EcoR I
         ~~~~~~~~
      M   N   S   F   L   G   L   P   R   *   L   A   C   L   Q
     ATG AAT TCG TTT TTA GGC TTA CCG CGT TAG CTG GCC TGC TTG CAA

Ase I
                              ~~~~~~~~
      *   Q   A   R   H   *   L
     TAG CAG GCC AGA CAT TAA TTG
```

Figure 1c

Wild type DegP

```
202    D   A   A   I   N   R   G   N   S   G   G
949    GAT GCA GCG ATC AAC CGT GGT AAC TCC GGT GGT
```

Mutated DegP S210A

```
                                   Ase I
                                 ~~~~~~~~
202    D   A   A   I   N   R   G   N   A   G   G
949    GAT GCA GCG ATT AAT CGT GGT AAC GCC GGT GGT
```

BACTERIAL HOST STRAIN

CROSS-REFERENCE TO RELATED APPLICATIONS

This application is a continuation of U.S. Ser. No. 13/497,987, filed Jun. 29, 2012, which is the U.S. national stage application of International Patent Application No. PCT/GB2010/001790, filed Sep. 23, 2010, the disclosures of which are hereby incorporated by reference in their entirety, including all figures, tables and amino acid or nucleic acid sequences.

The Sequence Listing for this application is labeled "Seq-List.txt" which was created on Feb. 20, 2015 and is 49 KB. The entire contents of the sequence listing is incorporated herein by reference in its entirety.

The invention relates to a recombinant bacterial host strain, particularly E. coli. The invention also relates to a method for producing a protein of interest in such a cell.

BACKGROUND OF THE INVENTION

Bacterial cells, such as E. coli, are commonly used for producing recombinant proteins. There are many advantages to using bacterial cells, such as E. coli, for producing recombinant proteins particularly due to the versatile nature of bacterial cells as host cells allowing the gene insertion via plasmids. E. coli have been used to produce many recombinant proteins including human insulin.

Despite the many advantages to using bacterial cells to produce recombinant proteins, there are still significant limitations including the difficulty of producing protease sensitive proteins. Proteases play an important role in turning over old and miss-folded proteins in the E. coli periplasm and cytoplasm. Bacterial proteases act to degrade the recombinant protein of interest, thereby often significantly reducing the yield of active protein.

A number of bacterial proteases have been identified. In E. coli proteases including Protease III (ptr), DegP, OmpT, Tsp, prlC, ptrA, ptrB, pepA-T, tsh, espc, eatA, clpP and lon have been identified.

The Protease III (ptr) protein is a 110 kDa periplasmic protease which degrades high molecular weight proteins.

Tsp (also known as Prc) is a 60 kDa periplasmic protease. The first known substrate of Tsp was Penicillin-binding protein-3 (PBP3) (Determination of the cleavage site involved in C-terminal processing of penicillin-binding protein 3 of Escherichia coli; Nagasawa H, Sakagami Y, Suzuki A, Suzuki H, Hara H, Hirota Y. J Bacteriol. 1989 November; 171(11): 5890-3 and Cloning, mapping and characterization of the Escherichia coli Tsp gene which is involved in C-terminal processing of penicillin-binding protein 3; Hara H, Yamamoto Y, Higashitani A, Suzuki H, Nishimura Y. J Bacteriol. 1991 August; 173 (15):4799-813) but it was later discovered that the Tsp was also able to cleave phage tail proteins and, therefore, it was renamed as Tail Specific Protease (Tsp) (Silber et al., Proc. Natl. Acad. Sci. USA, 89: 295-299 (1992)). Silber et al. (Deletion of the prc(tsp) gene provides evidence for additional tail-specific proteolytic activity in Escherichia coli K-12; Silber, K. R., Sauer, R. T.; Mol Gen Genet 1994 242:237-240) describes a prc deletion strain (KS1000) wherein the mutation was created by replacing a segment of the prc gene with a fragment comprising a Kan$^r$ marker.

DegP (also known as HtrA) is a 46 kDa protein having dual function as a chaperone and a protease (Families of serine peptidases; Rawlings N D, Barrett A J. Methods Enzymol. 1994; 244:19-61).

It is known to knockout bacterial proteases in order to affect the yield of recombinant protein.

Georgiou et al. (Construction and characterization of Escherichia coli strains deficient in multiple secreted proteases: protease III degrades high-molecular-weight substrates in vivo. Baneyx F, Georgiou G. J Bacteriol. 1991 April; 173(8):2696-703) studied the effects on growth properties and protein stability of E. coli strains deficient in protease III constructed by insertional inactivation of the ptr gene and observed an increase in the expression of a protease-sensitive secreted polypeptide. A strain comprising the ptr mutation and also deficient in the secreted protease DegP was also produced and found to have a decreased growth rate and an increase in protein expression. In Georgiou et al., the E. coli strains deficient in protease III and/or DegP were constructed from the KS272 parental strain which already comprises a number of genomic mutations.

U.S. Pat. No. 5,264,365 (Georgiou et al.) discloses the construction of protease-deficient Escherichia coli hosts which when combined with an expression system are useful for the production of proteolytically sensitive polypeptides.

Meerman et al. (Construction and characterization of Escherichia coli strains deficient in All Known Loci Affecting the Proteolytic Stability of Secreted Recombinant Proteins. Meerman H. J., Georgeou G., Nature Biotechnology, 1994 November; 12; 1107-1110) disclose E. coli strains comprising mutations in the rpoH, the RNA polymerase sigma factor responsible for heat shock protein synthesis, and different combinations of mutations in protease genes including DegP, Protease III, Tsp(Prc) and OmpT, where null mutations of the protease genes were caused by insertional mutations. In Meerman et al., the E. coli strains deficient in one or more of Tsp, protease III and DegP were constructed from the KS272 parental strain which already comprises a number of genomic mutations.

U.S. Pat. No. 5,508,192 (Georgiou et al.) discloses a method of producing recombinant polypeptides in protease-deficient bacterial hosts and constructs of single, double, triple and quadruple protease deficient bacteria which also carry a mutation in the rpoH gene.

Chen et al describes the construction of E. coli strains carrying different combinations of mutations in prc (Tsp) and DegP created by amplifying the upstream and downstream regions of the gene and ligating these together on a vector comprising selection markers and a sprW148R mutation (High-level accumulation of a recombinant antibody fragment in the periplasm of Escherichia coli requires a triple-mutant (ΔDegP Δprc spr W148R) host strain. Chen C, Snedecor B, Nishihara J C, Joly J C, McFarland N, Andersen D C, Battersby J E, Champion K M. Biotechnol Bioeng. 2004 Mar. 5; 85(5):463-74). The combination of the ΔDegP, Δprc and W148Rspr mutations were found to provide the highest levels of antibody light chain, antibody heavy chain and F(ab')2-LZ. EP1341899 discloses an E. coli strain that is deficient in chromosomal DegP and prc encoding proteases DegP and Prc, respectively, and harbors a mutant spr gene that encodes a protein that suppresses growth phenotypes exhibited by strains harboring prc mutants.

Kandilogiannaki et al (Expression of a recombinant human anti-MUC 1 scFv fragment in protease-deficient Escherichia coli mutants. Kandilogiannaki M, Koutsoudakis G, Zafiropoulos A, Krambovitis E. Int J Mol Med. 2001 June; 7(6):659-64) describes the utilization of a protease deficient strain for the expression of a scFv protein. The protease deficient bacterial strains used previously to express recombinant proteins comprise further mutations of genes involved in cell metabolism and DNA replication such as, for example phoA, JhuA, lac, rec, gal, ara, arg, thi and pro in *E. coli* strains. These mutations may have many deleterious effects on the host cell including effects on cell growth, stability, recombinant protein expression yield and toxicity. Strains having one or more of these genomic mutations, particularly strains having a high number of these mutations, may exhibit a loss of fitness which reduces bacterial growth rate to a level which is not suitable for industrial protein production. Further, any of the above genomic mutations may affect other genes in cis and/or in trans in unpredictable harmful ways thereby altering the strain's phenotype, fitness and protein profile. Further, the use of heavily mutated cells is not generally suitable for producing recombinant proteins for commercial use, particularly therapeutics, because such strains generally have defective metabolic pathways and hence may grow poorly or not at all in minimal or chemically defined media.

Protease deficient bacterial strains also typically comprise knockout mutations to one or more protease encoding genes which have been created by insertion of a DNA sequence into the gene coding sequence. The inserted DNA sequence typically codes for a selection marker such as an antibiotic resistance gene. Whilst this mutation method may be effective at knocking out the target protease, there are many disadvantages associated with this method. One disadvantage is the insertion of the foreign DNA, such as an antibiotic resistance gene, causes disruption in the host's genome which may result in any number of unwanted effects including the overexpression of detrimental proteins and/or down-regulation or knockout of other essential proteins. This effect is particularly evident for those genes positioned immediately upstream or downstream of the target protease gene. A further disadvantage to the insertion of foreign DNA, particularly antibiotic resistance genes, is the unknown phenotypic modifications to the host cell which may affect expression of the target protein and/or growth of the host cell and may also make the host cell unsuitable for production of proteins intended for use as therapeutics. Antibiotic resistance proteins are particularly disadvantageous for biosafety requirements large scale manufacturing particularly for the production of therapeutics for human administration. A further disadvantage to the insertion of antibiotic resistance markers is the metabolic burden on the cell created by the expression of the protein encoded by the antibiotic resistance gene. The use of antibiotic resistance markers for use as markers for genetic manipulations such as knockout mutations, are also limited by the number of different antibiotic resistance markers available. Accordingly, there is still a need to provide new bacterial strains which provide advantageous means for producing recombinant proteins.

SUMMARY OF THE INVENTION

It is an aim of the present invention to solve one or more of the problems described above.

In a first aspect the present invention provides a recombinant gram-negative bacterial cell comprising one or more of the following mutated protease genes:
  a. a mutated Tsp gene, wherein the mutated Tsp gene encodes a Tsp protein having reduced protease activity or is a knockout mutated Tsp gene;
  b. a mutated ptr gene, wherein the mutated ptr gene encodes a Protease III protein having reduced protease activity or is a knockout mutated ptr gene; and
  c. a mutated DegP gene encoding a DegP protein having chaperone activity and reduced protease activity;

wherein the cell is isogenic to a wild-type bacterial cell except for the mutated Tsp gene and/or mutated ptr gene and/or mutated Deg P gene and optionally a polynucleotide sequence encoding a protein of interest.

In one embodiment the present invention provides a cell comprising a mutated Tsp gene, wherein the mutated Tsp gene encodes a Tsp protein having reduced protease activity or is a knockout mutated Tsp gene and no further mutated protease genes. Accordingly, the present invention provides a cell which is isogenic to a wild-type bacterial cell except for the mutated Tsp gene and optionally a polynucleotide sequence encoding a protein of interest.

In one embodiment the present invention provides a cell comprising a mutated ptr gene, wherein the mutated ptr gene encodes a Protease III protein having reduced protease activity or is a knockout mutated ptr gene and no further mutated protease genes. Accordingly, the present invention provides a cell which is isogenic to a wild-type bacterial cell except for the mutated ptr gene and optionally a polynucleotide sequence encoding a protein of interest.

In one embodiment the present invention provides a cell comprising a mutated DegP gene encoding a DegP protein having chaperone activity and reduced protease activity and no further mutated protease genes. Accordingly, the present invention provides a cell which is isogenic to a wild-type bacterial cell except for the mutated DegP gene and optionally a polynucleotide sequence encoding a protein of interest.

In one embodiment the present invention provides a cell comprising a mutated DegP gene encoding a DegP protein having chaperone activity and reduced protease activity, a mutated Tsp gene, wherein the mutated Tsp gene encodes a Tsp protein having reduced protease activity or is a knockout mutated Tsp gene and no further mutated protease genes. Accordingly, the present invention provides a cell which is isogenic to a wild-type bacterial cell except for the mutated DegP gene and the mutated Tsp gene and optionally a polynucleotide sequence encoding a protein of interest.

In one embodiment the present invention provides a cell comprising a mutated ptr gene, wherein the mutated ptr gene encodes a Protease III protein having reduced protease activity or is a knockout mutated ptr gene, a mutated Tsp gene wherein the mutated Tsp gene encodes a Tsp protein having reduced protease activity or is a knockout mutated Tsp gene and no further mutated protease genes. Accordingly, the present invention provides a cell which is isogenic to a wildtype bacterial cell except for the mutated ptr gene and the mutated Tsp gene and optionally a polynucleotide sequence encoding a protein of interest. In one embodiment the present invention provides a cell comprising a mutated DegP gene encoding a DegP protein having chaperone activity and reduced protease activity, a mutated ptr gene, wherein the mutated ptr gene encodes a Protease III protein having reduced protease activity or is a knockout mutated ptr gene and no further mutated protease genes. Accordingly, the present invention provides a cell which is isogenic to a wildtype bacterial cell except for the mutated DegP gene and mutated ptr gene and optionally a polynucleotide sequence encoding a protein of interest.

In one embodiment the present invention provides a cell comprising a mutated DegP gene encoding a DegP protein having chaperone activity and reduced protease activity, a mutated ptr gene, wherein the mutated ptr gene encodes a Protease III protein having reduced protease activity or is a knockout mutated ptr gene, a mutated Tsp gene, wherein the mutated Tsp gene encodes a Tsp protein having reduced protease activity or is a knockout mutated Tsp gene and no further mutated protease genes. Accordingly, the present invention provides a cell which is isogenic to a wild-type bacterial cell except for the mutated DegP gene, the mutated ptr gene and the mutated Tsp gene and optionally a polynucleotide sequence encoding a protein of interest.

In a preferred embodiment the mutated ptr gene and/or the mutated Tsp gene referred to above are knockout mutations.

The present inventors have found that a bacterial host strain isogenic to a wild-type bacterial cell except for one or more of the above mutated protease provides an advantageous host for producing a recombinant protein of interest. The cells provided by the present invention have reduced protease activity compared to a non-mutated cell, which may reduce proteolysis of a recombinant protein of interest, particularly proteins of interest which are proteolytically sensitive. In addition, the cell according to the present invention carries only minimal mutations to the genomic sequence in order to introduce one or more of the above protease mutations and does not carry any other mutations which may have deleterious effects on the cell's growth and/or ability to express a protein of interest.

One or more of the gram-negative cells provided by the present invention may provide a high yield of the recombinant protein of interest. One or more of the gram-negative cells provided by the present invention may provide a fast rate of production of a protein of interest. One or more of the cells may provide fast initial yield of the recombinant protein of interest. Further, one or more of the cells may show good growth characteristics.

In a second aspect, the present invention provides a recombinant gram-negative bacterial cell comprising:
a. a knockout mutated Tsp gene comprising a mutation to the gene start codon and/or one or more stop codons positioned downstream of the gene start codon and upstream of the gene stop codon; and/or
b. a knockout mutated ptr gene comprising a mutation to the gene start codon and/or one or more stop codons positioned downstream of the gene start codon and upstream of the gene stop codon; and
c. optionally a mutated DegP gene encoding a DegP protein having chaperone activity and reduced protease activity.

In one embodiment the present invention provides a cell comprising a knockout mutated Tsp gene comprising a mutation to the gene start codon and/or one or more stop codons positioned downstream of the gene start codon and upstream of the gene stop codon.

In one embodiment the present invention provides a cell comprising a knockout mutated ptr gene comprising a mutation to the gene start codon and/or one or more stop codons positioned downstream of the gene start codon and upstream of the gene stop codon.

In one embodiment the present invention provides a cell comprising a mutated DegP gene encoding a DegP protein having chaperone activity and reduced protease activity and a knockout mutated Tsp gene comprising a mutation to the gene start codon and/or one or more stop codons positioned downstream of the gene start codon and upstream of the gene stop codon.

In one embodiment the present invention provides a cell comprising a knockout mutated ptr gene comprising a mutation to the gene start codon and/or one or more stop codons positioned downstream of the gene start codon and upstream of the gene stop codon and a knockout mutated Tsp gene comprising a mutation to the gene start codon and/or one or more stop codons positioned downstream of the gene start codon and upstream of the gene stop codon.

In one embodiment the present invention provides a cell comprising a mutated DegP gene encoding a DegP protein having chaperone activity and reduced protease activity and a knockout mutated ptr gene comprising a mutation to the gene start codon and/or one or more stop codons positioned downstream of the gene start codon and upstream of the gene stop codon.

In one embodiment the present invention provides a cell comprising a mutated DegP gene encoding a DegP protein having chaperone activity and reduced protease activity, a knockout mutated ptr gene comprising a mutation to the gene start codon and/or one or more stop codons positioned downstream of the gene start codon and upstream of the gene stop codon and a knockout mutated Tsp gene comprising a mutation to the gene start codon and/or one or more stop codons positioned downstream of the gene start codon and upstream of the gene stop codon.

The cell provided by the second aspect of the present invention overcomes the above described disadvantages of knockout mutation methods employing DNA insertion typically used in the art to provide protease deficient strains. In the present invention the knockout mutations to the ptr gene and/or the Tsp gene are provided by a mutation to the gene start codon and/or one or more stop codons positioned downstream of the gene start codon and upstream of the gene stop codon. A mutation, such as a missense point mutation, to the target knockout gene start codon ensures that the target gene does not comprise a suitable start codon at the start of the coding sequence. The insertion of one or more stop codons positioned between the gene start codon and stop codon ensures that even if transcription of the gene is initiated, the full coding sequence will not be transcribed. The host genome required minimal disruption to mutate the start codon and/or insert one or more stop codons, thereby minimizing the deleterious effects of genome disruption on the expression of the target protein and/or growth of the host cell. The cell of the present invention may also be more suitable for production of proteins intended for use as therapeutics due to the minimal disruption to the cell genome.

In a third aspect, the present invention provides a method for producing a recombinant protein of interest comprising expressing the recombinant protein of interest in a recombinant gram-negative bacterial cell as defined above in the first aspect or second aspect of the present invention.

BRIEF DESCRIPTION OF THE DRAWINGS

FIG. 1a shows the 5' end of the wild type ptr (protease III) (SEQ ID NO: 21) and knockout mutated ptr (protease III) (SEQ ID NO: 22) protein and gene sequences.

FIG. 1b shows the 5' end of the wild type Tsp (SEQ ID NO: 23) and knockout mutated Tsp (SEQ ID NO: 24) protein and gene sequences.

FIG. 1c shows a region of the wild type DegP (SEQ ID NO: 25) and mutated DegP (SEQ ID NO: 26) protein and gene sequences.

BRIEF DESCRIPTION OF THE SEQUENCES

Figure 2:
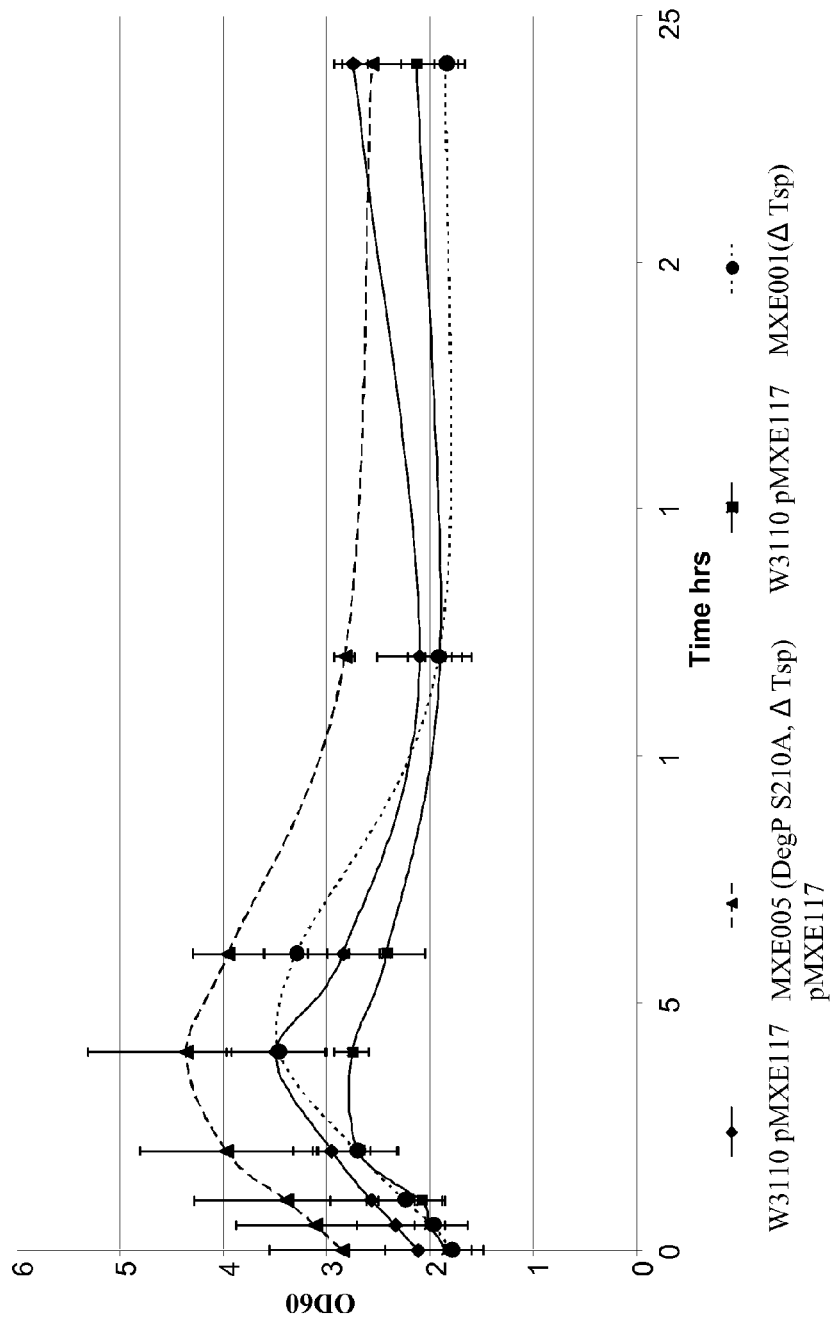
FIG. 2 shows the growth of *E. coli* strain MXE001 carrying a knockout mutated Tsp gene and *E. coli* strain MXE005 carrying a knockout mutated Tsp gene and mutated DegP gene compared to *E. coli* wild type W3110.

SEQ ID NO:1 is the DNA sequence of the non-mutated Tsp gene including the 6 nucleotides ATGAAC upstream of the start codon.

SEQ ID NO:2 is the amino acid sequence of the non-mutated Tsp protein.

SEQ ID NO:3 is the DNA sequence of a mutated knockout Tsp gene including the 6 nucleotides ATGAAT upstream of the start codon.

SEQ ID NO:4 is the DNA sequence of the non-mutated Protease III gene.

SEQ ID NO:5 is the amino acid sequence of the non-mutated Protease III protein. SEQ ID NO:6 is the DNA sequence of a mutated knockout Protease III gene.

SEQ ID NO:7 is the DNA sequence of the non-mutated DegP gene.

SEQ ID NO:8 is the amino acid sequence of the non-mutated DegP protein.

SEQ ID NO:9 is the DNA sequence of a mutated DegP gene.

SEQ ID NO:10 is the amino acid sequence of a mutated DegP protein.

SEQ ID NO: 11 is the amino acid sequence of the light chain variable region of an anti-TNF antibody.

SEQ ID NO:12 is the amino acid sequence of the heavy chain variable region of an anti-TNF antibody.

SEQ ID NO:13 is the amino acid sequence of the light chain of an anti-TNF antibody.

SEQ ID NO:14 is the amino acid sequence of the heavy chain of an anti-TNF antibody.

SEQ ID NO: 15 is the sequence of the 3' oligonucleotide primer for the region of the mutated Tsp gene comprising the Ase I restriction site.

SEQ ID NO: 16 is the sequence of the 5' oligonucleotide primer for the region of the mutated Tsp gene comprising the Ase I restriction site.

SEQ ID NO: 17 is the sequence of the 3' oligonucleotide primer for the region of the mutated Protease III gene comprising the Ase I restriction site.

SEQ ID NO: 18 is the sequence of the 5' oligonucleotide primer for the region of the mutated Protease III gene comprising the Ase I restriction site.

SEQ ID NO: 19 is the sequence of the 5' oligonucleotide primer for the region of the mutated DegP gene comprising the Ase I restriction site.

SEQ ID NO: 20 is the sequence of the 3' oligonucleotide primer for the region of the mutated DegP gene comprising the Ase I restriction site.

Detailed Description of the Preferred Embodiments of the Invention

In the first aspect and second aspect of the present invention the present inventors have provided a recombinant gram-negative bacterial cell suitable for expressing a protein of interest which comprises only the minimal mutations to the genome required to introduce one or more protease mutations. In the first aspect of the invention, the bacterial cell only differs from a wild-type bacterial cell by the one or more mutated protease genes selected from a mutated DegP gene encoding a DegP protein having chaperone activity and reduced protease activity; a mutated ptr; and a mutated Tsp gene and optionally a polynucleotide sequence encoding a protein of interest. In the second aspect of the present invention the bacterial cell comprises knockout mutations of Tsp and/or Protease III, wherein the Tsp and/or Protease III gene comprises a mutation to the gene start codon and/or one or more stop codons positioned downstream of the gene start codon and upstream of the gene stop codon.

The cells provided by the first and second aspects of the present invention have reduced protease activity compared to non-mutated cell, which may reduce proteolysis of a recombinant protein of interest, particularly proteins of interest which are proteolytically sensitive. Therefore, one or more of the gram-negative cells provided by the first and second aspects of the present invention may provide higher yield of the intact recombinant protein of interest and a lower yield, or preferably no yield, of proteolytic fragments of the protein of interest compared to a non-mutated bacterial cell.

The skilled person would easily be able to test a candidate cell clone to see if it has the desired yield of a protein of interest using methods well known in the art including a fermentation method, ELISA and protein G hplc. Suitable fermentation methods are described in Humphreys D P, et al. (1997). Formation of dimeric Fabs in *E. coli*: effect of hinge size and isotype, presence of interchain disulphide bond, Fab' expression levels, tail piece sequences and growth conditions. J. IMMUNOL. METH. 209: 193-202; Backlund E. Reeks D. Markland K. Weir N. Bowering L. Larsson G. Fedbatch design for periplasmic product retention in *Escherichia coli*, Journal Article. Research Support, Non-U.S. Gov't Journal of Biotechnology. 135(4):358-65, 2008 Jul. 31; Champion K M. Nishihara. J C. Joly J C. Arnott D. Similarity of the *Escherichia coli* proteome upon completion of different biopharmaceutical fermentation processes. [Journal Article] Proteomics. 1(9):1133-48, 2001 September; and Horn U. Strittmatter W. Krebber A. Knupfer U. Kujau M. Wenderoth R. Muller K. Matzku S. Pluckthun A. Riesenberg D. High volumetric yields of functional dimeric miniantibodies in *Escherichia coli*, using an optimized expression vector and high-celldensity fermentation under non-limited growth conditions, Journal Article. Research Support, Non-U.S. Gov't Applied Microbiology & Biotechnology. 46(5-6):524-32, 1996 December. The skilled person would also easily be able to test secreted protein to see if the protein is correctly folded using methods well known in the art, such as protein G HPLC, circular dichroism, NMR, X-Ray crystallography and epitope affinity measurement methods.

One or more of the recombinant bacterial cells of the first and second aspects of the present invention may exhibit significantly improved protein yield compared to a non-mutated bacterial cell. The improved protein yield may be the periplasmic protein yield and/or the supernatant protein yield. One or more of the recombinant bacterial cells of the first and second aspects of the present invention may be capable of faster rate of production of a protein of interest and, therefore, the same quantity of a protein of interest may be produced in a shorter time compared to a non-mutated bacterial cell. The faster rate of production of a protein of interest may be especially significant over the initial period of growth of the cell, for example over the first 5, 10, 20 or 30 hours post induction of protein expression.

The cells according to the present invention comprising the Tsp mutation, which is preferably the knockout mutation, either alone or in combination with the DegP mutation or the Protease III mutation, are particularly preferred. These cells exhibit a higher yield and a faster initial yield of a protein of interest compared to a non-mutated cell. Example of such cell lines comprising the mutated Tsp gene either alone or in combination with mutated DegP gene or the mutated ptr gene are mutant *E. coli* cell strains MXE001 having genotype ΔTsp and deposited on 21 May 2009 at the National Collection of Type Cultures, HPA, United Kingdom, under Accession number NCTC13444, MXE004 having genotype ΔTsp Δptr, and deposited on 21 May 2009 at the National Collection of Type Cultures, HPA, United Kingdom, under Accession number NCTC13447, and MXE005 having genotype ΔTsp, DegP S210A and deposited on 21 May 2009 at the National Collection of Type Cultures, HPA, United Kingdom, under Accession number NCTC13448.

Further, one or more of the cells may show good growth characteristics including cell growth and/or reproduction which may be substantially the same as a non-mutated bacterial cell or improved compared to a non-mutated bacterial cell.

The genome of the cell according to the first aspect of the present invention has had minimal disruption to the genome compared to a wild-type cell thereby reducing deleterious effects of other mutations typically found in host cells on the expression of other cellular proteins. Accordingly, one or more of the recombinant host cells according to the first aspect of the present invention may exhibit improved protein expression and/or improved growth characteristics compared to cells comprising further genetically engineered mutations to the genomic sequence.

The genome of the cell according to the second aspect of the present invention has had minimal disruption to the genome to introduce the knockout mutations thereby reducing deleterious effects of creating protease gene knockouts by inserting DNA, such as antibiotic resistance markers. Accordingly, one or more of the recombinant host cells according to the second aspect of the present invention may exhibit improved protein expression and/or improved growth characteristics compared to cells comprising protease knockout mutations created by the insertion of DNA, such as antibiotic resistance markers.

The cells provided by the first and second aspects of the present invention are also more suitable for use to produce therapeutic proteins compared to cells comprising further disruptions to the cell genome.

The present invention will now be described in more detail. All embodiments herein described refer to the first, second and third aspects of the present invention unless specifically stated otherwise.

The terms "protein" and "polypeptide" are used interchangeably herein, unless the context indicates otherwise. "Peptide" is intended to refer to 10 or less amino acids.

The terms "polynucleotide" includes a gene, DNA, cDNA, RNA, mRNA etc unless the context indicates otherwise.

As used herein, the term "comprising" in context of the present specification should be interpreted as "including".

The non-mutated cell or control cell in the context of the present invention means a cell of the same type as the recombinant gram-negative cell of the invention wherein the cell has not been modified to carry the above protease mutations. For example, a non-mutated cell may be a wild-type cell and may be derived from the same population of host cells as the cells of the invention before modification to introduce the one or more mutations.

The expressions "cell", "cell line", "cell culture" and "strain" are used interchangeably.

The term "isogenic" in the context of the present invention means that the genome of the cell of the present invention has substantially the same or the same genomic sequence compared to wild-type cell except for one or more of the above mutated protease genes and optionally a polynucleotide encoding a protein of interest. In this embodiment the cell according to the present invention comprises no further non-naturally occurring or genetically engineered mutations compared to the wild-type cell. In one embodiment the cell according to the present invention may have substantially the same genomic sequence compared to the wild-type cell except for the above protease mutations and optionally a polynucleotide encoding a protein of interest taking into account any naturally occurring mutations which may occur. It should also be noted that during the introduction of the protease mutations into the strain, for example by a gene replacement vector, and during the introduction of the polynucleotide encoding the protein of interest into the strain one or more further genomic mutations may be introduced into the strain. Accordingly, in one embodiment the cell according to the present invention may have substantially the same genomic sequence compared to the wild-type cell except for the above protease mutations and optionally a polynucleotide encoding a protein of interest taking into account any naturally occurring mutations which may occur and any further genomic mutations which may result from the introduction of the protease mutations and/or the polynucleotide encoding the protein of interest.

Examples of gene mutations involved in cell metabolism and DNA replication, which are commonly used in *E. coli* strains in the art but are not used in the cell according to the present invention include phoA, JhuA, lac, rec, gal, ara, arg, thi and pro. In one embodiment, the cell according to the present invention may have exactly the same genomic sequence compared to the wild-type cell except for the above protease mutations and optionally a polynucleotide encoding a protein of interest.

The term "wild-type" in the context of the present invention means a strain of a gram-negative bacterial cell as it may occur in nature or may be isolated from the environment, which does not carry any genetically engineered mutations. An example of a wild-type strain of *E. coli* is W3110, such as W3110 K-12 strain. Examples of wild-type strains include strains of the K-12 strain family which includes W3110 (F- λ- rph-1 INV(rrnD, rrnE) ilvG) (ATCC27325), MG1655 (F- λ- ilvG- rfb-50 rph-1) (ATCC700926), W1485 (F+ λ- rph-1 rpoS396) (ATCC12435), W3101 (F- λ- ilvG- IN(rrnD-rrnE)1 rph-1 galT22) and BW30270 (F- λ- fnr+). Further examples of wild-type E. coli strains include the W strain (ATCC9637) and the B strain (ATCC23226).

Any suitable gram-negative bacterium may be used as the parental cell for producing the recombinant cell of the present invention. Suitable gram-negative bacterium include Salmonella typhimurium, Pseudomonas fluorescens, Erwinia carotovora, Shigella, Klebsiella pneumoniae, Legionella pneumophila, Pseudomonas aeruginosa, Acinetobacter baumannii and E. coli. Preferably the parental cell is E. coli. Any suitable strain of E. coli may be used in the present invention as the parental cell. Examples of suitable E. coli strains include the K-12 strain family which comprises W3110 (F- λ- rph-1 INV(rrnD, rrnE) ilvG) (ATCC27325), MG1655 (F- λ- ilvG- rfb-50 rph-1) (ATCC700926), W1485 (F+ λ- rph-1 rpoS396) (ATCC12435), W3101 (F- λ- ilvG- IN(rrnD-rrnE)1 rph-1 galT22) and BW30270 (F- λ- fnr+). Further suitable E. coli strains include the W strain (ATCC9637) and the B strain (ATCC23226). Preferably a wild-type W3110 strain, such as K-12 W3110, is used.

The cell according to the first aspect of the present is isogenic to a wild-type bacterial cell except for the one or more mutated protease genes and optionally a polynucleotide sequence encoding a protein of interest. The cell according to the second aspect of the present invention is preferably also isogenic to a wild-type bacterial cell except for the one or more mutated protease genes and optionally a polynucleotide sequence encoding a protein of interest.

In a preferred embodiment, the cell is isogenic to a wild-type E. coli cell except for the above protease mutations and optionally a polynucleotide encoding a protein of interest. More preferably the cell according to the present invention is isogenic to an E. coli strain W3110 except for the above protease mutations and optionally a polynucleotide encoding a protein of interest. Examples of other suitable wild-type E. coli cells which the cell according to the present invention may be isogenic to except for the above protease mutations and optionally the polynucleotide encoding a protein of interest are strains of the K-12 strain family which includes W3110 (F- λ- rph-1 INV(rrnD, rrnE) ilvG) (ATCC27325), MG1655 (F- λ- ilvG- rfb-50 rph-1) (ATCC700926), W1485 (F+ λ- rph-1 rpoS396) (ATCC12435), W3101 (F- λ- ilvG- IN(rrnD-rrnE)1 rph-1 galT22) and BW30270 (F- λ- fnr+). Further suitable wild-type E. coli strains which the cell according to the present invention may be isogenic to except for the above protease mutations and optionally the polynucleotide encoding a protein of interest are include the W strain (ATCC9637) and the B strain (ATCC23226).

The cell of the present invention may further differ from a wild-type cell by comprising a polynucleotide encoding the protein of interest. In this embodiment, the polynucleotide encoding the protein of interest may be contained within a suitable expression vector transformed into the cell and/or integrated into the host cell's genome. In the embodiment where the polynucleotide encoding the protein of interest is inserted into the host's genome, the cell of the present invention will also differ from a wild-type cell due to the inserted polynucleotide sequence encoding the protein of interest. Preferably the polynucleotide is in an expression vector in the cell thereby causing minimal disruption to the host cell's genome.

In certain embodiments of the present invention the recombinant gram-negative bacterial cell comprises a mutated DegP gene encoding a DegP protein having chaperone activity and reduced protease activity. As used herein, "DegP" means a gene encoding DegP protein (also known as HtrA), which has dual function as a chaperone and a protease (Families of serine peptidases; Rawlings N D, Barrett A J. Methods Enzymol. 1994; 244:19-61). The sequence of the non-mutated DegP gene is shown in SEQ ID NO: 7 and the sequence of the non-mutated DegP protein is shown in SEQ ID NO: 8.

At low temperatures DegP functions as a chaperone and at high temperatures DegP has a preference to function as a protease (A Temperature-Dependent Switch from Chaperone to Protease in a Widely Conserved Heat Shock Protein. Cell, Volume 97, Issue 3, Pages 339-347. Spiess C, Beil A, Ehrmann M) and The proteolytic activity of the HtrA (DegP) protein from Escherichia coli at low temperatures, Skorko-Glonek J et at Microbiology 2008, 154, 3649-3658).

In the embodiments where the cell comprises the DegP mutation the DegP mutation in the cell provides a mutated DegP gene encoding a DegP protein having chaperone activity but not full protease activity.

The expression "having chaperone activity" in the context of the present invention means that the mutated DegP protein has the same or substantially the same chaperone activity compared to the wild-type non-mutated DegP protein. Preferably, the mutated DegP gene encodes a DegP protein having 50% or more, 60% or more, 70% or more, 80% or more, 90% or more or 95% or more of the chaperone activity of a wild-type non-mutated DegP protein. More preferably, the mutated DegP gene encodes a DegP protein having the same chaperone activity compared to wild-type DegP.

The expression "having reduced protease activity" in the context of the present invention means that the mutated DegP protein does not have the full protease activity compared to the wild-type non-mutated DegP protein. Preferably, the mutated DegP gene encodes a DegP protein having 50% or less, 40% or less, 30% or less, 20% or less, 10% or less or 5% or less of the protease activity of a wild-type non-mutated DegP protein. More preferably, the mutated DegP gene encodes a DegP protein having no protease activity. The cell is not deficient in chromosomal DegP i.e. the DegP gene sequences has not been deleted or mutated to prevent expression of any form of DegP protein.

Any suitable mutation may be introduced into the DegP gene in order to produce a protein having chaperone activity and reduced protease activity. The protease and chaperone activity of a DegP protein expressed from a gram-negative bacterium may be easily tested by a person skilled in the art by any suitable method such as the method described in Spiess et al wherein the protease and chaperone activities of DegP were tested on MalS, a natural substrate of DegP (A Temperature-Dependent Switch from Chaperone to Protease in a Widely Conserved Heat Shock Protein. Cell, Volume 97, Issue 3, Pages 339-347. Spiess C, Beil A, Ehrmann M) and also the method described in The proteolytic activity of the HtrA (DegP) protein from Escherichia coli at low temperatures, Skorko-Glonek J et at Microbiology 2008, 154, 3649-3658.

DegP is a serine protease and has an active center consisting of a catalytic triad of amino acid residues of His105, Asp135 and Ser210 (Families of serine peptidases, Methods Enzymol., 1994, 244:19-61 Rawlings N and Barrett A). The DegP mutation to produce a protein having chaperone activity and reduced protease activity may comprise a mutation, such as a missense mutation to one, two or three of His105, Asp135 and Ser210. Accordingly, the mutated DegP gene may comprise:

a mutation to His105; or
a mutation to Asp135; or
a mutation to Ser210; or
a mutation to His105 and Asp135; or
a mutation to His105 and Ser210; or
a mutation to Asp135 and Ser210; or
a mutation to His105, Asp135 and Ser210.

One, two or three of His105, Asp135 and Ser210 may be mutated to any suitable amino acid which results in a protein having chaperone activity and reduced protease activity. For example, one, two or three of His105, Asp135 and Ser210 may be mutated to a small amino acid such as Gly or Ala. A further suitable mutation is to change one, two or three of His105, Asp135 and Ser210 to an amino acid having opposite properties such as Asp135 being mutated to Lys or Arg, polar His105 being mutated to a non-polar amino acid such as Gly, Ala, Val or Leu and small hydrophilic Ser210 being mutated to a large or hydrophobic residue such as Val, Leu, Phe or Tyr. Preferably, the DegP gene comprises the point mutation S210A, as shown in FIG. 1c, which has been found to produce a protein having chaperone activity but not protease activity (A Temperature-Dependent Switch from Chaperone to Protease in a Widely Conserved Heat Shock Protein. Cell, Volume 97, Issue 3, Pages 339-347. Spiess C, Beil A, Ehrmann M).

The present invention also provides a recombinant gram-negative bacterial cell comprising a mutated DegP gene encoding a DegP protein having chaperone activity and reduced protease activity, wherein the DegP gene comprises a mutation to His105; or a mutation to Asp135; or a mutation to His105 and Asp135; or a mutation to His105 and Ser210; or a mutation to Asp135 and Ser210; or a mutation to His105, Asp135 and Ser210, as discussed above.

DegP has two PDZ domains, PDZ1 (residues 260-358) and PDZ2 (residues 359-448), which mediate protein-protein interaction (A Temperature-Dependent Switch from Chaperone to Protease in a Widely Conserved Heat Shock Protein. Cell, Volume 97, Issue 3, Pages 339-347. Spiess C, Beil A, Ehrmann M). In one embodiment of the present invention the degP gene is mutated to delete PDZ1 domain and/or PDZ2 domain. The deletion of PDZ1 and PDZ2 results in complete loss of protease activity of the DegP protein and lowered chaperone activity compared to wild-type DegP protein whilst deletion of either PDZ1 or PDZ2 results in 5% protease activity and similar chaperone activity compared to wild-type DegP protein (A Temperature-Dependent Switch from Chaperone to Protease in a Widely Conserved Heat Shock Protein. Cell, Volume 97, Issue 3, Pages 339-347. Spiess C, Beil A, Ehrmann M).

The present invention also provides a recombinant gram-negative bacterial cell comprising a mutated DegP gene encoding a DegP protein having chaperone activity and reduced protease activity, wherein the degP gene is mutated to delete PDZ1 domain and/or PDZ2 domain, as discussed above.

The mutated DegP gene may also comprise a silent non-naturally occurring restriction site, such as Ase I in order to aid in identification and screening methods, for example as shown in FIG. 1c.

The preferred sequence of the mutated DegP gene comprising the point mutation S210A and an Ase I restriction marker site is provided in SEQ ID NO: 9 and the encoded protein sequence is shown in SEQ ID NO: 10. The mutations which have been made in the mutated DegP sequence of SEQ ID NO: 9 are shown in FIG. 1c.

In the embodiments of the present invention wherein the cell comprises a mutated DegP gene encoding a DegP protein having chaperone activity and reduced protease activity, one or more of the cells provided by the present invention may provide improved yield of correctly folded proteins from the cell relative to mutated cells wherein the DegP gene has been mutated to knockout DegP preventing DegP expression, such as chromosomal deficient DegP. In a cell comprising a knockout mutated DegP gene preventing DegP expression, the chaperone activity of DegP is lost completely whereas in the cell according to the present invention the chaperone activity of DegP is retained whilst the full protease activity is lost. In these embodiments, one or more cells according to the present invention have a lower protease activity to prevent proteolysis of the protein whilst maintaining the chaperone activity to allow correct folding and transportation of the protein in the host cell.

The skilled person would easily be able to test secreted protein to see if the protein is correctly folded using methods well known in the art, such as protein G HPLC, circular dichroism, NMR, X-Ray crystallography and epitope affinity measurement methods.

In these embodiments, one or more cells according to the present invention may have improved cell growth compared to cells carrying a mutated knockout DegP gene preventing DegP expression. Without wishing to be bound by theory improved cell growth may be exhibited due to the DegP protease retaining chaperone activity which may increase capacity of the cell to process all proteins which require chaperone activity. Accordingly, the production of correctly folded proteins necessary for the cell's growth and reproduction may be increased in one or more of the cells of the present invention compared to cells carrying a DegP knockout mutation thereby improving the cellular pathways regulating growth. Further, known DegP protease deficient strains are generally temperature-sensitive and do not typically grow at temperatures higher than about 28° C. However, the cells according to the present invention are not temperature-sensitive and may be grown at temperatures of 28° C. or higher, including temperatures of approximately 30° C. to approximately 37° C., which are typically used for industrial scale production of proteins from bacteria.

In certain embodiments of the present invention the recombinant gram-negative bacterial cell comprises a knockout mutated ptr gene. As used herein, "ptr gene" means a gene encoding Protease III, a protease which degrades high molecular weight proteins. The sequence of the non-mutated ptr gene is shown in SEQ ID NO: 4 and the sequence of the non-mutated Protease III protein is shown in SEQ ID NO: 5.

In certain embodiments of the present invention the recombinant gram-negative bacterial cell comprises a knockout mutated Tsp gene. As used herein, "Tsp gene" means a gene encoding protease Tsp (also known as Prc) which is a periplasmic protease capable of acting on Penicillin-binding protein-3 (PBP3) and phage tail proteins. The sequence of the non-mutated Tsp gene is show in SEQ ID NO: 1 and the sequence of the non-mutated Tsp protein is shown in SEQ ID NO: 2.

In the first aspect of the present invention, reference to the mutated ptr gene or mutated ptr gene encoding Protease III, refers to either a mutated ptr gene encoding a Protease III protein having reduced protease activity or a knockout mutated ptr gene, unless otherwise indicated.

In the first aspect of the present invention, reference to the mutated Tsp gene or mutated Tsp gene encoding Tsp, refers to either a mutated Tsp gene encoding a Tsp protein having reduced protease activity or a knockout mutated Tsp gene, unless otherwise indicated.

In the first aspect of the present invention the expressions "mutated ptr gene encoding a Protease III protein having reduced protease activity" and "mutated Tsp gene encoding a Tsp protein having reduced protease activity" in the context of the present invention means that the mutated ptr gene or the mutated Tsp gene does not have the full protease activity compared to the wild-type non-mutated ptr gene or Tsp gene.

In the first aspect of the present invention, preferably, the mutated ptr gene encodes a Protease III having 50% or less, 40% or less, 30% or less, 20% or less, 10% or less or 5% or less of the protease activity of a wild-type non-mutated Protease III protein. More preferably, the mutated ptr gene encodes a Protease III protein having no protease activity. In this embodiment the cell is not deficient in chromosomal ptr i.e. the ptr gene sequence has not been deleted or mutated to prevent expression of any form of Protease III protein.

Any suitable mutation may be introduced into the ptr gene in order to produce a Protease III protein having reduced protease activity. The protease activity of a Protease III protein expressed from a gram-negative bacterium may be easily tested by a person skilled in the art by any suitable method in the art.

In the first aspect of the present invention, preferably, the mutated Tsp gene encodes a Tsp protein having 50% or less, 40% or less, 30% or less, 20% or less, 10% or less or 5% or less of the protease activity of a wild-type non-mutated Tsp protein. More preferably, the mutated Tsp gene encodes a Tsp protein having no protease activity. In this embodiment the cell is not deficient in chromosomal Tsp i.e. the Tsp gene sequence has not been deleted or mutated to prevent expression of any form of Tsp protein.

Any suitable mutation may be introduced into the Tsp gene in order to produce a protein having reduced protease activity. The protease activity of a Tsp protein expressed from a gram-negative bacterium may be easily tested by a person skilled in the art by any suitable method in the art, such as the method described in Keiler et al (Identification of Active Site Residues of the Tsp Protease* THE JOURNAL OF BIOLOGICAL CHEMISTRY Vol. 270, No. 48, Issue of December 1, pp. 28864-28868, 1995 Kenneth C. Keiler and Robert T. Sauer) wherein the protease activities of Tsp was tested.

Tsp has been reported in Keiler et al (supra) as having an active site comprising residues 5430, D441 and K455 and residues G375, G376, E433 and T452 are important for maintaining the structure of Tsp. Keiler et al (supra) reports findings that the mutated Tsp genes S430A, D441A, K455A, K455H, K455R, G375A, G376A, E433A and T452A had no detectable protease activity. It is further reported that the mutated Tsp gene S430C displayed about 5-10% wild-type activity. Accordingly, the Tsp mutation to produce a protein having reduced protease activity may comprise a mutation, such as a missense mutation to one or more of residues 5430, D441, K455, G375, G376, E433 and T452. Preferably the Tsp mutation to produce a protein having reduced protease activity may comprise a mutation, such as a missense mutation to one, two or all three of the active site residues 5430, D441 and K455.

According the mutated Tsp gene may comprise:
a mutation to 5430; or
a mutation to D441; or
a mutation to K455; or
a mutation to 5430 and D441; or
a mutation to 5430 and K455; or
a mutation to D441 and K455; or
a mutation to 5430, D441 and K455.

One or more of 5430, D441, K455, G375, G376, E433 and T452 may be mutated to any suitable amino acid which results in a protein having reduced protease activity. Examples of suitable mutations are S430A, S430C, D441A, K455A, K455H, K455R, G375A, G376A, E433A and T452A. The mutated Tsp gene may comprise one, two or three mutations to the active site residues, for example the gene may comprise:
S430A or S430C; and/or
D441A; and/or
K455A or K455H or K455R.

Preferably, the Tsp gene comprises the point mutation S430A or S430C.

The present invention also provides a recombinant gram-negative bacterial cell comprising a mutated Tsp gene, wherein the mutated Tsp gene encodes a Tsp protein having reduced protease activity, wherein the Tsp gene comprise a mutation, such as a missense mutation to one or more of residues 5430, D441, K455, G375, G376, E433 and T452, as discussed above.

In the first aspect of the present invention the expression "knockout mutated ptr gene" and "knockout mutated Tsp gene" in the context of the present invention means that the gene comprises one or more mutations thereby causing no expression of the protein encoded by the gene to provide a cell deficient in the protein encoded by the knockout mutated gene. The knockout gene may be partially or completely transcribed but not translated into the encoded protein.

In the first aspect of the present invention, the knockout mutated ptr gene and/or knockout mutated Tsp gene may be mutated in any suitable way, for example by one or more deletion, insertion, point, missense, nonsense and frameshift mutations, to cause no expression of the protein. For example, the gene may be knocked out by insertion of a foreign DNA sequence, such as an antibiotic resistance marker, into the gene coding sequence.

In a preferred embodiment of the first aspect of the present invention the gene is not mutated by insertion of a foreign DNA sequence, such as an antibiotic resistance marker, into the gene coding sequence. Preferably the Tsp gene and/or Protease III gene comprise a mutation to the gene start codon and/or one or more stop codons positioned downstream of the gene start codon and upstream of the gene stop codon thereby preventing expression of the Tsp protein and/or Protease III protein.

The cell according to the second aspect of the present invention comprises Tsp and/or Protease III knockout mutations where the Tsp gene and/or Protease III gene comprise a mutation to the gene start codon and/or one or more stop codons positioned downstream of the gene start codon and upstream of the gene stop codon thereby preventing expression of the Tsp protein and/or Protease III protein.

A mutation to the target knockout gene start codon causes loss of function of the start codon and thereby ensures that the target gene does not comprise a suitable start codon at the start of the coding sequence. The mutation to the start codon may be a missense mutation of one, two or all three of the nucleotides of the start codon. Alternatively or additionally the start codon may be mutated by an insertion or deletion frameshift mutation.

The ptr gene and Tsp gene each comprise an ATG start codon. If the gene comprises more than one suitably positioned start codon, as found in the Tsp gene where two ATG codons are present at the 5' end of the coding sequence, one or both of the ATG codons may be mutated by a missense mutation.

In a preferred embodiment the ptr gene is mutated to change the ATG start codon to ATT, as shown in FIG. 1a. In a preferred embodiment the Tsp gene is mutated at the second ATG codon (codon 3) to TCG, as shown in FIG. 1b.

The knockout mutated ptr gene and/or the knockout mutated Tsp gene may alternatively or additionally comprise one or more stop codons positioned downstream of the gene start codon and upstream of the gene stop codon. Preferably the knockout mutated ptr gene and/or the knockout mutated Tsp gene comprise both a missense mutation to the start codon and one or more inserted stop codons.

The one or more inserted stop codons are preferably in-frame stop codons. However the one or more inserted stop codons may alternatively or additionally be out-of-frame stop codons. One or more out-of-frame stop codons may be required to stop translation where an out-of-frame start codon is changed to an in-frame start codon by an insertion or deletion frameshift mutation. The one or more stop codons may be introduced by any suitable mutation including a nonsense point mutation and a frameshift mutation. The one or more stop codons are preferably introduced by a frameshift mutation and/or an insertion mutation, preferably by replacement of a segment of the gene sequence with a sequence comprising a stop codon. For example an Ase I restriction site may be inserted, which comprises the stop codon TAA.

In a preferred embodiment the ptr gene is mutated to insert an in-frame stop codon by insertion of an Ase I restriction site, as shown in FIG. 1a.

In a preferred embodiment the Tsp gene is mutated to delete "T" from the fifth codon thereby causing a frameshift resulting in stop codons at codons 11 and 16, as shown in FIG. 1b. In a preferred embodiment the Tsp gene is mutated to insert an Ase I restriction site to create a third in-frame stop codon at codon 21, as shown in FIG. 1b.

In a preferred embodiment the knockout mutated ptr gene has the DNA sequence of SEQ ID NO: 6. The mutations which have been made in the knockout mutated ptr gene sequence of SEQ ID NO: 6 are shown in FIG. 1a.

In a preferred embodiment the knockout mutated Tsp gene has the DNA sequence of SEQ ID NO: 3, which includes the 6 nucleotides ATGAAT upstream of the start codon. The mutations which have been made in the knockout mutated Tsp sequence of SEQ ID NO: 3 are shown in FIG. 1b. In one embodiment the mutated Tsp gene has the DNA sequence of nucleotides 7 to 2048 of SEQ ID NO: 3.

The above described knockout mutations are advantageous because they cause minimal or no disruption to the chromosomal DNA upstream or downstream of the target knockout gene site and do not require the insertion and retention of foreign DNA, such as antibiotic resistance markers, which may affect the cell's suitability for expressing a protein of interest, particularly therapeutic proteins. Accordingly, one or more of the cells according to the present invention may exhibit improved growth characteristics and/or protein expression compared to cells wherein the protease gene has been knocked out by insertion of foreign DNA into the gene coding sequence.

Many genetically engineered mutations including knockout mutations involve the use of antibiotic resistance markers which allow the selection and identification of successfully mutated cells. However, as discussed above, there are a number of disadvantages to using antibiotic resistance markers.

A further embodiment of the present invention overcomes the above disadvantages of using antibiotic resistance markers wherein the mutated protease genes selected from one or more of a mutated DegP gene encoding a DegP protein having chaperone activity but not protease activity; a mutated ptr gene encoding Protease III; and a mutated Tsp gene encoding protease Tsp, are mutated to comprise one or more restriction marker sites. The restriction sites are genetically engineered into the gene and are non-naturally occurring. The restriction marker sites are advantageous because they allow screening and identification of correctly modified cells which comprise the required chromosomal mutations. Cells which have been modified to carry one or more of the mutated protease genes may be analyzed by PCR of genomic DNA from cell lysates using oligonucleotide pairs designed to amplify a region of the genomic DNA comprising a non-naturally occurring restriction marker site. The amplified DNA may then be analyzed by agarose gel electrophoresis before and after incubation with a suitable restriction enzyme capable of digesting the DNA at the non-naturally occurring restriction marker site. The presence of DNA fragments after incubation with the restriction enzyme confirms that the cells have been successfully modified to carry the one or more mutated protease genes.

In the embodiment wherein the knockout mutated ptr gene has the DNA sequence of SEQ ID NO: 6, the oligonucleotide primer sequences shown in SEQ ID NO: 17 and SEQ ID NO: 18 may be used to amplify the region of the DNA comprising the non-naturally occurring Ase I restriction site from the genomic DNA of transformed cells. The amplified genomic DNA may then be incubated with Ase I restriction enzyme and analyzed by gel electrophoresis to confirm the presence of the mutated ptr gene in the genomic DNA.

In the embodiment wherein the knockout mutated Tsp gene has the DNA sequence of SEQ ID NO: 3 or nucleotides 7 to 2048 of SEQ ID NO:3, the oligonucleotide primer sequences shown in SEQ ID NO: 15 and SEQ ID NO:16 may be used to amplify the region of the DNA comprising the non-naturally occurring Ase I restriction site from the genomic DNA of transformed cells. The amplified genomic DNA may then be incubated with Ase I restriction enzyme and analyzed by gel electrophoresis to confirm the presence of the mutated Tsp gene in the genomic DNA.

In the embodiment wherein the mutated DegP gene has the DNA sequence of SEQ ID NO: 9, the oligonucleotide primer sequences shown in SEQ ID NO: 19 and SEQ ID NO: 20 may be used to amplify the region of the DNA comprising the non-naturally occurring Ase I restriction site from the genomic DNA of transformed cells. The amplified genomic DNA may then be incubated with Ase I restriction enzyme and analyzed by gel electrophoresis to confirm the presence of the mutated DegP gene in the genomic DNA.

The one or more restriction sites may be introduced by any suitable mutation including by one or more deletion, insertion, point, missense, nonsense and frameshift mutations. A restriction site may be introduced by the mutation of the start codon and/or mutation to introduce the one or more stop codons, as described above. This embodiment is advantageous because the restriction marker site is a direct and unique marker of the knockout mutations introduced.

A restriction maker site may be inserted which comprises an in-frame stop codon, such as an Ase I restriction site. This is particularly advantageous because the inserted restriction site serves as both a restriction marker site and a stop codon to prevent full transcription of the gene coding sequence. For example, in the embodiment wherein a stop codon is introduced to the ptr gene by introduction of an Ase I site, this also creates a restriction site, as shown in FIG. 1a. For example, in the embodiment wherein a stop codon is introduced to the Tsp gene at codon 21 by introduction of an Ase I site, this also creates a restriction site, as shown in FIG. 1b.

A restriction marker site may be inserted by the mutation to the start codon and optionally one or more further point mutations. In this embodiment the restriction marker site is preferably an EcoR I restriction site. This is particularly advantageous because the mutation to the start codon also creates a restriction marker site. For example, in the embodiment wherein the start codon of the ptr gene is changed to ATT, this creates an EcoR I marker site, as shown in FIG. 1a. For example, in the embodiment wherein the start codon (codon 3) of the Tsp gene is changed from ATG to TCG, as shown in FIG. 1b, a further point mutation of codon 2 from AAC to AAT and mutation of codon 3 ATG to TCG creates an EcoR I restriction marker site, as shown in FIG. 1b.

In the DegP gene, a marker restriction site may be introduced using silent codon changes. For example, an Ase I site may be used as a silent restriction marker site, wherein the TAA stop codon is out-of-frame, as shown in FIG. 1c.

In the embodiments of the present invention, wherein the ptr gene and/or the Tsp gene are mutated to encode a Protease III or Tsp having reduced protease activity, one or more marker restriction site may be introduced using silent codon changes.

The recombinant gram-negative bacterial cell according to the present invention may be produced by any suitable means. The skilled person knows of suitable techniques which may be used to replace a chromosomal gene sequence with a mutated gene sequence. Suitable vectors may be employed which allow integration into the host chromosome by homologous recombination.

Suitable gene replacement methods are described, for example, in Hamilton et at (New Method for Generating Deletions and Gene Replacements in *Escherichia coli*, Hamilton C. M. et al., Journal of Bacteriology September 1989, Vol. 171, No. 9 p 4617-4622), Skorupski et at (Positive selection vectors for allelic exchange, Skorupski K and Taylor R. K., Gene, 1996, 169, 47-52), Kiel et at (A general method for the construction of *Escherichia coli* mutants by homologous recombination and plasmid segregation, Kiel J. A. K. W. et al, Mol Gen Genet 1987, 207:294-301), Blomfield et at (Allelic exchange in *Escherichia coli* using the *Bacillus subtilis* sacB gene and a temperature sensitive pSC101 replicon, Blomfield I. C. et al., Molecular Microbiology 1991, 5(6), 1447-1457) and Ried et al. (An nptl-sacB-sacR cartridge for constructing directed, unmarked mutations in Gram-negative bacteria by marker exchange-eviction mutagenesis, Ried J. L. and Collmer A., Gene 57 (1987) 239-246). A suitable plasmid which enables homologous recombination/replacement is the pKO3 plasmid (Link et al., 1997, Journal of Bacteriology, 179, 6228-6237).

Successfully mutated strains may be identified using methods well known in the art including colony PCR DNA sequencing and colony PCR restriction enzyme mapping.

In the embodiment wherein the cell comprises two or three of the mutated protease genes, the mutated protease may be introduced into the gram-negative bacterium on the same or different vectors.

In one embodiment the present invention provides a mutant *E. coli* cell strain MXE001 having genotype ΔTsp and deposited on 21 May 2009 at the National Collection of Type Cultures, HPA, United Kingdom, under Accession number NCTC13444.

In a further embodiment the present invention provides a mutant *E. coli* cell strain MXE002 having genotype Δptr and deposited on 21 May 2009 at the National Collection of Type Cultures, HPA, United Kingdom, under Accession number NCTC13445.

In one embodiment the present invention provides a mutant *E. coli* cell strain MXE003 having genotype DegP S210A and deposited on 21 May 2009 at the National Collection of Type Cultures, HPA, United Kingdom, under Accession number NCTC13446.

In a further embodiment the present invention provides a mutant *E. coli* cell strain MXE004 having genotype ΔTsp Δptr, and deposited on 21 May 2009 at the National Collection of Type Cultures, HPA, United Kingdom, under Accession number NCTC13447.

In one embodiment the present invention provides a mutant *E. coli* cell strain MXE005 having genotype ΔTsp, DegP S210A and deposited on 21 May 2009 at the National Collection of Type Cultures, HPA, United Kingdom, under Accession number NCTC13448.

In a further embodiment the present invention provides a mutant *E. coli* cell strain MXE006 having genotype Δptr, DegP S210A and deposited on 21 May 2009 at the National Collection of Type Cultures, HPA, United Kingdom, under Accession number NCTC13449.

In one embodiment the gram-negative bacterial cell according to the present invention does not carry a knockout mutated ompT gene, such as being deficient in chromosomal ompT. In one embodiment the cell according to the present invention does not carry any further knockout mutated protease genes apart from the knockout mutated ptr gene and/or the knockout mutated Tsp gene.

The cell according to the present invention may further comprise a polynucleotide sequence encoding a protein of interest. The polynucleotide sequence encoding the protein of interest may be exogenous or endogenous. The polynucleotide sequence encoding the protein of interest may be integrated into the host's chromosome or may be non-integrated in a vector, typically a plasmid.

In one embodiment the cell according to the present invention expresses a protein of interest. "Protein of interest" in the context of the present specification is intended to refer to polypeptide for expression, usually a recombinant polypeptide. However, the protein of interest may be an endogenous protein expressed from an endogenous gene in the host cell.

As used herein, a "recombinant polypeptide" refers to a protein that is constructed or produced using recombinant DNA technology. The protein of interest may be an exogenous sequence identical to the endogenous protein or a mutated version thereof, for example with attenuated biological activity, or fragment thereof, expressed from an exogenous vector. Alternatively, the protein of interest may be a heterologous protein, not normally expressed by the host cell.

The protein of interest may be any suitable protein including a therapeutic, prophylactic or diagnostic protein.

In one embodiment the protein of interest is useful in the treatment of diseases or disorders including inflammatory diseases and disorders, immune disease and disorders, fibrotic disorders and cancers.

The term "inflammatory disease" or "disorder" and "immune disease or disorder" includes rheumatoid arthritis, psoriatic arthritis, still's disease, Muckle Wells disease, psoriasis, Crohn's disease, ulcerative colitis, SLE (Systemic Lupus Erythematosus), asthma, allergic rhinitis, atopic dermatitis, multiple sclerosis, vasculitis, Type I diabetes mellitus, transplantation and graft-versus-host disease.

The term "fibrotic disorder" includes idiopathic pulmonary fibrosis (IPF), systemic sclerosis (or scleroderma), kidney fibrosis, diabetic nephropathy, IgA nephropathy, hypertension, end-stage renal disease, peritoneal fibrosis (continuous ambulatory peritoneal dialysis), liver cirrhosis, age-related macular degeneration (ARMD), retinopathy, cardiac reactive fibrosis, scarring, keloids, burns, skin ulcers, angioplasty, coronary bypass surgery, arthroplasty and cataract surgery.

The term "cancer" includes a malignant new growth that arises from epithelium, found in skin or, more commonly, the lining of body organs, for example: breast, ovary, prostate, lung, kidney, pancreas, stomach, bladder or bowel. Cancers tend to infiltrate into adjacent tissue and spread (metastasise) to distant organs, for example: to bone, liver, lung or the brain.

The protein may be a proteolytically-sensitive polypeptide, i.e. proteins that are prone to be cleaved, susceptible to cleavage, or cleaved by one or more gram-negative bacterial, such as E. coli, proteases, either in the native state or during secretion. In one embodiment the protein of interest is proteolytically-sensitive to a protease selected from DegP, Protease III and Tsp. In one embodiment the protein of interest is proteolytically-sensitive to the proteases DegP and Protease III. In one embodiment the protein of interest is proteolytically sensitive to the proteases DegP and Tsp. In one embodiment the protein of interest is proteolytically-sensitive to the proteases Tsp and Protease III. In one embodiment the protein of interest is proteolytically sensitive to the proteases DegP, Protease III and Tsp.

Preferably the protein is a eukaryotic polypeptide.

The protein of interest expressed by the cells according to the invention may, for example be an immunogen, a fusion protein comprising two heterologous proteins or an antibody. Antibodies for use as the protein of interest include monoclonal, multi-valent, multi-specific, humanized, fully human or chimeric antibodies. The antibody can be from any species but is preferably derived from a monoclonal antibody, a human antibody, or a humanized fragment. The antibody can be derived from any class (e.g. IgG, IgE, IgM, IgD or IgA) or subclass of immunoglobulin molecule and may be obtained from any species including for example mouse, rat, shark, rabbit, pig, hamster, camel, llama, goat or human. Parts of the antibody fragment may be obtained from more than one species for example the antibody fragments may be chimeric. In one example the constant regions are from one species and the variable regions from another.

The antibody may be a complete antibody molecule having full length heavy and light chains or a fragment thereof, e.g. VH, VL, VHH, Fab, modified Fab, Fab', F(ab')$_2$, Fv, scFv fragment, Fab-Fv, or a dual specificity antibody, such as a Fab-dAb, as described in PCT/GB2008/003331.

The antibody may be specific for any target antigen. The antigen may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD40L, CD45, CDW52, CD69, CD134 (OX40), ICOS, BCMP7, CD137, CD27L, CDCP1, CSF1 or CSF1-Receptor, DPCR1, DPCR1, dudulin2, FI120584, FI140787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, KDR and VEGF, and where appropriate, receptors thereof Soluble antigens include interleukins such as IL-1, IL-2, IL-3, IL-4, IL-5, IL-6, IL-8, IL-12, IL-13, IL-14, IL-16 or IL-17, such as IL17A and/or IL17F, viral antigens for example respiratory syncytial virus or cytomegalovirus antigens, immunoglobulins, such as IgE, interferons such as interferon α, interferon β or interferon γ, tumour necrosis factor TNF (formerly known as tumour necrosis factor-α), tumor necrosis factor-β, colony stimulating factors such as G-CSF or GM-CSF, and platelet derived growth factors such as PDGF-α, and PDGF-β and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment, the antibody may be used to functionally alter the activity of the antigen of interest. For example, the antibody may neutralize, antagonize or agonise the activity of said antigen, directly or indirectly.

In a preferred embodiment the protein of interest expressed by the cells according to the present invention is an anti-TNF antibody, more preferably an anti-TNF Fab', as described in WO01/094585 (the contents of which are incorporated herein by reference).

Preferably the antibody molecule has specificity for human TNF (formerly known as TNFα), wherein the light chain comprises the light chain variable region of SEQ ID NO: 11 and the heavy chain comprises the heavy chain variable region of SEQ ID NO: 12. Preferably the antibody molecule having specificity for human TNF is a Fab' and has a light chain sequence comprising or consisting of SEQ ID NO: 13 and a heavy chain sequence comprising or consisting of SEQ ID NO: 14.

The inventors of the present invention have surprisingly discovered that Fab yield may be improved by expression in one or more cells according to the present invention. Without wishing to be bound by theory, the mutated DegP gene used in the strains of the present invention having chaperone activity and reduced protease activity improves Fab yield because the chaperone activity of DegP facilitates the correct folding of Fab.

After expression, antibody fragments may be further processed, for example by conjugation to another entity such as an effector molecule.

The term effector molecule as used herein includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy. Effector molecular may be attached to the antibody or fragment thereof by any suitable method, for example an antibody fragment may be modified to attach at least one effector molecule as described in WO05/003171 or WO05/003170 (the contents of which are incorporated herein by reference). WO05/003171 or WO05/003170 also describe suitable effector molecules.

In one embodiment the antibody or fragment thereof, such as a Fab, is PEGylated to generate a product with the required properties, for example similar to the whole antibodies, if required. For example, the antibody may be a PEGylated anti-TNF-α Fab', as described in WO01/094585, preferably having attached to one of the cysteine residues at the C-terminal end of the heavy chain a lysyl-maleimide-derived group wherein each of the two amino groups of the lysyl residue has covalently linked to it a methoxypoly(ethyleneglycol) residue having a molecular weight of about 20,000 Da, such that the total average molecular weight of the methoxypoly(ethyleneglycol) residues is about 40,000 Da, more preferably the lysyl-maleimide-derived group is [1-[[[2-[[3-(2,5-dioxo-1-pyrrolidinyl)-1-oxopropyl]amino]ethyl]amino]-carbonyl]-1,5-pentanediyl]bis(iminocarbonyl).

The cell may also comprise further polynucleotide sequences encoding one or more further proteins of interest.

The polynucleotide encoding the protein of interest may be expressed as a fusion with another polypeptide, preferably a signal sequence or other polypeptide having a specific cleavage site at the N-terminus of the mature polypeptide. The heterologous signal sequence selected should be one that is recognized and processed by the host cell. For prokaryotic host cells that do not recognize and process the native or a eukaryotic polypeptide signal sequence, the signal sequence is substituted by a prokaryotic signal sequence. Suitable signal sequences include OmpA, PhoA, LamB, PelB, DsbA and DsbC.

In one embodiment an expression cassette is employed in the present invention to carry the polynucleotide encoding the protein of interest which typically comprises one or more protein coding sequences encoding one or more proteins of interest and one or more regulatory expression sequences. The one or more regulatory expression sequences may include a promoter. The one or more regulatory expression sequences may also include a 3' untranslated region such as a termination sequence. Suitable promoters are discussed in more detail below.

In one embodiment, the cell according to the present invention comprises a vector, such as plasmid. The vector preferably comprises one or more of the expression cassettes as defined above.

The vector for use in the present invention may be produced by inserting an expression cassette as defined above into a suitable vector. Alternatively, the regulatory expression sequences for directing expression of the polynucleotide sequence encoding a protein of interest may be contained in the vector and thus only the encoding region of the polynucleotide may be required to complete the vector.

Examples of vectors which may be employed to transform the host cell with a polynucleotide according to the invention include:
  a plasmid, such as pBR322 or PACYC 184, and/or
  a viral vector such as bacterial phage;
  a transposable genetic element such as a transposon.

Many forms of expression vector are available. Such vectors usually comprise a plasmid origin of DNA replication, an antibiotic selectable marker a promoter and transcriptional terminator separated by a multi-cloning site (expression cassette) and a DNA sequence encoding a ribosome binding site.

The promoters employed in the present invention can be linked to the relevant polynucleotide directly or alternatively be located in an appropriate position, for example in a vector such that when the relevant polypeptide is inserted the relevant promoter can act on the same. In one embodiment the promoter is located before the encoding portion of the polynucleotide on which it acts, for example a relevant promoter before each encoding portion of polynucleotide. "Before" as used herein is intended to imply that the promoter is located at the 5 prime end in relation to the encoding polynucleotide portion.

The promoters may be endogenous or exogenous to the host cells. Suitable promoters include Lac, tac, trp, PhoA, Ipp, Arab, Tet and T7.

One or more promoters employed may be inducible promoters.

Expression units for use in bacterial systems also generally contain a Shine-Dalgarno (S. D.) ribosome sequence operably linked to the DNA encoding the polypeptide of interest.

In the embodiments of the present invention wherein a polynucleotide sequence comprises two or more encoding sequences for two or more proteins of interest, for example an antibody light chain and antibody heavy chain, the polynucleotide sequence may comprise one or more internal ribosome entry site (IRES) sequences which allows translation initiation in the middle of an mRNA. An IRES sequence may be positioned between encoding polynucleotide sequences to enhance separate translation of the mRNA to produce the encoded polypeptide sequences.

The terminators may be endogenous or exogenous to the host cells. A suitable terminator is rrnB.

Further suitable transcriptional regulators including promoters and terminators and protein targeting methods may be found in "Strategies for Achieving High-Level Expression of Genes in *Escherichia coli*" Savvas C. Makrides, Microbiological Reviews, September 1996, p. 512-538.

Embodiments of the invention described herein with reference to the polynucleotide apply equally to alternative embodiments of the invention, for example vectors, expression cassettes and/or host cells comprising the components employed therein, as far as the relevant aspect can be applied to same.

According to a third aspect of the present invention there is provided a method for producing a recombinant protein of interest comprising expressing the recombinant protein of interest in a recombinant gram-negative bacterial cell as described above in the first or second aspect of the present invention.

The gram negative bacterial cell and protein of interest preferably employed in the method of the present invention are described in detail above.

When the polynucleotide encoding the protein of interest is exogenous the polynucleotide may be incorporated into the host cell using any suitable means known in the art. Typically, the polynucleotide is incorporated as part of an expression vector which is transformed into the cell. Accordingly, in one aspect the cell according to the present invention comprises an expression cassette comprising the polynucleotide encoding the protein of interest.

The polynucleotide sequence can be transformed into a cell using standard techniques, for example employing rubidium chloride, PEG or electroporation.

The method according to the present invention may also employ a selection system to facilitate selection of stable cells which have been successfully transformed with the polynucleotide encoding the protein of interest. The selection system typically employs co-transformation of a polynucleotide sequence encoding a selection marker. In one embodiment, each polynucleotide transformed into the cell further comprises a polynucleotide sequence encoding one or more selection markers. Accordingly, the transformation of the polynucleotide encoding the protein of interest and the one or more polynucleotides encoding the marker occurs together and the selection system can be employed to select those cells which produce the desired proteins.

Cells able to express the one or more markers are able to survive/grow/multiply under certain artificially imposed conditions, for example the addition of a toxin or antibiotic, because of the properties endowed by the polypeptide/gene or polypeptide component of the selection system incorporated therein (e.g. antibiotic resistance). Those cells that cannot express the one or more markers are not able to survive/grow/multiply in the artificially imposed conditions. The artificially imposed conditions can be chosen to be more or less vigorous, as required.

Any suitable selection system may be employed in the present invention. Typically the selection system may be based on including in the vector one or more genes that provides resistance to a known antibiotic, for example a tetracycline, chloramphenicol, kanamycin or ampicillin resistance gene. Cells that grow in the presence of a relevant antibiotic can be selected as they express both the gene that gives resistance to the antibiotic and the desired protein.

In one embodiment, the method according to the present invention further comprises the step of culturing the transformed cell in a medium to thereby express the protein of interest.

An inducible expression system or a constitutive promoter may be used in the present invention to express the protein of interest. Suitable inducible expression systems and constitutive promoters are well known in the art.

Any suitable medium may be used to culture the transformed cell. The medium may be adapted for a specific selection system, for example the medium may comprise an antibiotic, to allow only those cells which have been successfully transformed to grow in the medium.

The cells obtained from the medium may be subjected to further screening and/or purification as required. The method may further comprise one or more steps to extract and purify the protein of interest as required.

The polypeptide may be recovered from the strain, including from the cytoplasm, periplasm, or culture medium.

The specific method (s) used to purify a protein depends on the type of protein. Suitable methods include fractionation on immunoaffinity or ion-exchange columns; ethanol precipitation; reversed-phase HPLC; hydrophobic-interaction chromatography; chromatography on silica; chromatography on an ion-exchange resin such as S-SEPHAROSE and DEAE; chromatofocusing; ammonium-sulfate precipitation; and gel filtration.

Antibodies may be suitably separated from the culture medium and/or cytoplasm extract and/or periplasm extract by conventional antibody purification procedures such as, for example, protein A-Sepharose, protein G chromatography, protein L chromatograpy, thiophilic, mixed mode resins, Histag, FLAGTag, hydroxylapatite chromatography, gel electrophoresis, dialysis, affinity chromatography, Ammonium Sulphate, ethanol or PEG fractionation/precipitation, ion exchange membranes, expanded bed adsorption chromatography (EBA) or simulated moving bed chromatography.

The method may also include a further step of measuring the quantity of expression of the protein of interest and selecting cells having high expression levels of the protein of interest.

One or more method steps described herein may be performed in combination in a suitable container such as a bioreactor.

EXAMPLES

Example 1

Generation of Mutant E. coli Cell Strains

The host cell strain used was W3110 genotype: F– LAM– IN (rrnD-rrnE)1 rph1 (ATCC no. 27325).

W3110A, as shown in the figures, is a different batch of W3110.

The following mutant E. coli cell strains were generated using a gene replacement vector system using the pKO3 homologous recombination/replacement plasmid (Link et al., 1997, Journal of Bacteriology, 179, 6228-6237).

| Mutant E. coli Cell Strain | Genotype |
|---|---|
| MXE001 | ΔTsp |
| MXE004 | ΔTsp, Δprotease III |
| MXE005 | ΔTsp, DegP S210A |

Strain MXE001 was deposited on 21 May 2009 at the National Collection of Type Cultures, HPA, United Kingdom, under Accession number NCTC13444.

Strain MXE004 was deposited on 21 May 2009 at the National Collection of Type Cultures, HPA, United Kingdom, under Accession number NCTC13447.

Strain MXE005 was deposited on 21 May 2009 at the National Collection of Type Cultures, HPA, United Kingdom, under Accession number NCTC13448.

The Tsp, protease III and DegP integration cassettes were moved as Sal I, Not I restriction fragments into similarly restricted pKO3 plasmids.

The plasmid uses the temperature sensitive mutant of the pSC101 origin of replication (RepA) along with a chloramphenicol marker to force and select for chromosomal integration events. The sacB gene which encodes for levansucrase is lethal to E. coli grown on sucrose and hence (along with the chloramphenicol marker and pSC101 origin) is used to force and select for de-integration and plasmid curing events. This methodology had been described previously (Hamilton et al., 1989, Journal of Bacteriology, 171, 4617-4622 and Blomfield et al., 1991, Molecular Microbiology, 5, 1447-1457). The pKO3 system removes all selective markers from the host genome except for the inserted gene.

The following plasmids were constructed.

pMXE191 comprising the knockout mutated Tsp gene as shown in the SEQ ID NO: 3 comprising EcoR I and Ase I restriction markers.

pMXE192 comprising the knockout mutated Protease III gene as shown in the SEQ ID NO: 6 comprising EcoR I and Ase I restriction markers.

pMXE192 comprising the mutated DegP gene as shown in the SEQ ID NO: 9 comprising an Ase I.

These plasmids were then transformed into chemically competent E. coli W3110 cells prepared using the method found in Chung C T et al Transformation and storage of bacterial cells in the same solution. PNAS 86:2172-2175 (1989).

Day 1 40 µl of E. coli cells were mixed with (10 pg) 1 µl of pKO3 DNA in a chilled BioRad 0.2 cm electroporation cuvette before electroporation at 2500V, 25 µF and 200a 1000 µl of 2×PY was added immediately, the cells recovered by shaking at 250 rpm in an incubator at 30° C. for 1 hour. Cells were serially ⅒ diluted in 2×PY before 100 µl aliquots were plated out onto 2×PY agar plates containing chloramphenicol at 20 µg/ml prewarmed at 30° C. and 43° C. Plates were incubated overnight at 30° C. and 43° C.

Day 2 The number of colonies grown at 30° C. gave an estimate of the efficiency of electroporation whilst colonies that survive growth at 43° C. represent potential integration events. Single colonies from the 43° C. plate were picked and resuspended in 10 ml of 2×PY. 100 µl of this was plated out onto 2×PY agar plates containing 5% (w/v) sucrose prewarmed to 30° C. to generate single colonies. Plates were incubated overnight at 30° C.

Day 3 Colonies here represent potential simultaneous de-integration and plasmid curing events. If the de-integration and curing events happened early on in the growth, then the bulk of the colony mass will be clonal. Single colonies were picked and replica plated onto 2×PY agar that contained either chloramphenicol at 20 μg/ml or 5% (w/v) sucrose. Plates were incubated overnight at 30° C.

Day 4 Colonies that both grow on sucrose and die on chloramphenicol represent potential chromosomal replacement and plasmid curing events. These were picked and screened by PCR with a mutation specific oligonucleotide. Colonies that generated a positive PCR band of the correct size were struck out to produce single colonies on 2×PY agar containing 5% (w/v) sucrose and the plates were incubated overnight at 30° C.

Day 5 Single colonies of PCR positive, chloramphenicol sensitive and sucrose resistant E. coli were used to make glycerol stocks, chemically competent cells and act as PCR templates for a PCR reaction with 5' and 3' flanking oligos to generate PCR product for direct DNA sequencing using Taq polymerase.

Cell strains MXE001, MXE004 and MXE005 were tested to confirm successful modification of genomic DNA carrying one or more the mutated protease genes by PCR amplification of the region of each mutated protease gene comprising a non-naturally occurring Ase I restriction site, as shown in FIGS. 1a, 1b and 1c, using oligonucleotides primers. The amplified regions of the DNA were then analyzed by gel electrophoresis before and after incubation with Ase I restriction enzyme to confirm the presence of the non-naturally occurring Ase I restriction site in the mutated genes. This method was carried out as follows:

The following oligos were used to amplify, using PCR, genomic DNA from prepared E. coli cell lysates from MXE001, MXE004, MXE005, and W3110:

```
                                      (SEQ ID NO: 15)
6284 Tsp 3'       5'-GCATCATAATTTTCTTTTTACCTC-3'

(SEQ ID NO: 16)
6283 Tsp 5'       5'-GGGAAATGAACCTGAGCAAAACGC-3'

(SEQ ID NO: 17)
6362 Protease III 3'5'-GTGCCAGGAGATGCAGCAGCTTGC-3'

(SEQ ID NO: 18)
6361 Protease III 5'5'-TTTGCAGCCAGTCAGAAAGTG-3'

(SEQ ID NO: 19)
6282 DegP 5'      5'-CTGCCTGCGATTTTCGCCGGAACG-3'

(SEQ ID NO: 20)
6281 DegP 3'      5'-CGCATGGTACGTGCCACGATATCC-3'
```

The lysates were prepared by heating a single colony of cells for 10 minutes at 95° C. in 20 ul of 1×PCR buffer. The mixture was allowed to cool to room temperature then centrifugation at 13,200 rpm for 10 minutes. The supernatant was removed and labeled as 'cell lysate'.

Each strain was amplified using every pair of oligos' Tsp pair, Protease III pair and DegP pair.

The DNA was amplified using a standard PCR procedure.

| 5 ul | Buffer x10 (Roche) |
| 1 ul | dNTP mix (Roche, 10 mM mix) |
| 1.5 ul | 5' oligo (5 pmol) |
| 1.5 ul | 3' oligo (5 pmol) |
| 2 ul | Cell lysate |
| 0.5 ul | Taq DNA polymerase (Roche 5 U/ul) |
| 38.5 ul | H2O |

PCR Cycle.

| 94° C. | 1 minute |
| 94° C. | 1 minute) |
| 55° C. | 1 minute) repeated for 30 cycles |
| 72° C. | 1 minute) |
| 72° C. | 10 minutes |

Once the reactions were complete 25 ul was removed to a new microfuge tube for digestion with Ase I. To the 25 ul of PCR reaction 19 ul of H2O, 5 ul of buffer 3 (NEB), 1 ul of Ase I (NEB) was added, mixed and incubated at 37° C. for 2 hours.

To the remaining PCR reaction 5 ul of loading buffer (×6) was added and 20 ul was loaded onto a 0.8% TAE 200 ml agarose gel (Invitrogen) plus Ethidium Bromide (5 ul of 10 mg/ml stock) and run at 100 volts for 1 hour. 10 ul of size marker (Perfect DNA marker 0.1-12 Kb, Novagen) was loaded in the final lane.

Once the Ase I digestions were complete 10 ul of loading buffer (×6) was added and 20 ul was loaded onto a 0.8% TAE agarose gel (Invitrogen) plus Ethidium Bromide (5 ul of 10 mg/ml stock) and run at 100 volts for 1 hour. 10 ul of size marker (Perfect DNA marker 0.1-12 Kb, Novagen) was loaded in the final lane.

Both gels were visualized using UV transluminator.

All genomic fragments amplified showed the correct sized band of 2.8 Kb for Tsp, 1.8 Kb for protease III and 2.2K.b for DegP.

Following digestion with Ase I this confirmed the presence of the introduced Ase I sites in the protease deficient strains but not in the W3110 control.

MXE001: genomic DNA amplified using the Tsp primer set and the resulting DNA was digested with Ase I to produce 2.2 and 0.6 Kbps bands.

MXE004: genomic DNA amplified using the Tsp primer set and the protease III primer set and the resulting DNA was digested with Ase I to produce 2.2 and 0.6 Kbps bands (Tsp fragments) and 1.0 and 0.8 Kbps bands (Protease III fragments).

MXE005 genomic DNA amplified using the Tsp primer set and the DegP primer set and the resulting DNA was digested with Ase I to produce 2.2 and 0.6 Kbps bands (Tsp fragments) and 1.25 and 0.95 Kbps bands (DegP fragments).

W3110 PCR amplified DNA was not digested by Ase I restriction enzyme.

Plasmid pMXE117 (pTTO CDP870 or 40.4), an expression vector for the CDP870 Fab' (an anti-TNF Fab'), was constructed using conventional restriction cloning methodologies which can be found in Sambrook et at 1989, Molecular cloning: a laboratory manual. CSHL press, N.Y. The plasmid pMXE117 (pTTO CDP870 or 40.4) contained the following features; a strong tac promoter and lac operator sequence. The Fab light and heavy chain genes were transcribed as a single dicistronic message. DNA encoding the signal peptide from the E. coli OmpA protein was fused to the 5' end of both light and heavy chain gene sequences, which directed the translocation of the polypeptides to the E. coli periplasm.

Transcription was terminated using a dual transcription terminator rrnB t1t2. The lacIq gene encoded the constitutively expressed Lac I repressor protein. This repressed transcription from the tac promoter until de-repression was induced by the presence of allolactose or IPTG. The origin of replication used was p15A, which maintained a low copy number. The plasmid contained a tetracycline resistance gene for antibiotic selection.

pMXE117 was then transformed into chemically competent proteases deficient cells (strains MXE001, MXE004 and MXE005) and W3110 cells prepared using the method found in Chung C. T et at Transformation and storage of bacterial cells in the same solution. PNAS 86:2172-2175 (1989).

Example 2

Expression of an Anti-TNFα Fab' in Mutated E. coli Strains Using Shake Flask Cultures Strains MXE001, MXE004 and MXE005 were tested in a shake flask experiment comparing growth and expression of an anti-TNFα Fab' against W3110.

The shake flask experimental protocol used was performed as follows:

Preparation of Defined Medium Adapted Cells.

A single colony was picked into 5 ml 2×PY (1% phytone, Difco, 0.5% yeast extract, Difco, 0.5% NaCl) broth plus tetracycline (Sigma) at 10 ug/ml and grown overnight at 37° C. with shaking at 250 rpm. 100 ul of this overnight culture was used to inoculate 200 ml of chemically defined SM6E medium (described in Humphreys et al., 2002, *Protein Expression and Purification*, 26, 309-320) plus tetracycline at 10 ug/ml, grown overnight at 30° C. with shaking at 250 rpm. 100 ul of this second overnight culture was used to inoculate a 2nd 200 ml SM6E media flask plus tetracycline at 10 ug/ml. This was grown until the culture reached an OD600 of about 2. The cultures were centrifuged briefly to collect cells before being re-suspended in 100 ml of SM6E. Glycerol was added to a final concentration of 12.5% before storing aliquots of 'adapted cells' at −80° C.

200 ml Shake Flask Experiment

Shake flask cultures were initiated by addition of a 2 ml aliquot of thawed defined medium 'adapted cells' to 200 ml of SM6E media plus tetracycline 10 ug/ml. These where grown overnight at 30° C. with agitation at 250 rpm. Each strain being tested was grown in triplicate.

Cultures grown to 2.0 OD600 were induced for production of heterologous protein by the addition of IPTG to 200 uM. 1 ml culture samples were taken at 1 hr, 2 hr, 4 hr, 6 hr, 12 hr and 24 hrs and after centrifugation at 13,200 rpm for 5 minutes the cell pellet was resuspended in 200 ul of periplasmic extraction buffer (100 mM Tris.Cl/10 mM EDTA pH 7.4). Periplasmic extracts were agitated at 250 rpm over night at 30° C. The next day, the extracts were centrifuged for 10 minutes at 13,200 rpm, the supernatant decanted off and stored at −20° C. as 'periplasmic extract'. The spent cell pellet was discarded.

ELISA Quantification.

96 well ELISA plates were coated overnight at 4° C. with AB141 (rabbit anti-human CH1, UCB) at 2 µgml$^{-1}$ in PBS. After washing 3× with 300 ul of sample/conjugate buffer (PBS, BSA 0.2% (w/v), Tween 20 0.1% (v/v)), serial ½ dilutions of samples and standards were performed on the plate in 100 µl of sample/conjugate buffer, and the plate agitated at 250 r.p.m at room temperature for 1 hour. After washing 3× with 300 ul of wash buffer (PBS, Tween 20 0.1% (v/v)), 100 µl of the revealing antibody 6062 (rabbit anti-human kappa HRP conjugated, The Binding Site, Birmingham, U.K.) was added, after dilution at ¹⁄₁₀₀₀ in sample/conjugate buffer. The plate was then agitated at 250 r.p.m at room temperature for 1 hour. After washing with 3×300 ul of wash buffer, 100 µl of TMB substrate was added (50:50 mix of TMB solution (Calbiochem): dH$_2$O) and the A$_{630}$ recorded using an automated plate reader. The concentration of Fab' in the periplasmic extracts were calculated by comparison with purified Fab' standards of the appropriate isotype.

FIG. 2 shows growth of MXE005 and MXE001 compared to the wild type W3110.

Figure 3:
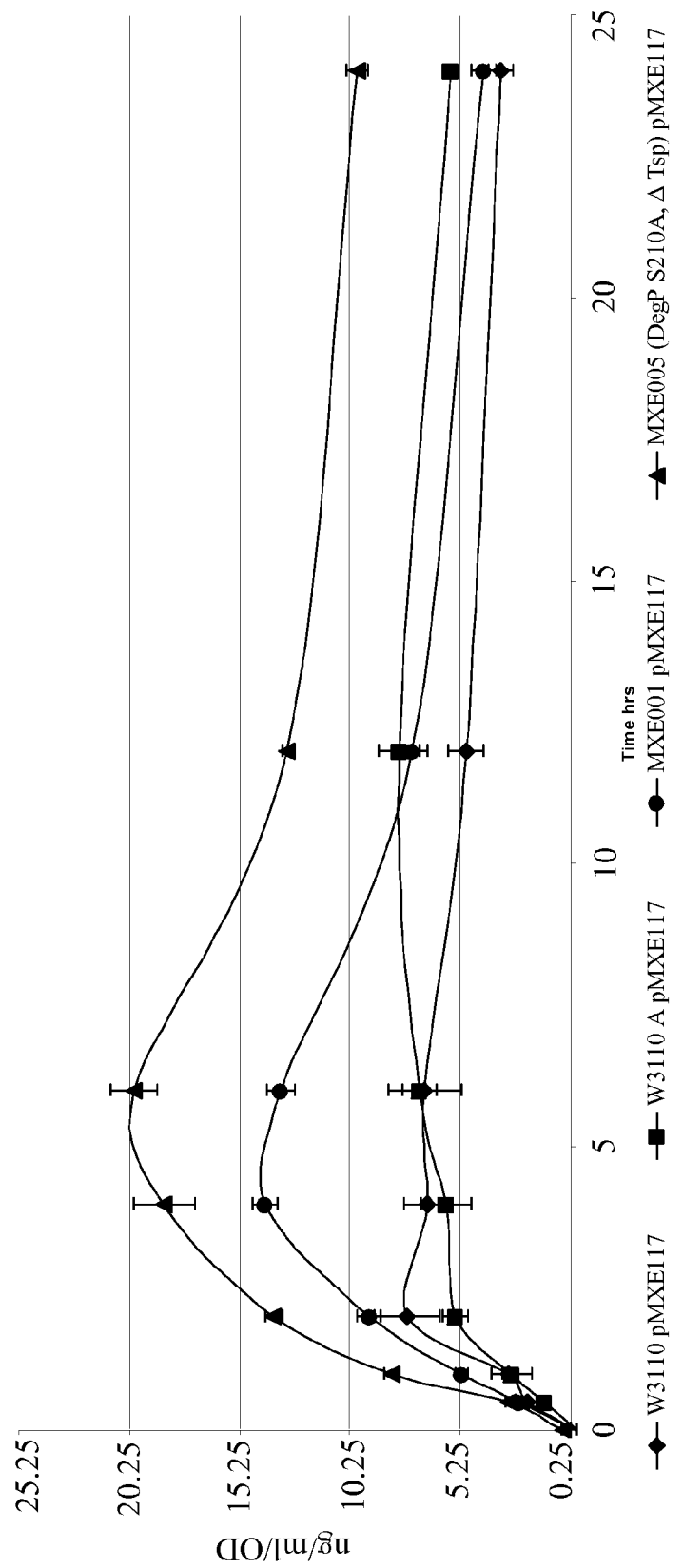
FIG. 3 shows the expression of a Fab' in MXE005 and MXE001 compared to wild type W3110.

FIG. 3 shows improved expression of the Fab' from MXE005 and MXE001 strains compared to the wild type W3110.

Figure 4:
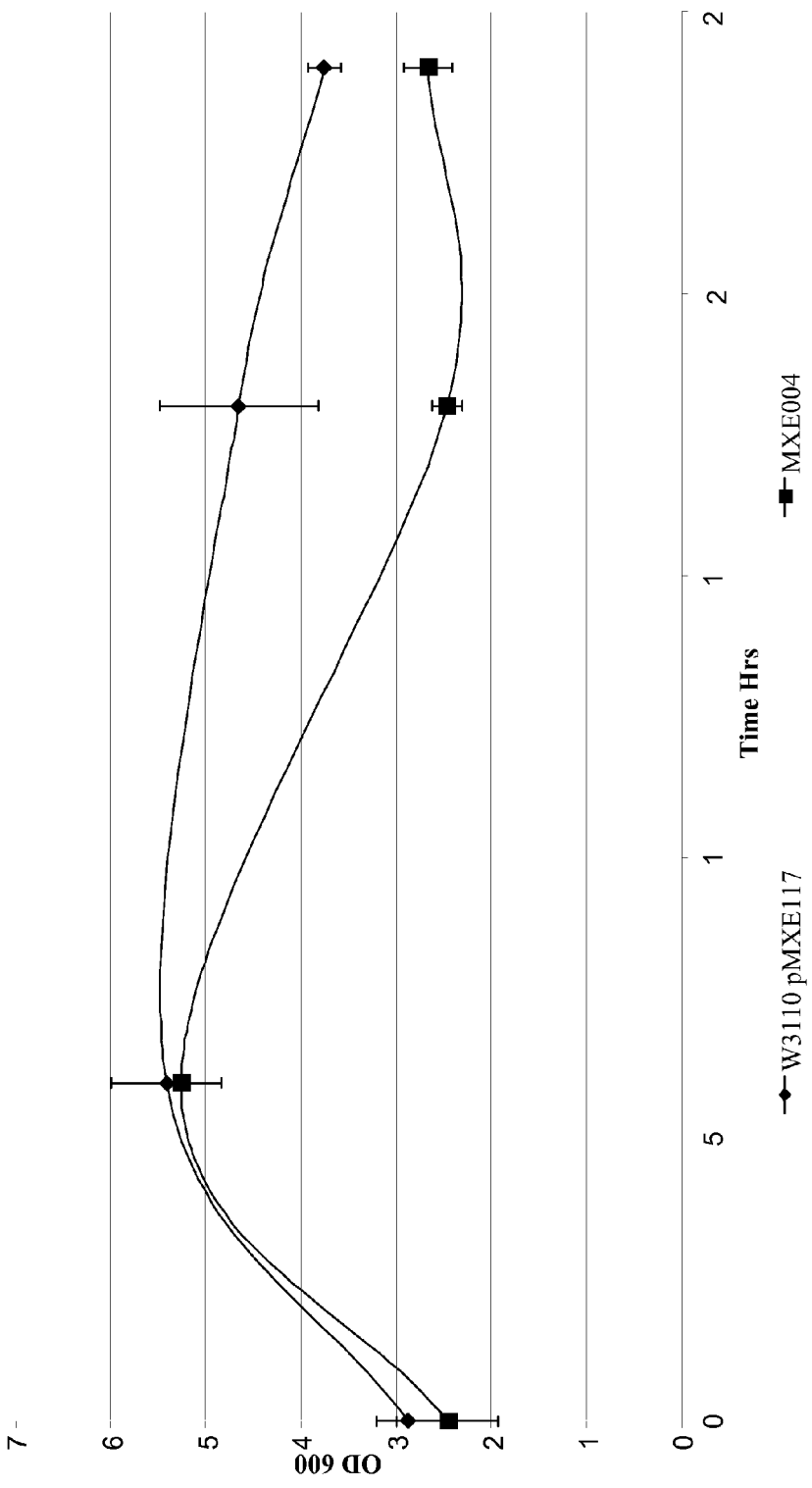
FIG. 4 shows the growth of *E. coli* strain MXE004 carrying a knockout mutated Tsp gene and a knockout mutated protease III compared to wild type W3110.
Figure 5:
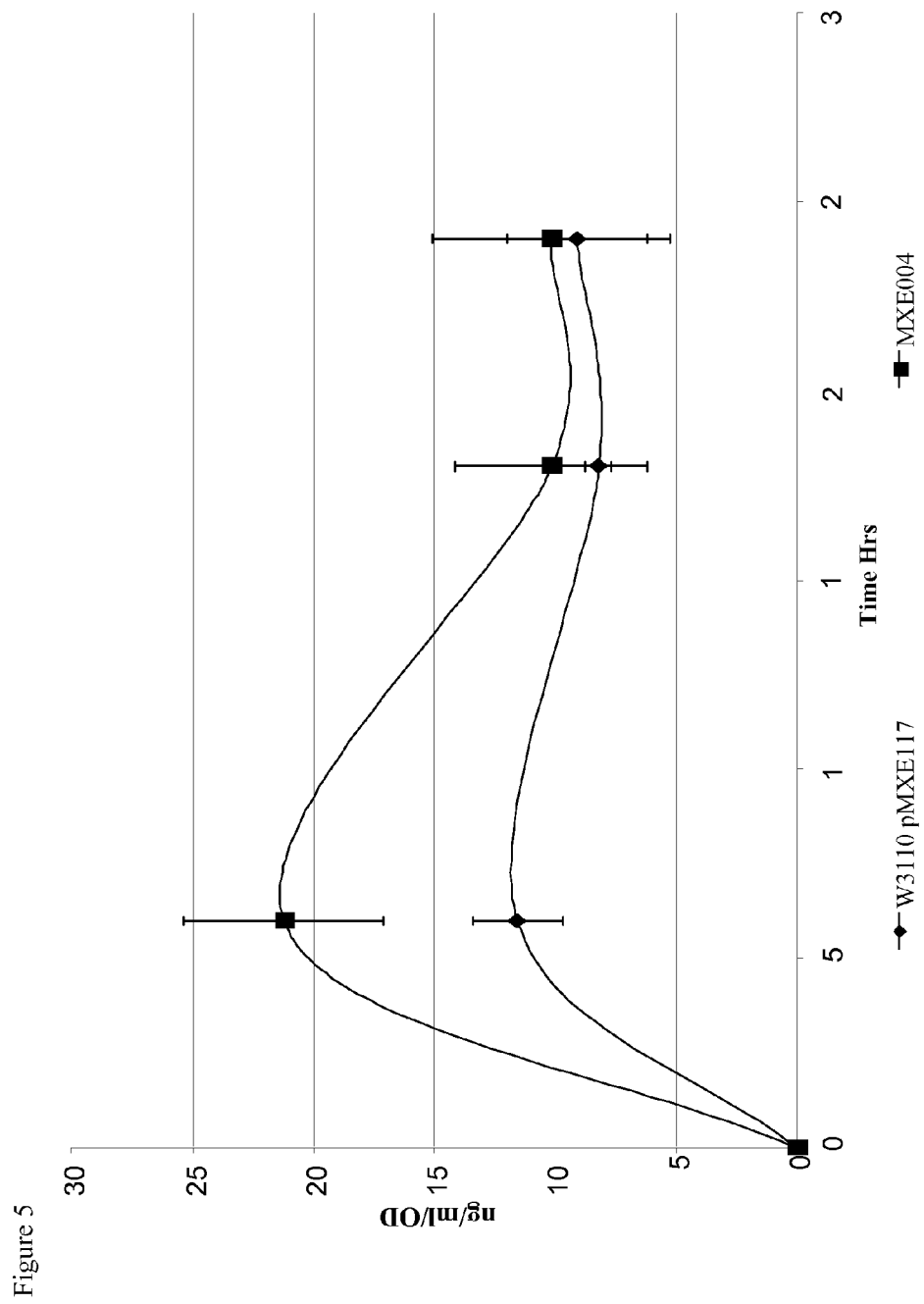
FIG. 5 shows the expression of a Fab' in MXE004 and W3110.

FIG. 4 shows the growth of MXE004 and W3110 and FIG. 5 shows expression of the Fab' in MXE004 and W3110 where it can be seen that the expression from MXE004 was higher than W3110.

Example 3

Expression of an Anti-mIL13 Mouse Fab in Mutated E. coli Strains Using Shake Flask Cultures Strains MXE001, MXE004, MXE005 and wild type W3110 cells were transformed with plasmid pMKC006 expressing a murinised anti-mIL13 Fab' and tested using the same shake flask method described in Example 2 except the experiment was stopped after 6 hours instead of 24 hours.

Figure 6:
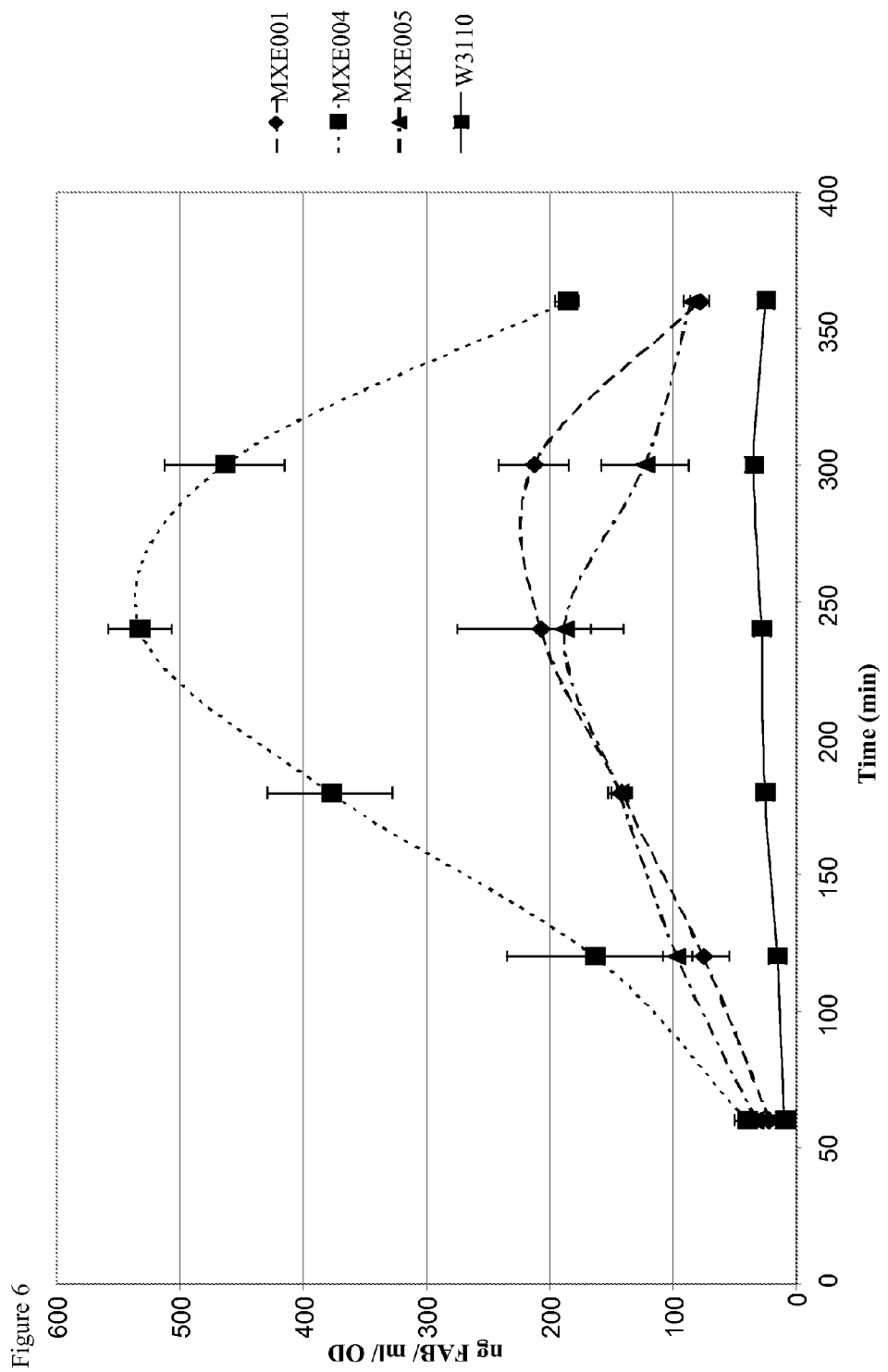
FIG. 6 shows the expression of a Fab in MXE001, MXE004, MXE005 and W3110.

FIG. 6 shows the expression of an anti-mIL-13 mouse Fab in MXE001, MXE004, MXE005 and W3110, where it can be seen that MXE001, MXE004 and MXE005 show higher Fab expression compared to W3110.

Example 4

Analysis of Light and Heavy Chain Expression from Mutated E. coli Strains

Periplasmic extracts from strain MXE005 and wild type W3110 cells transformed with plasmid pMXE117, from the shake flask experiment described in Example 2 and were tested using a surface Plasmon resonance binding assay performed using a BIAcore™ 2000 instrument (Pharmacia Biosensor AB, Uppsala, Sweden). The anti-TNFα Fab' was immobilised onto CM5 sensor chips using standard NHS/EDC chemistry. Residual NHS esters were inactivated with ethanolamine hydrochloride (1 M).

Fab' fragments were captured by either an immobilised monoclonal antiheavy chain or by an immobilised monoclonal anti-light chain antibody in separate flow cells. The presence of bound Fab' was revealed by binding of the complementary monoclonal antibody (anti-light chain or anti-heavy chain) in a second step. High levels of immobilised antibody ensure that measurements are performed under mass transport-limited conditions, where the contribution of the association rate constant to binding is low in comparison to the contribution made by the concentration of the Fab' in the sample. The solution phase monoclonal antibody used in the second step is passed over the surface at a high concentration so that binding is not limited by the association rate constant of this interaction.

Assembled Fab' fragments and correctly folded unassembled chains are both detected during the first capture step. Binding of the second antibody is only to an intact Fab' fragment. Therefore, analysis of the relative binding at the first and second stages reveals the presence of either excess unassembled light chain, or excess unassembled heavy chain in the Fab' sample and provides information on the stoichiometry of assembly.

Assays were performed in both configurations for each sample, and each sample was run in duplicate and in a randomised order.
(i) Where the concentration of assembled Fab' was to be determined by light chain capture, samples and standards zu at 10 gl/min) were injected over immobilised HP6053, followed by a second step in which HP6045 at 300 Rg/ml was passed over the surface in the solution phase.
(ii) Where the concentration of assembled Fab' was to be determined by heavy chain capture, samples and standards (10t at tOjuVmin) were injected over immobilised HP6045, followed by a second step in which HP6053 at 5001 lg/ml was passed over the surface in the solution phase. In both cases, the surface was regenerated with 10 gi of 30 mM HCl at 30 l/min.

The number of resonance units determined using the BIAevaluation 3.1 (Pharmacia Biosensor AB), was read against a standard curve.

Figure 7:
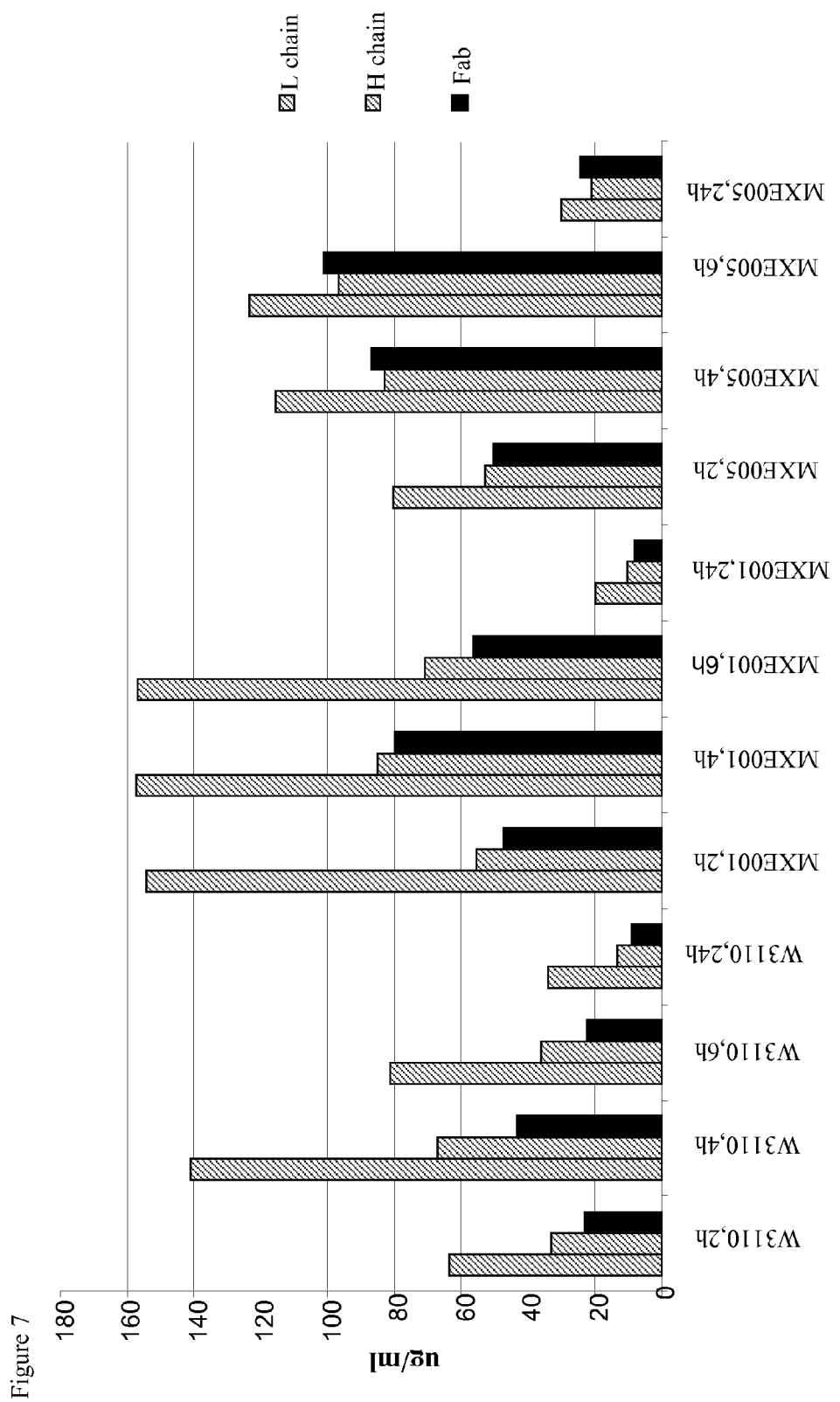
FIG. 7 shows the light chain (L chain), heavy chain (H chain) and Fab' expression during a fermentation experiment for MXE001, MXE005 and wild type W3110.

FIG. 7 shows the light chain (L chain), heavy chain (H chain) and Fab expression during the course of a fermentation run where a higher light chain, heavy chain and Fab' expression from MXE001 after 2 hours, 4 hours and 6 hours compared to W3110 is shown. FIG. 7 shows higher light chain after 6 hours from MXE005 compared to W3110 and higher Fab' expression from MXE005 after 2 hours, 4 hours and 6 hours compared to W3100.

Example 5

Analysis of Proteolysis Activity of Mutated *E. coli* Strains for Fab'

Periplasmic extracts from strains MXE001, MXE005 and wild type W3110 cells, transformed with plasmid pMXE117 from the Shake flask experiment in Example 2 were tested in a polyclonal western blot analysis comparing proteolysis of an anti-TNFα Fab' as follows:

12 ul of each periplasmic extract plus 4 ul of SDS-PAGE loading buffer (Invitrogen) was heated to 85° C. for 5 minutes, allowed to cool to 25° C. then centrifuged briefly before loading on to a pre prepared NuPAGE 4-12% Bis-Tris gel (Invitrogen). SeeBlue 2 size markers (Invitrogen) were used for molecular weight estimation. The gel was electrophoresed for 1 hour at 150V before transfer of proteins onto pre-wetted PVDF membrane (Invitrogen) using immunoblotting at 150 mA for 2 hours. The membrane was blocked for 1 hr in 'blocking buffer' (PBS, 3% (w/v) milk powder, 0.1% (v/v) Tween20 (Sigma)) with gentle agitation. A polyclonal rabbit anti-human Fab' sera (UCB) was applied at a dilution of 1 in 1000 in 5 mls of blocking buffer and incubated at room temperature for 1 hour with gentle agitation. The membrane was washed three times for 5 mins each with gentle agitation with blocking buffer. A secondary antibody (donkey anti-rabbit IgG HRP conjugated antibody (Jackson)) applied at a dilution of 1 in 5000 in blocking buffer and incubation at room temperature for 1 hour with gentle agitation. The membrane was washed four times for 5 minutes each with agitation firstly with blocking buffer followed by PBS, 0.1% Tween for two washes then PBS for the final wash. The blot was visualized using Metal Enhanced Dab substrate (Thermo Scientific).

Figure 8:
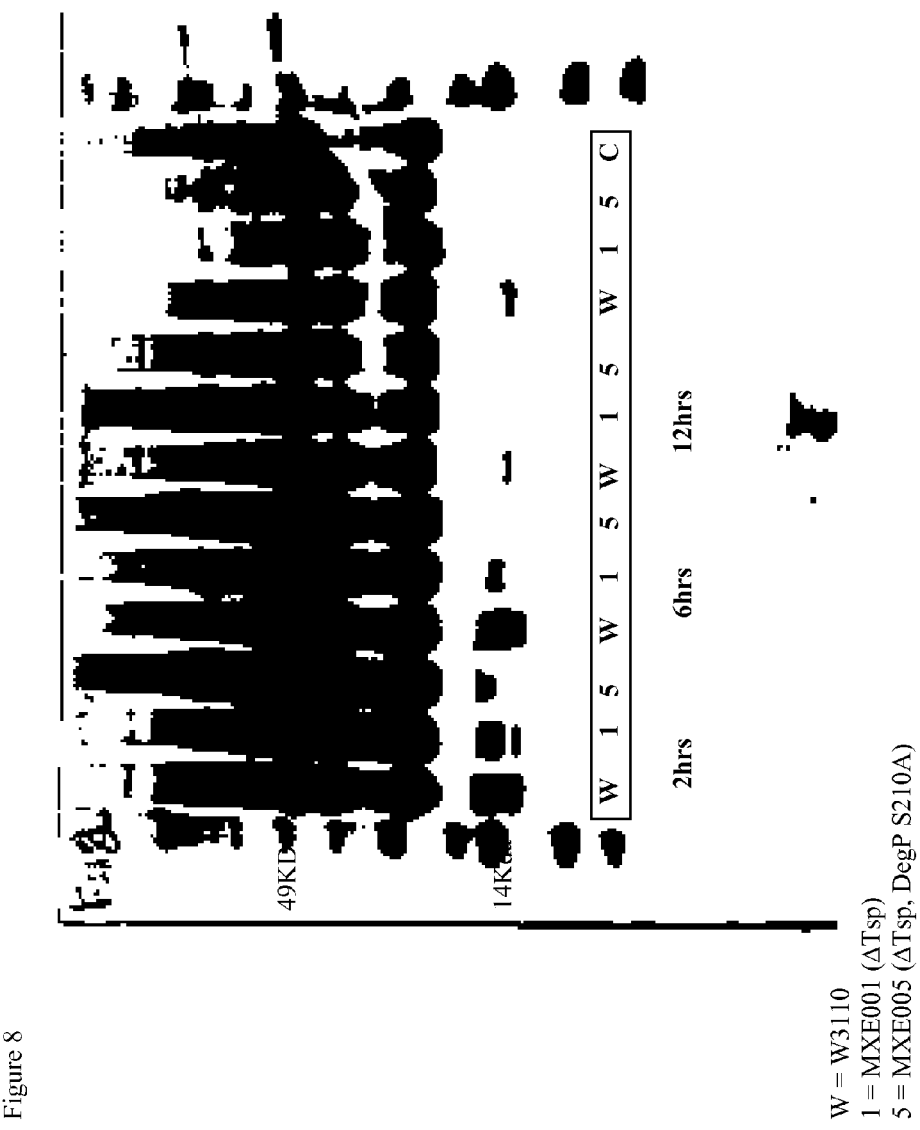
FIG. 8 shows the results of a western blot analysis for wild type W3110, MXE001 and MXE005 showing relative fragmentation of a Fab'.

FIG. 8 shows the results of the western blot analysis where W=W3110, 1=MXE001 (ΔTsp) and 5=MXE005 (ΔTsp, DegP S210A). Fragmentation around the 14 KDa is thought to represent proteolytic fragments of the light chain of the expressed Fab'. It can be seen that MXE001 and MXE005 have less proteolysed products compared to the wild type W3110 around the 14 KDa mark. Without being bound by theory, this data suggests that the anti-TNFα Fab' is susceptible to proteolysis by Tsp and DegP.

Example 6

Growth of Mutated *E. coli* Strains and Expression of Fab' in Mutated *E. coli* Strains Using High Density Fermentations Strain MXE005 and wild type W3110 cells were transformed with plasmid pMXE117 tested in fermentation experiments comparing growth and expression of an anti-TNFα Fab'.
Growth Medium.
The fermentation growth medium was based on SM6E medium (described in Humphreys et al., 2002, *Protein Expression and Purification*, 26, 309-320) with 3.86 g/l NaH$_2$PO$_4$.H$_2$O and 112 g/l glycerol.
Inoculum.
Inoculum cultures were grown in the same medium supplemented with 10 μg/ml tetracycline. Cultures were incubated at 30° C. with agitation for approximately 22 hours.
Fermentation.
Fermenters (2.5 liters total volume) were seeded with inoculum culture to 0.3-0.5 OD$_{600}$. Temperature was maintained at 30° C. during the growth phase and was reduced to 25° C. prior to induction. The dissolved oxygen concentration was maintained above 30% air saturation by variable agitation and airflow. Culture pH was controlled at 7.0 by automatic titration with 15% (v/v) NH$_4$OH and 10% (v/v) conc. H$_2$SO$_4$. Foaming was controlled by the addition of 10% (v/v) Struktol J673 solution (Schill and Seilacher).

A number of additions were made at different stages of the fermentation. When biomass concentration reached approximately 40 OD$_{600}$, magnesium salts and NaH$_2$PO$_4$.H$_2$O were added. Further additions of NaH$_2$PO$_4$.H$_2$O were made prior to and during the induction phase to ensure phosphate was maintained in excess. When the glycerol present at the beginning of fermentation had depleted (approximately 75 OD$_{600}$) a continuous feed of 80% (w/w) glycerol was applied. At the same point in the fermentation an IPTG feed at 170 μM was applied. The start of IPTG feeding was taken as the start of induction. Fermentations were typically run for 70-73 hours at the lower glycerol feed rates (0.5-2.5 ml/h) and 50-60 h at the higher glycerol feed rates (5.4-10.9 ml/h).
Measurement of Biomass Concentration and Growth Rate.
Biomass concentration was determined by measuring the optical density of cultures at 600 nm.
Periplasmic Extraction.
Cells were collected from culture samples by centrifugation. The supernatant fraction was retained (at −20° C.) for further analysis. The cell pellet fraction was resuspended to the original culture volume in extraction buffer (100 mM Tris-HCl, 10 mM EDTA; pH 7.4). Following incubation at 60° C. for approximately 16 hours the extract was clarified by centrifugation and the supernatant fraction retained (at −20° C.) for analysis.
Fab' Quantification.
Fab' concentrations in periplasmic extracts and culture supernatants were determined by Fab' assembly ELISA as described in Humphreys et al., 2002, *Protein Expression and Purification*, 26, 309-320.

Figure 9:
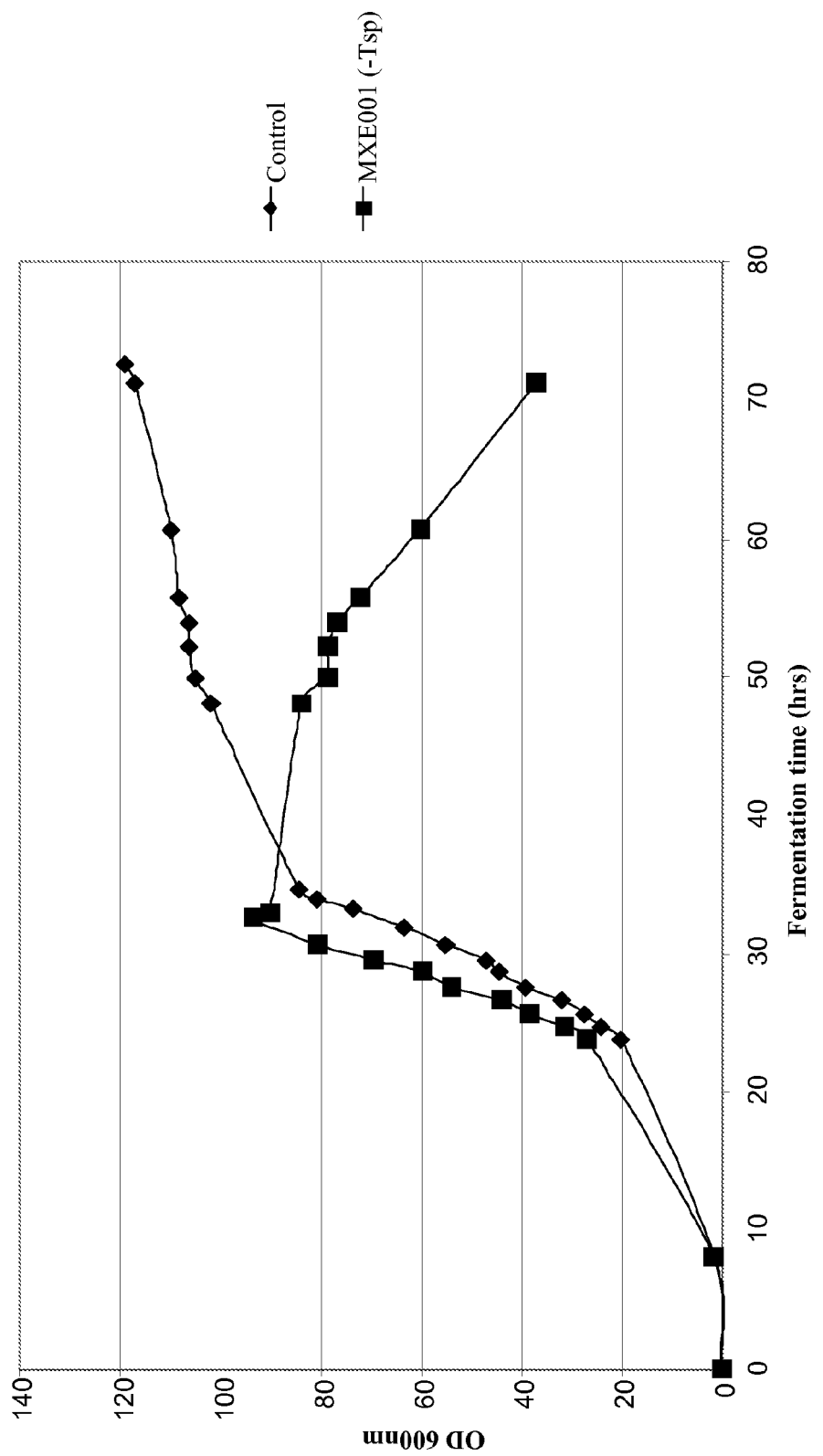
FIG. 9 shows the growth profile of MXE001 compared to control W3110.

FIG. 9 shows the growth profile of MXE001 compared to control W3110 which shows that the growth profiles are substantially the same for approximately 35 hours.

Figure 10:
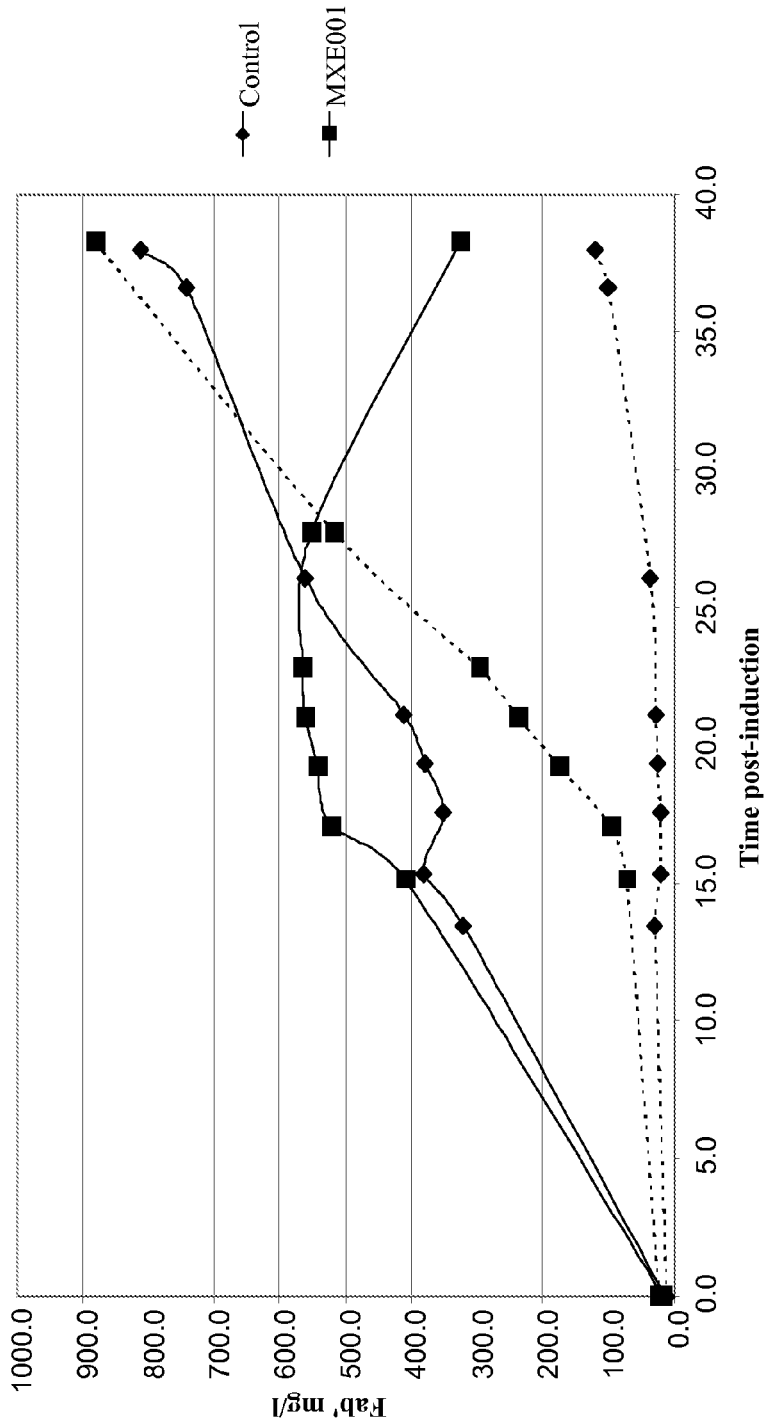
FIG. 10 shows Fab' yield from the supernatant (dotted lines) and periplasm (solid lines) from *E. coli* strain MXE001 compared to control *E. coli* W3110.

FIG. 10 shows Fab yield from the supernatant (dotted lines) and periplasm (solid lines) from *E. coli* strain MXE001 compared to control W3110. The MXE001 strain shows higher periplasmic Fab' expression up to approximately 30 hours and significantly higher supernatant Fab' expression over the whole fermentation period.

Figure 11:
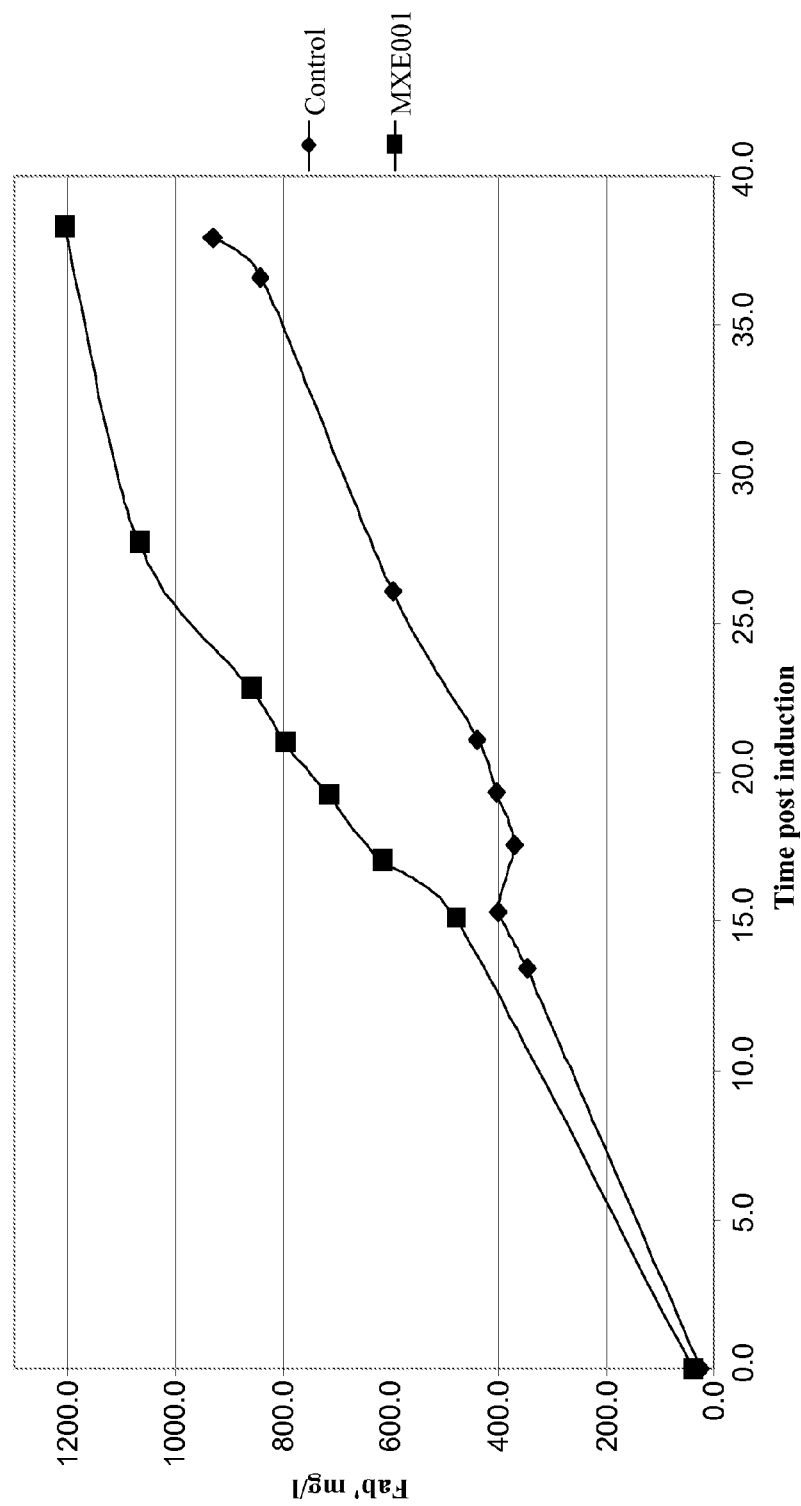
FIG. 11 shows the total Fab' yield from the supernatant and periplasm of the *E. coli* strain MXE001 compared to control W3110.

FIG. 11 shows the total Fab' yield from the supernatant and periplasm of the *E. coli* strain MXE001 compared to control W3110 where it can be seen that the MXE005 strain produced higher Fab' yield compared to the control W3110.

Figure 12:
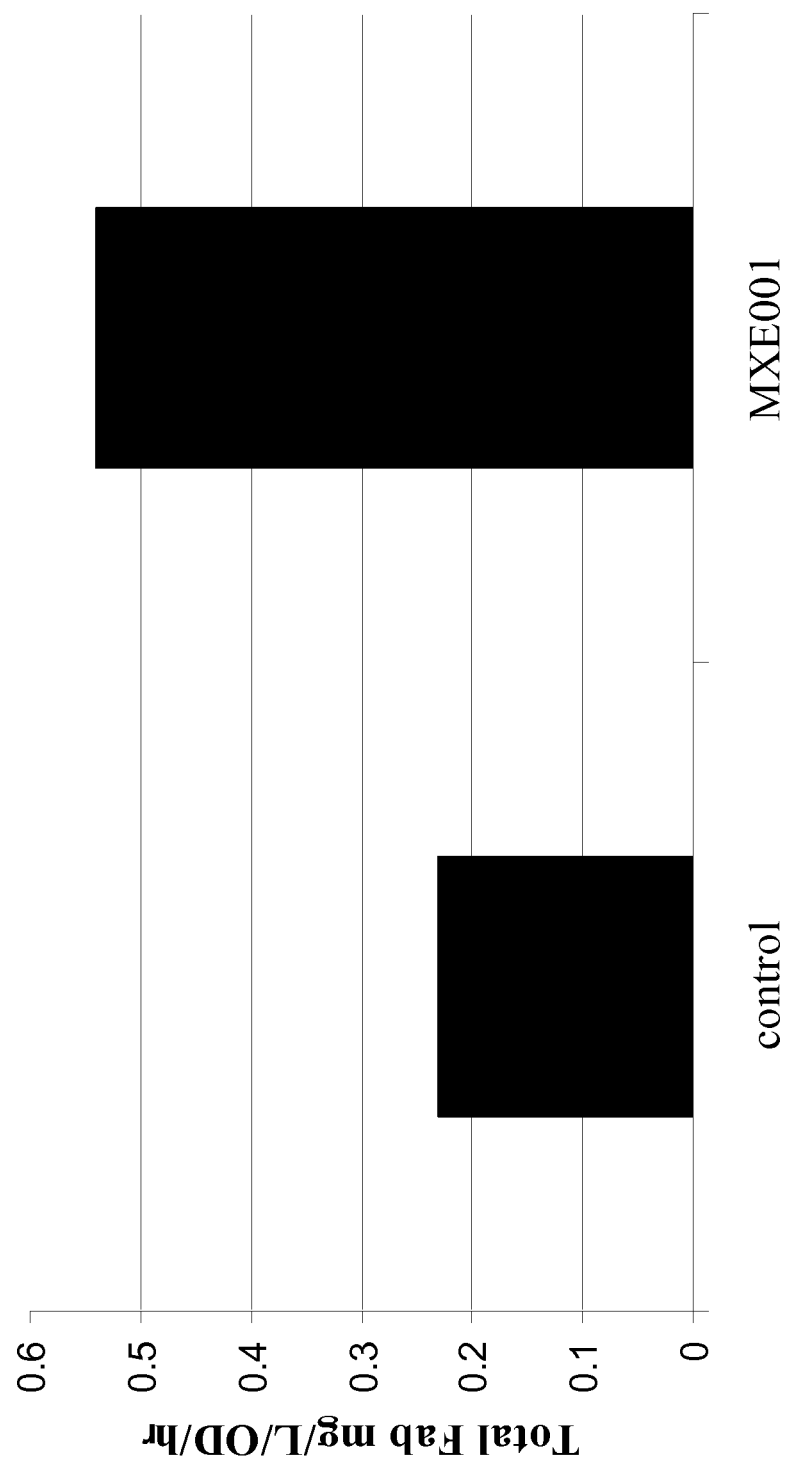
FIG. 12 shows the Fab' specific production rate of *E. coli* strain MXE001 compared to the control W3110.

FIG. 12 shows the Fab' specific production rate of *E. coli* strain MXE001 compared to the control W3110 where it can be seen that MXE001 has significantly higher specific production rate compared to W3110.

Figure 13:
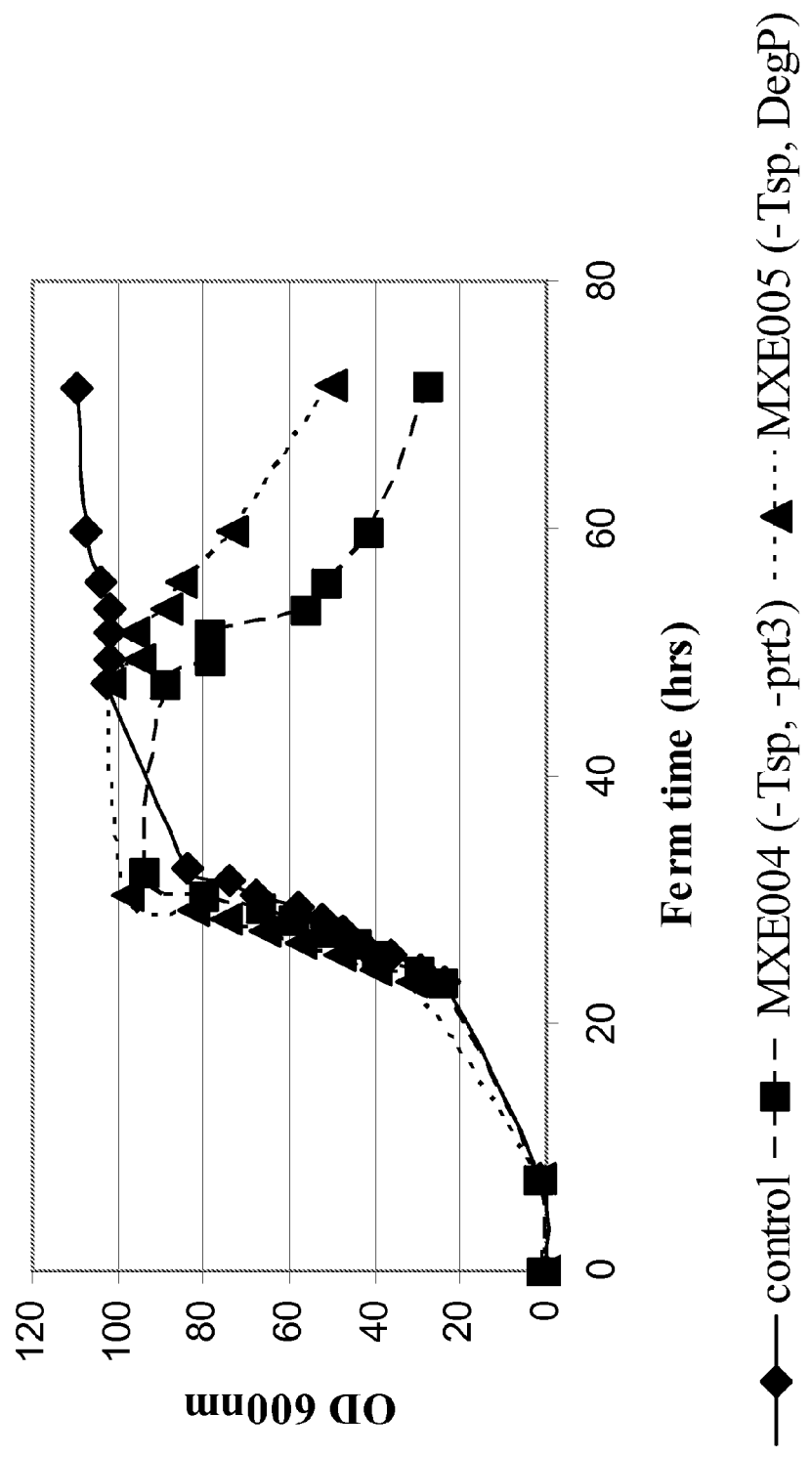
FIG. 13 shows the growth profile of MXE004 and MXE005 compared to control W3110.

FIG. 13 shows the growth profile of MXE004 and MXE005 compared to control W3110. The growth profiles of MXE004 and MXE005 are faster over the initial period of approximately 35 hours compared to the control W3110.

Figure 14:
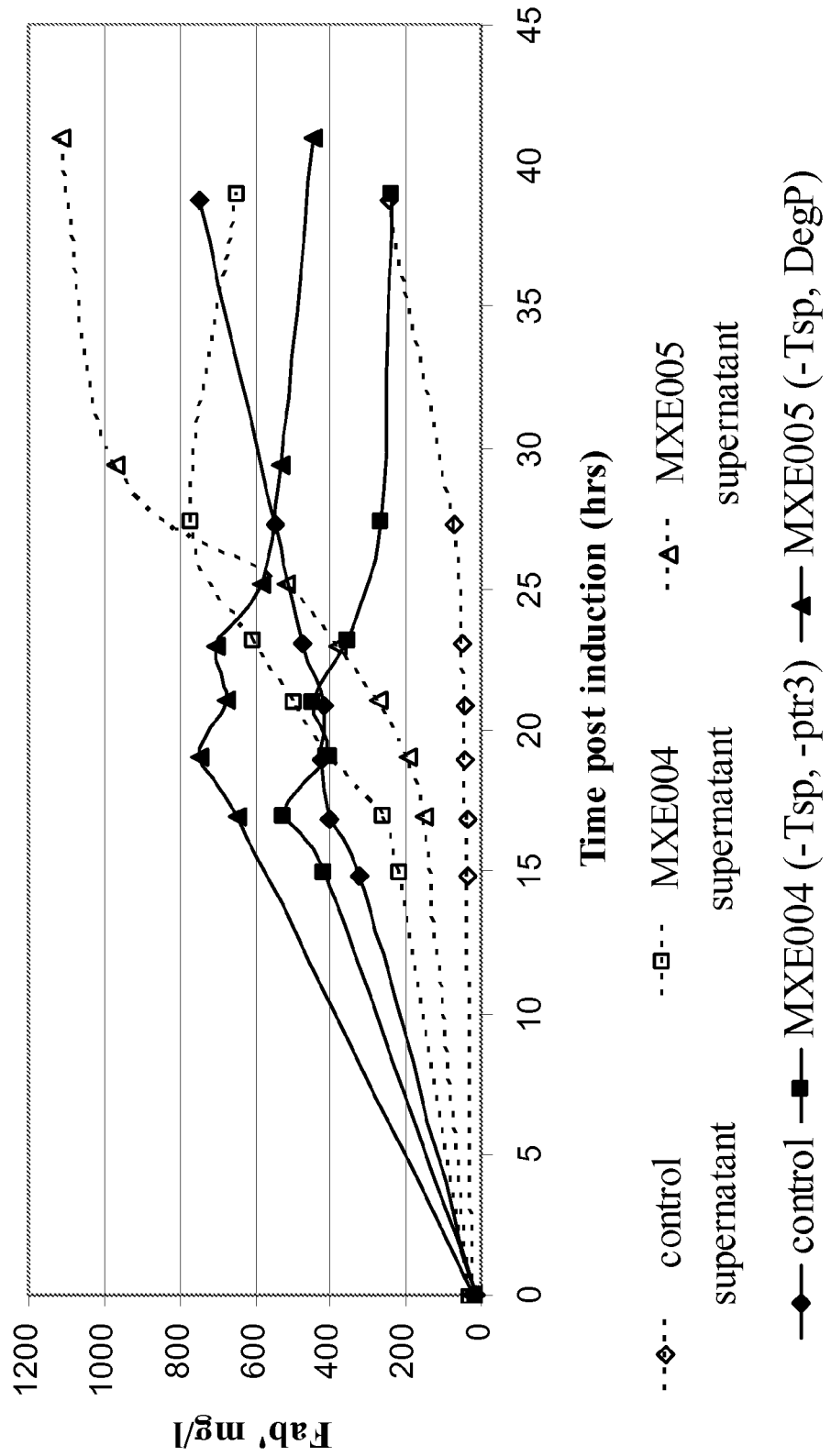
FIG. 14 shows Fab' yields from the supernatant (dotted lines) and periplasm (solid lines) of *E. coli* strains MXE004, MXE005 and the W3110 control.

FIG. 14 shows Fab' yields from the supernatant (dotted lines) and periplasm (solid lines) of *E. coli* strains MXE004, MXE005 and the W3110 control. The MXE005 strain shows higher Fab' yield from the periplasm for approximately 28 hours compared to the control and significantly higher supernatant Fab' yield compared to the control over the whole fermentation period. The MXE004 strain shows higher Fab' yield from the periplasm for approximately 20 hours compared to the control and significantly higher supernatant Fab' yield compared to the control over the whole fermentation period.

Figure 15:
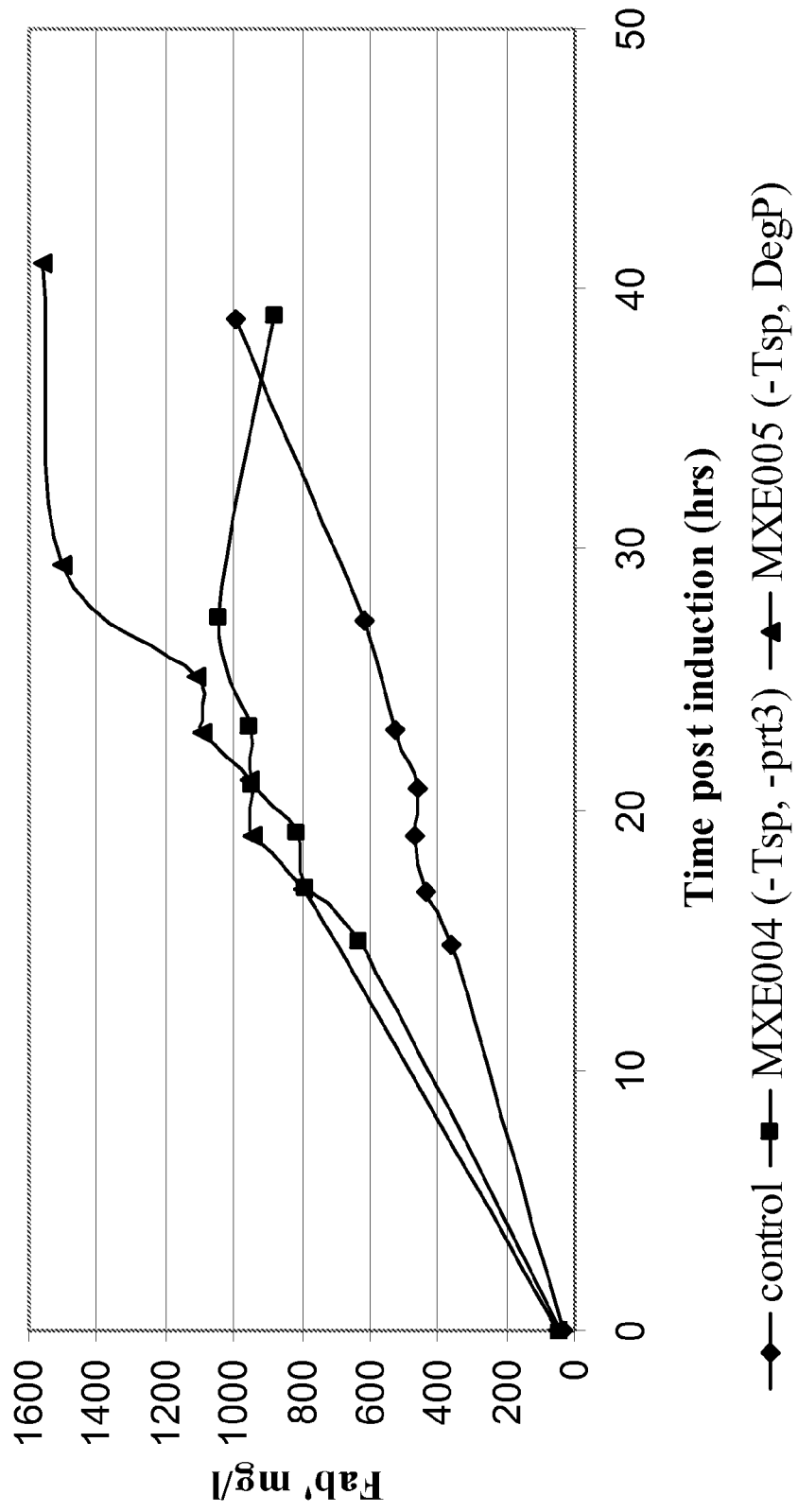
FIG. 15 shows the total Fab' yield from the supernatant and periplasm of the *E. coli* strains MXE004 and MXE005.

FIG. 15 shows the total Fab' yield from the supernatant and periplasm of the *E. coli* strains MXE004 and MXE005 where it can be clearly seen that the MXE004 and MXE005 strains produced significantly higher yield compared to the control.

Figure 16:
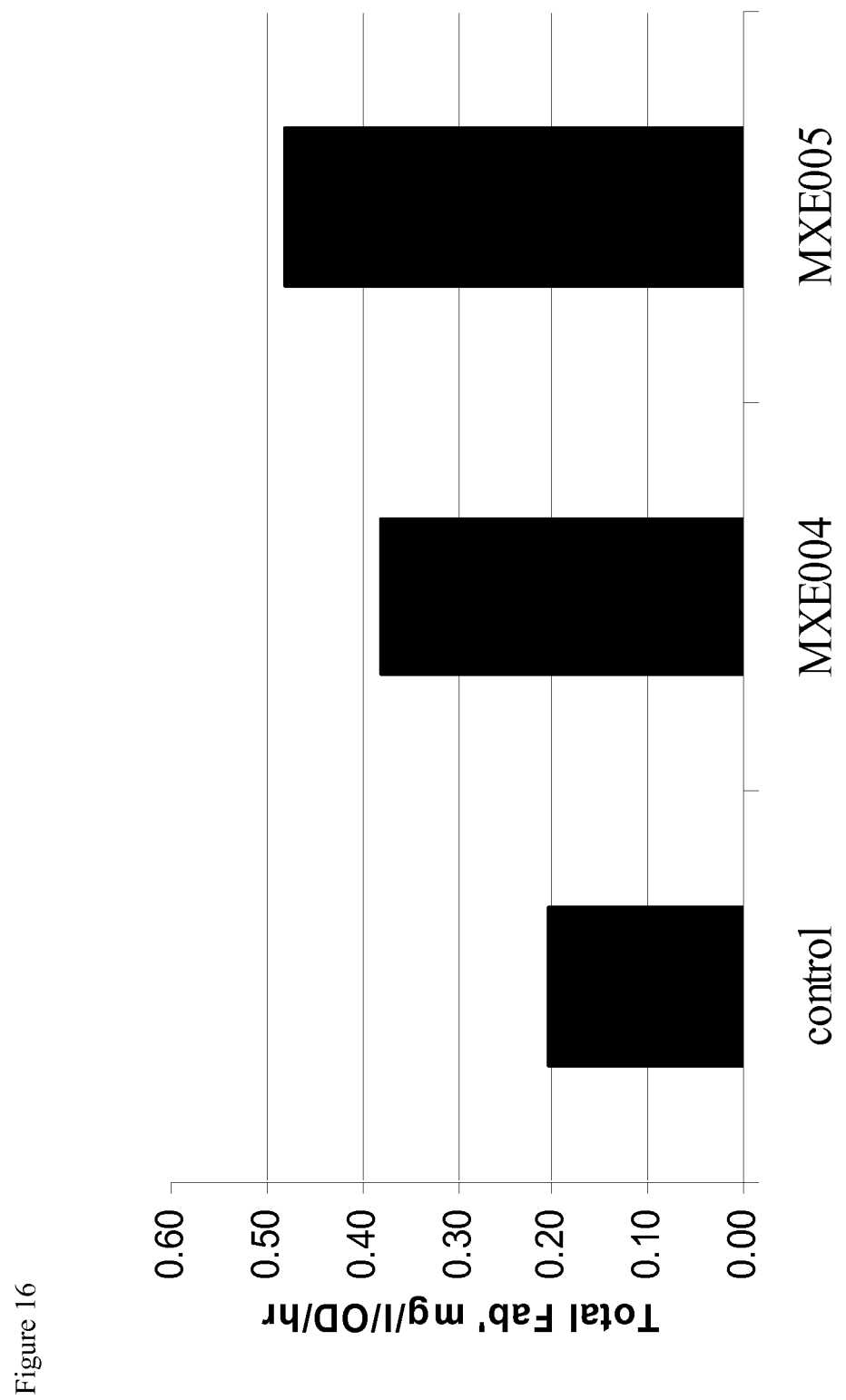
FIG. 16 shows the Fab' specific production rate of *E. coli* strains MXE004 and MXE005 and the W3110 control.

FIG. 16 shows the Fab' specific production rate of *E. coli* strains MXE004 and MXE005 and the W3110 control where it can be seen that MXE004 and MXE005 have a significantly higher specific production rate compared to W3110.

Example 7

Growth of Mutated *E. coli* Strains MXE001, MXE004 and MXE005 Compared to W3110 and Highly Mutated *E. coli* Strains in Shake Flask Experiment The following strains were analyzed in a shake flask experiment to assess growth rate: Mutated *E. coli* strains MXE001, MXE004 and MXE005 derived from W3110 (Example 1);

Wild-Type *E. coli* Strain W3110;

SURE (Stratagene) having genotype: endA1 glnV44 thi-1 gyrA96 relA1 lac recB recJ sbcC umuC::Tn5 uvrC e14-Δ (mcrCB-hsdSMR-mrr)171 F'[proAB+ lacI$^q$ lacZΔM15 Tn10];

STBL3 (Invitrogen) having genotype: F– glnV44 recA13 mcrB mrr hsdS20(rB–, mB–) ara-14 galK2 lacY1 proA2 rpsL20 xyl-5 leu mtl-1;

TOP10 (Invitrogen) having genotype: F– mcrA Δ(mrr-hsdRMS-mcrBC); φ80lacZΔM15 ΔlacX74 nupG recA1 araD139 Δ(ara-leu)7697 galE15 galK16 rpsL(Str$^R$) endA1 λ–; and XL1-Blue (Stratagene) having genotype endA1 gyrA96 (nal$^R$) thi-1 recA1 relA1 lac glnV44 F[::Tn10 proAB+ lacI$^q$ Δ(lacZ)M15] hsdR17($r_K^-$ $m_K^+$).

Figure 17:
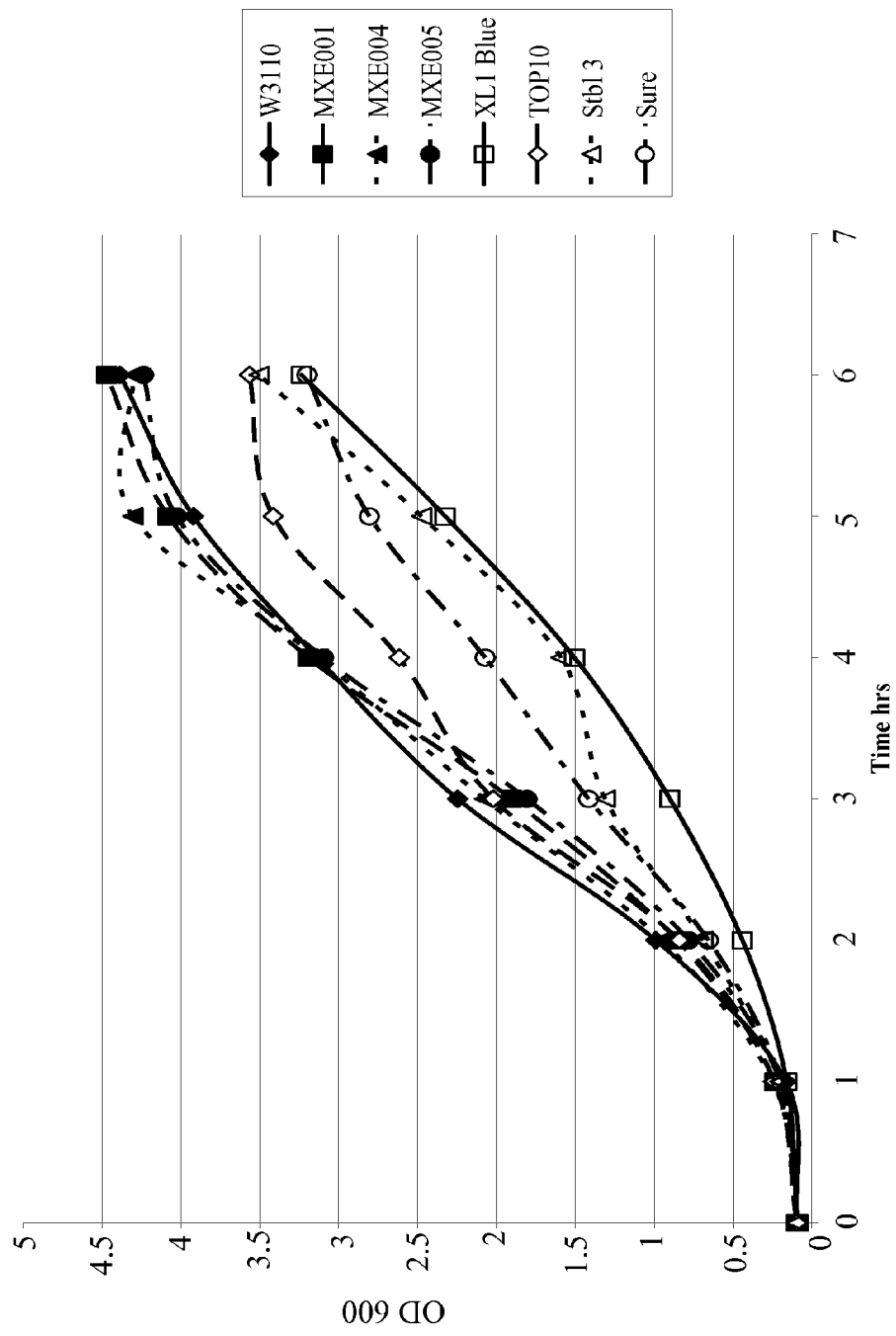
FIG. 17 shows the growth profile of *E. coli* strains W3110, MXE001, MXE004 and MXE005 compared to *E. coli* strains XL1 Blue, TOP10, Stbl 3 and Sure.

A single colony was picked into 5 ml of LB broth (10 g Tryptone, 5 g yeast extract, 10 g NaCl per liter) and grown overnight at 37° C. with shaking at 250 rpm. The overnight culture was used to inoculate 75 ml of LB broth to an OD$_{660}$ of 0.1 (n=2). The cultures were grown at 37° C. with shaking at 250 rpm, 0.2 ml samples were removed every hour and the OD$_{600}$ recorded. The OD600 was then plotted against time in hours and the results are shown in FIG. 17. It can be seen from FIG. 17 that the heavily mutated *E. coli* strains have a lower growth rate compared to MXE001, MXE004, MXE005 and W3110.

While this invention has been particularly shown and described with reference to preferred embodiments, it will be understood to those skilled in the art that various changes in form and detail may be made without departing from the scope of the invention as defined by the appendant claims.

The invention claimed is:

1. A mutant *E. coli* cell strain selected from:
   MXE002 having genotype Δptr and deposited with the National Collection of Type Cultures, MPA, United Kingdom, under Accession number NCTC13445;
   MXE003 having genotype DegP S210A and deposited with the National Collection of Type Cultures, HPA, United Kingdom, under Accession number NCTC13446; or
   MXE006 having genotype Δptr, DegP S210A and deposited with the National Collection of Type Cultures, HPA, United Kingdom, under Accession number NCTC13449.

2. An isolated gram-negative bacterial cell comprising a mutated DegP gene, wherein the mutated DegP gene encodes a DegP protease that comprises a mutation at an amino acid selected from the group consisting of His105, Asp135, Ser210 and combinations thereof and said bacterial cell is isogenic to a wild-type bacterial cell except for the mutated DegP gene and, optionally, one or more of the following genetic alterations:
   a) a mutated ptr gene, wherein the mutated ptr gene encodes a Protease III protein having reduced protease activity or is a knockout mutated ptr gene;
   b) a mutated Tsp gene, wherein the mutated Tsp gene encodes a Tsp protein having reduced protease activity or is a knockout mutated Tsp gene; and/or
   c) a polynucleotide encoding a protein of interest.

3. The isolated gram-negative bacterial cell according to claim 2, wherein said DegP protease comprises: a mutation to His105; a mutation to Asp135; a mutation to Ser210; a mutation to His105 and Asp135; a mutation to His105 and Ser210; a mutation to Asp135 and Ser210; or a mutation to His105, Asp135 and Ser210.

4. The isolated gram-negative bacterial cell according to claim 2, wherein one or more of His105, Asp135, and Ser210 are substituted with a glycine or alanine.

5. The isolated gram-negative bacterial cell according to claim 3, wherein His105, Asp135, and Ser210 are substituted with a glycine or alanine.

6. The isolated gram-negative bacterial cell according to claim 2, wherein His105 is substituted with a glycine, alanine, valine or leucine.

7. The isolated gram-negative bacterial cell according to claim 2, wherein Asp135 is substituted with a glycine, alanine, lysine or arginine.

8. The isolated gram-negative bacterial cell according to claim 2, wherein Ser210 is substituted with a glycine, alanine, valine, leucine, phenylalanine or tyrosine.

9. The isolated gram-negative bacterial cell according to claim 3, wherein His105 is substituted with a glycine, alanine, valine or leucine; Asp135 is substituted with a glycine, alanine, lysine or arginine; and Ser210 is substituted with a glycine, alanine, valine, leucine, phenylalanine or tyrosine.

10. The isolated gram-negative bacterial cell according to claim 2, wherein said bacterial cell comprises a mutated DegP gene and a mutated ptr gene, wherein the mutated ptr gene encodes a Protease III protein having reduced protease activity or is a knockout mutated ptr gene.

11. The isolated gram-negative bacterial cell according to claim 2, wherein said bacterial cell comprises a mutated DegP gene and a mutated Tsp gene, wherein the mutated Tsp gene encodes a Tsp protein having reduced protease activity or is a knockout mutated Tsp gene.

12. The isolated gram-negative bacterial cell according to claim 2, wherein said bacterial cell comprises a mutated DegP gene and a polynucleotide encoding a protein of interest.

13. The isolated gram-negative bacterial cell according to claim 2, wherein said bacterial cell comprises a mutated DegP gene, a mutated ptr gene, wherein the mutated ptr gene encodes a Protease III protein having reduced protease activity or is a knockout mutated ptr gene and a mutated Tsp gene, wherein the mutated Tsp gene encodes a Tsp protein having reduced protease activity or is a knockout mutated Tsp gene.

14. The isolated gram-negative bacterial cell according to claim 10, wherein said bacterial cell further comprises a polynucleotide encoding a protein of interest.

15. The isolated gram-negative bacterial cell according to claim 11, wherein said bacterial cell further comprises a polynucleotide encoding a protein of interest.

16. The isolated gram-negative bacterial cell according to claim 13, wherein said bacterial cell further comprises a polynucleotide encoding a protein of interest.

17. The isolated gram-negative bacterial cell according to claim 12, wherein said protein of interest is an antibody or antigen-binding fragment thereof.

18. The isolated gram-negative bacterial cell according to claim 14, wherein said protein of interest is an antibody or antigen-binding fragment thereof.

19. The isolated gram-negative bacterial cell according to claim 15, wherein said protein of interest is an antibody or antigen-binding fragment thereof.

20. The isolated gram-negative bacterial cell according to claim 16, wherein said protein of interest is an antibody or antigen-binding fragment thereof.

* * * * *

SEQUENCE LISTING

```
<160> NUMBER OF SEQ ID NOS: 26

<210> SEQ ID NO 1
<211> LENGTH: 2049
<212> TYPE: DNA
<213> ORGANISM: E. coli

<400> SEQUENCE: 1
atgaacatgt tttttaggct taccgcgtta gctggcctgc ttgcaatagc aggccagacc      60
ttcgctgtag aagatatcac gcgtgctgat caaattccgg tattaaagga agagacgcag     120
catgcgacgg taagtgagcg cgtaacgtcg cgcttcaccc gttctcatta tcgccagttc     180
gacctcgatc aggcattttc ggccaaaatc tttgaccgct acctgaatct gctcgattac     240
agccacaacg tgctgctggc aagcgatgtt gaacagttcg cgaaaaagaa aaccgagtta     300
ggcgatgaac tgcgttcagg caaactcgac gttttctacg atctctacaa tctggcgcaa     360
aagcgccgtt ttgagcgtta ccagtacgct ttgtcggtac tggaaaagcc gatggatttc     420
accggcaacg acacttataa ccttgaccgc agcaaagcgc cctggccgaa aaacgaggct     480
```

```
gagttgaacg cgctgtggga cagtaaagtc aaattcgacg agttaagcct gaagctgaca    540
ggaaaaacgg ataaagaaat tcgtgaaacc ctgactcgcc gctacaaatt tgccattcgt    600
cgtctggcgc aaaccaacag cgaagatgtt ttctcgctgg caatgacggc gtttgcgcgt    660
gaaatcgacc cgcataccaa ctatctttcc ccgcgtaata ccgaacagtt caacactgaa    720
atgagtttgt cgctggaagg tattggcgca gtgctgcaaa tggatgatga ctacaccgtt    780
atcaattcga tggtggcagg tggtccggca gcgaagagta agctatcag cgttggtgac     840
aaaattgtcg gtgttggtca acaggcaag ccgatggttg acgtgattgg ctggcgtctt     900
gatgatgtgg ttgccttaat taagggccg aagggcagta agttcgtct ggaaatttta     960
cctgctggta aagggaccaa gacccgtact gtaacgttga cccgtgaacg tattcgtctc    1020
gaagaccgcg cggttaaaat gtcggtgaag accgtcggta agagaaagt cggcgtgctg    1080
gatattccgg gcttctatgt gggttttgaca dacgatgtca aagtgcaact gcagaaactg    1140
gaaaaacaga atgtcagcag cgtcatcatc gacctgcgta gcaatggcgg tgggcgttta   1200
actgaagccg tatcgctctc cggtctgttt attcctgcgg gtcccattgt tcaggtccgc   1260
gataacaacg gcaaggttcg tgaagatagc gataccgacg gacaggtttt ctataaaggc   1320
ccgctggtgg tgctggttga ccgcttcagt gcttcggctt cagaaatctt tgccgcggca   1380
atgcaggatt acggtcgtgc gctggttgtg ggtgaaccga cgtttggtaa aggcaccgtt   1440
cagcaatacc gttcattgaa ccgtatttac gatcagatgt acgtcctga atggccagcg    1500
ctgggttctg tgcagtacac gatccagaaa ttctatcgcg ttaacggcgg cagtacgcaa   1560
cgtaaaggcg taacgccaga catcatcatg ccgacgggta atgaagaaac ggaaacgggt   1620
gagaaattcg aagataacgc gctgccgtgg gatagcattg atgccgcgac ttatgtgaaa   1680
tcaggagatt taacggcctt tgaaccggag ctgctgaagg aacataatgc gcgtatcgcg   1740
aaagatcctg agttccagaa catcatgaag gatatcgcgc gcttcaacgc tatgaaggac   1800
aagcgcaata tcgtttctct gaattacgct gtgcgtgaga agagaataa tgaagatgat    1860
gcgacgcgtc tggcgcgttt gaacgaacgc tttaaacgcg aaggtaaacc ggagttgaag   1920
aaactggatg atctaccgaa agattaccag gagccggatc cttatctgga tgagacggtg   1980
aatatcgcac tcgatctggc gaagcttgaa aaagccagac ccgcggaaca acccgctccc   2040
gtcaagtaa                                                            2049
```

<210> SEQ ID NO 2
<211> LENGTH: 682
<212> TYPE: PRT
<213> ORGANISM: E. coli

<400> SEQUENCE: 2

```
Met Asn Met Phe Phe Arg Leu Thr Ala Leu Ala Gly Leu Leu Ala Ile
1               5                   10                  15

Ala Gly Gln Thr Phe Ala Val Glu Asp Ile Thr Arg Ala Asp Gln Ile
            20                  25                  30

Pro Val Leu Lys Glu Glu Thr Gln His Ala Thr Val Ser Glu Arg Val
        35                  40                  45

Thr Ser Arg Phe Thr Arg Ser His Tyr Arg Gln Phe Asp Leu Asp Gln
    50                  55                  60

Ala Phe Ser Ala Lys Ile Phe Asp Arg Tyr Leu Asn Leu Leu Asp Tyr
65                  70                  75                  80

Ser His Asn Val Leu Leu Ala Ser Asp Val Glu Gln Phe Ala Lys Lys
                85                  90                  95
```

```
Lys Thr Glu Leu Gly Asp Glu Leu Arg Ser Gly Lys Leu Asp Val Phe
            100                 105                 110

Tyr Asp Leu Tyr Asn Leu Ala Gln Lys Arg Arg Phe Glu Arg Tyr Gln
            115                 120                 125

Tyr Ala Leu Ser Val Leu Glu Lys Pro Met Asp Phe Thr Gly Asn Asp
            130                 135                 140

Thr Tyr Asn Leu Asp Arg Ser Lys Ala Pro Trp Pro Lys Asn Glu Ala
145                 150                 155                 160

Glu Leu Asn Ala Leu Trp Asp Ser Lys Val Lys Phe Asp Glu Leu Ser
                    165                 170                 175

Leu Lys Leu Thr Gly Lys Thr Asp Lys Glu Ile Arg Glu Thr Leu Thr
            180                 185                 190

Arg Arg Tyr Lys Phe Ala Ile Arg Arg Leu Ala Gln Thr Asn Ser Glu
            195                 200                 205

Asp Val Phe Ser Leu Ala Met Thr Ala Phe Ala Arg Glu Ile Asp Pro
            210                 215                 220

His Thr Asn Tyr Leu Ser Pro Arg Asn Thr Glu Gln Phe Asn Thr Glu
225                 230                 235                 240

Met Ser Leu Ser Leu Glu Gly Ile Gly Ala Val Leu Gln Met Asp Asp
                    245                 250                 255

Asp Tyr Thr Val Ile Asn Ser Met Val Ala Gly Gly Pro Ala Ala Lys
            260                 265                 270

Ser Lys Ala Ile Ser Val Gly Asp Lys Ile Val Gly Val Gly Gln Thr
            275                 280                 285

Gly Lys Pro Met Val Asp Val Ile Gly Trp Arg Leu Asp Asp Val Val
            290                 295                 300

Ala Leu Ile Lys Gly Pro Lys Gly Ser Lys Val Arg Leu Glu Ile Leu
305                 310                 315                 320

Pro Ala Gly Lys Gly Thr Lys Thr Arg Thr Val Thr Leu Thr Arg Glu
            325                 330                 335

Arg Ile Arg Leu Glu Asp Arg Ala Val Lys Met Ser Val Lys Thr Val
            340                 345                 350

Gly Lys Glu Lys Val Gly Val Leu Asp Ile Pro Gly Phe Tyr Val Gly
            355                 360                 365

Leu Thr Asp Asp Val Lys Val Gln Leu Gln Lys Leu Glu Lys Gln Asn
370                 375                 380

Val Ser Ser Val Ile Ile Asp Leu Arg Ser Asn Gly Gly Gly Ala Leu
385                 390                 395                 400

Thr Glu Ala Val Ser Leu Ser Gly Leu Phe Ile Pro Ala Gly Pro Ile
                    405                 410                 415

Val Gln Val Arg Asp Asn Asn Gly Lys Val Arg Glu Asp Ser Asp Thr
            420                 425                 430

Asp Gly Gln Val Phe Tyr Lys Gly Pro Leu Val Val Leu Val Asp Arg
            435                 440                 445

Phe Ser Ala Ser Ala Ser Glu Ile Phe Ala Ala Ala Met Gln Asp Tyr
            450                 455                 460

Gly Arg Ala Leu Val Val Gly Glu Pro Thr Phe Gly Lys Gly Thr Val
465                 470                 475                 480

Gln Gln Tyr Arg Ser Leu Asn Arg Ile Tyr Asp Gln Met Leu Arg Pro
            485                 490                 495

Glu Trp Pro Ala Leu Gly Ser Val Gln Tyr Thr Ile Gln Lys Phe Tyr
            500                 505                 510
```

```
Arg Val Asn Gly Gly Ser Thr Gln Arg Lys Gly Val Thr Pro Asp Ile
        515                 520                 525

Ile Met Pro Thr Gly Asn Glu Glu Thr Glu Thr Gly Glu Lys Phe Glu
    530                 535                 540

Asp Asn Ala Leu Pro Trp Asp Ser Ile Asp Ala Ala Thr Tyr Val Lys
545                 550                 555                 560

Ser Gly Asp Leu Thr Ala Phe Glu Pro Glu Leu Leu Lys Glu His Asn
                565                 570                 575

Ala Arg Ile Ala Lys Asp Pro Glu Phe Gln Asn Ile Met Lys Asp Ile
            580                 585                 590

Ala Arg Phe Asn Ala Met Lys Asp Lys Arg Asn Ile Val Ser Leu Asn
        595                 600                 605

Tyr Ala Val Arg Glu Lys Glu Asn Asn Glu Asp Asp Ala Thr Arg Leu
    610                 615                 620

Ala Arg Leu Asn Glu Arg Phe Lys Arg Glu Gly Lys Pro Glu Leu Lys
625                 630                 635                 640

Lys Leu Asp Asp Leu Pro Lys Asp Tyr Gln Glu Pro Asp Pro Tyr Leu
                645                 650                 655

Asp Glu Thr Val Asn Ile Ala Leu Asp Leu Ala Lys Leu Glu Lys Ala
            660                 665                 670

Arg Pro Ala Glu Gln Pro Ala Pro Val Lys
        675                 680

<210> SEQ ID NO 3
<211> LENGTH: 2048
<212> TYPE: DNA
<213> ORGANISM: E. coli

<400> SEQUENCE: 3
atgaattcgt ttttaggctt accgcgttag ctggcctgct tgcaatagca ggccagacat        60
taattgtaga agatatcacg cgtgctgatc aaattccggt attaaaggaa gagacgcagc       120
atgcgacggt aagtgagcgc gtaacgtcgc gcttcacccg ttctcattat cgccagttcg       180
acctcgatca ggcattttcg gccaaaatct tgaccgcta cctgaatctg ctcgattaca       240
gccacaacgt gctgctggca agcgatgttg aacagttcgc gaaaaagaaa accgagttag       300
gcgatgaact gcgttcaggc aaactcgacg ttttctacga tctctacaat ctggcgcaaa       360
agcgccgttt tgagcgttac cagtacgctt tgtcggtact ggaaaagccg atggatttca       420
ccggcaacga cacttataac cttgaccgca gcaaagcgcc ctggccgaaa acgaggctg       480 agttgaacgc gctgtgggac agtaaagtca aattcgacga gttaagcctg aagctgacag       540
gaaaaacgga taagaaaatt cgtgaaaccc tgactcgccg ctacaaattt gccattcgtc       600
gtctggcgca aaccaacagc gaagatgttt tctcgctggc aatgacggcg tttgcgcgtg       660
aaatcgaccc gcataccaac tatctttccc cgcgtaatac cgaacagttc aacactgaaa       720
tgagtttgtc gctggaaggt attggcgcag tgctgcaaat ggatgatgac tacaccgtta       780
tcaattcgat ggtggcaggt ggtccggcag cgaagagtaa agctatcagc gttggtgaca       840
aaattgtcgg tgttggtcaa acaggcaagc cgatggttga cgtgattggc tggcgtcttg       900
atgatgtggt tgcctaatt aaagggccga agggcagtaa agttcgtctg gaaattttac       960
ctgctggtaa agggaccaag acccgtactg taacgttgac ccgtgaacgt attcgtctcg      1020
aagaccgcgc ggttaaaatg tcggtgaaga ccgtcggtaa agagaaagtc ggcgtgctgg      1080
atattccggg cttctatgtg ggtttgacag acgatgtcaa agtgcaactg cagaaactgg      1140
```

```
aaaaacagaa tgtcagcagc gtcatcatcg acctgcgtag caatggcggt ggggcgttaa    1200
ctgaagccgt atcgctctcc ggtctgttta ttcctgcggg tcccattgtt caggtccgcg    1260
ataacaacgg caaggttcgt gaagatagcg ataccgacgg acaggttttc tataaaggcc    1320
cgctggtggt gctggttgac cgcttcagtg cttcggcttc agaaatcttt gccgcggcaa    1380
tgcaggatta cggtcgtgcg ctggttgtgg gtgaaccgac gtttggtaaa ggcaccgttc    1440
agcaataccg ttcattgaac cgtatttacg atcagatgtt acgtcctgaa tggccagcgc    1500
tgggttctgt gcagtacacg atccagaaat tctatcgcgt taacggcggc agtacgcaac    1560
gtaaaggcgt aacgccagac atcatcatgc cgacgggtaa tgaagaaacg gaaacgggtg    1620
agaaattcga agataacgcg ctgccgtggg atagcattga tgccgcgact tatgtgaaat    1680
caggagattt aacggccttt gaaccggagc tgctgaagga acataatgcg cgtatcgcga    1740
aagatcctga gttccagaac atcatgaagg atatcgcgcg cttcaacgct atgaaggaca    1800
agcgcaatat cgtttctctg aattacgctg tgcgtgagaa agagaataat gaagatgatg    1860
cgacgcgtct ggcgcgtttg aacgaacgct ttaaacgcga aggtaaaccg gagttgaaga    1920
aactggatga tctaccgaaa gattaccagg agccggatcc ttatctggat gagacggtga    1980
atatcgcact cgatctggcg aagcttgaaa aagccagacc cgcggaacaa cccgctcccg    2040
tcaagtaa                                                             2048

<210> SEQ ID NO 4
<211> LENGTH: 2889
<212> TYPE: DNA
<213> ORGANISM: E. coli

<400> SEQUENCE: 4
atgccccgca gcacctggtt caaagcatta ttgttgttag ttgccctttg ggcaccctta      60
agtcaggcag aaacgggatg gcagccgatt caggaaaacca tccgtaaaag tgataaagat     120
aaccgccagt atcaggctat acgtctggat aacggtatgg tggtcttgct ggtttctgat     180
ccgcaggcag ttaaatcgct ctcggcgctg gtggtgcccg ttgggtcgct ggaagatccc     240
gaggcgtacc aggggctggc acattacctt gaacatatga gtctgatggg gtcgaaaaag     300
tacccgcagg ctgacagtct ggccgaatat ctcaaaatgc acggcggtag tcacaatgcc     360
agcactgcgc gtatcgcac ggcttttctat ctggaagttg agaacgacgc cttgcctggt     420
gcggtagacc gcctggccga tgctattgct gaacctttgc tcgacaagaa atatgccgaa     480
cgtgagcgta tgcggtgaa cgctgaatta accatggcgc gtacgcgtga cgggatgcgc     540
atggcacagg tcagcgcaga accattaac ccggcacacc ccggttcaaa gttttctggt     600
ggtaaccttg aaactttaag cgacaaacct ggtaatccgg tgcagcaggc gctgaaagat     660
ttccacgaga agtactattc cgccaatttg atgaaggcgg ttatttacag taataaaccg     720
ctgccggagt tggcaaaaat ggcggcggac acctttggtc gcgtgccgaa caaagagagc     780
aaaaaaccgg aaatcaccgt gccggtagtc accgacgcgc aaaagggcat tatcattcat     840
tacgtccctg cgctgccgcg taaagtgttg cgcgttgagt ttcgcatcga taacaactca     900
gcgaagttcc gtagtaaaac cgatgaattg attacctatc tgattggcaa tcgcagccca     960
ggtacacttt ctgactggct gcaaaagcag ggattagttg agggcattag cgccaactcc    1020
gatcctatcg tcaacggcaa cagcggcgta ttagcgatct ctgcgtcttt aaccgataaa    1080
ggcctggcta atcgcgatca ggttgtggcg gcaattttta gctatctcaa tctgttacgt    1140
gaaaaaggca ttgataaaca atacttcgat gaactggcga atgtgctgga tatcgacttc    1200
```

```
cgttatccgt cgatcacccg tgatatggat tacgtcgaat ggctggcaga taccatgatt    1260
cgcgttcctg ttgagcatac gctggatgca gtcaatattg ccgatcggta cgatgctaaa    1320
gcagtaaagg aacgtctggc gatgatgacg ccgcagaatg cgcgtatctg gtatatcagc    1380
ccgaaagagc cgcacaacaa aacggcttac tttgtcgatg cgccgtatca ggtcgataaa    1440
atcagcgcac aaactttcgc cgactggcag aaaaaagccg ccgacattgc gctctctttg    1500
ccagagctta acccttatat tcctgatgat ttctcgctga ttaagtcaga gaagaaatac    1560
gaccatccag agctgattgt tgatgagtcg aatctgcgcg tggtgtatgc gccaagccgt    1620
tattttgcca gcgagcccaa agctgatgtc agcctgattt tgcgtaatcc gaaagccatg    1680
gacagcgccc gcaatcaggt gatgtttgcg ctcaatgatt atctcgcagg gctggcgctt    1740
gatcagttaa gcaaccaggc gtcggttggt ggcataagtt tttccaccaa cgctaacaac    1800
ggccttatgg ttaatgctaa tggttacacc cagcgtctgc cgcagctgtt ccaggcattg    1860
ctcgaggggt actttagcta taccgctacg gaagatcagc ttgagcaggc gaagtcctgg    1920
tataaccaga tgatggattc cgcagaaaag ggtaaagcgt ttgagcaggc gattatgccc    1980
gcgcagatgc tctcgcaagt gccgtacttc tcgcgagatg aacggcgtaa aattttgccc    2040
tccattacgt tgaaagaggt gctggcctat cgcgacgcct aaaatcagg ggctcgacca     2100 gagtttatgg ttatcggcaa catgaccgag gcccaggcaa caacgctggc acgcgatgtg    2160
caaaaacagt gggcgctga tggttcagag tggtgtcgaa acaaagatgt agtggtcgat     2220
aaaaaacaat ccgtcatctt tgaaaaagcc ggtaacagca ccgactccgc actggcagcg    2280
gtatttgtac cgactggcta cgatgaatac accagctcag cctatagctc tctgttgggg    2340
cagatcgtac agccgtggtt ctacaatcag ttgcgtaccg aagaacaatt gggctatgcc    2400
gtgtttgcgt ttccaatgag cgtggggcgt cagtgggca tgggcttcct tttgcaaagc     2460
aatgataaac agccttcatt cttgtgggag cgttacaagg cgttttttccc aaccgcagag    2520 gcaaaattgc gagcgatgaa gccagatgag tttgcgcaaa tccagcaggc ggtaattacc    2580
cagatgctgc aggcaccgca aacgctcggc gaagaagcat cgaagttaag taaagatttc    2640
gatcgcggca atatgcgctt cgattcgcgt gataaaatcg tggcccagat aaaactgctg    2700
acgccgcaaa aacttgctga tttcttccat caggcggtgg tcgagccgca aggcatggct    2760
attctgtcgc agatttccgg cagccagaac gggaaagccg aatatgtaca ccctgaaggc    2820
tggaaagtgt gggagaacgt cagcgcgttg cagcaaacaa tgcccctgat gagtgaaaag    2880
aatgagtga                                                            2889
```

<210> SEQ ID NO 5
<211> LENGTH: 962
<212> TYPE: PRT
<213> ORGANISM: E. coli

<400> SEQUENCE: 5

Met Pro Arg Ser Thr Trp Phe Lys Ala Leu Leu Leu Val Ala Leu
1               5                   10                  15

Trp Ala Pro Leu Ser Gln Ala Glu Thr Gly Trp Gln Pro Ile Gln Glu
            20                  25                  30

Thr Ile Arg Lys Ser Asp Lys Asp Asn Arg Gln Tyr Gln Ala Ile Arg
        35                  40                  45

Leu Asp Asn Gly Met Val Val Leu Leu Val Ser Asp Pro Gln Ala Val
    50                  55                  60

-continued

```
Lys Ser Leu Ser Ala Leu Val Val Pro Val Gly Ser Leu Glu Asp Pro
 65                  70                  75                  80

Glu Ala Tyr Gln Gly Leu Ala His Tyr Leu Glu His Met Ser Leu Met
                 85                  90                  95

Gly Ser Lys Lys Tyr Pro Gln Ala Asp Ser Leu Ala Glu Tyr Leu Lys
            100                 105                 110

Met His Gly Gly Ser His Asn Ala Ser Thr Ala Pro Tyr Arg Thr Ala
        115                 120                 125

Phe Tyr Leu Glu Val Glu Asn Asp Ala Leu Pro Gly Ala Val Asp Arg
    130                 135                 140

Leu Ala Asp Ala Ile Ala Glu Pro Leu Leu Asp Lys Lys Tyr Ala Glu
145                 150                 155                 160

Arg Glu Arg Asn Ala Val Asn Ala Glu Leu Thr Met Ala Arg Thr Arg
                165                 170                 175

Asp Gly Met Arg Met Ala Gln Val Ser Ala Glu Thr Ile Asn Pro Ala
            180                 185                 190

His Pro Gly Ser Lys Phe Ser Gly Gly Asn Leu Glu Thr Leu Ser Asp
        195                 200                 205

Lys Pro Gly Asn Pro Val Gln Gln Ala Leu Lys Asp Phe His Glu Lys
    210                 215                 220

Tyr Tyr Ser Ala Asn Leu Met Lys Ala Val Ile Tyr Ser Asn Lys Pro
225                 230                 235                 240

Leu Pro Glu Leu Ala Lys Met Ala Ala Asp Thr Phe Gly Arg Val Pro
                245                 250                 255

Asn Lys Glu Ser Lys Lys Pro Glu Ile Thr Val Pro Val Val Thr Asp
            260                 265                 270

Ala Gln Lys Gly Ile Ile His Tyr Val Pro Ala Leu Pro Arg Lys
        275                 280                 285

Val Leu Arg Val Glu Phe Arg Ile Asp Asn Asn Ser Ala Lys Phe Arg
    290                 295                 300

Ser Lys Thr Asp Glu Leu Ile Thr Tyr Leu Ile Gly Asn Arg Ser Pro
305                 310                 315                 320

Gly Thr Leu Ser Asp Trp Leu Gln Lys Gln Gly Leu Val Glu Gly Ile
                325                 330                 335

Ser Ala Asn Ser Asp Pro Ile Val Asn Gly Asn Ser Gly Val Leu Ala
            340                 345                 350

Ile Ser Ala Ser Leu Thr Asp Lys Gly Leu Ala Asn Arg Asp Gln Val
        355                 360                 365

Val Ala Ala Ile Phe Ser Tyr Leu Asn Leu Arg Glu Lys Gly Ile
    370                 375                 380

Asp Lys Gln Tyr Phe Asp Glu Leu Ala Asn Val Leu Asp Ile Asp Phe
385                 390                 395                 400

Arg Tyr Pro Ser Ile Thr Arg Asp Met Asp Tyr Val Glu Trp Leu Ala
                405                 410                 415

Asp Thr Met Ile Arg Val Pro Val Glu His Thr Leu Asp Ala Val Asn
            420                 425                 430

Ile Ala Asp Arg Tyr Asp Ala Lys Ala Val Lys Glu Arg Leu Ala Met
        435                 440                 445

Met Thr Pro Gln Asn Ala Arg Ile Trp Tyr Ile Ser Pro Lys Glu Pro
    450                 455                 460

His Asn Lys Thr Ala Tyr Phe Val Asp Ala Pro Tyr Gln Val Asp Lys
465                 470                 475                 480

Ile Ser Ala Gln Thr Phe Ala Asp Trp Gln Lys Lys Ala Ala Asp Ile
```

-continued

```
            485                 490                 495
Ala Leu Ser Leu Pro Glu Leu Asn Pro Tyr Ile Pro Asp Asp Phe Ser
            500                 505                 510

Leu Ile Lys Ser Glu Lys Lys Tyr Asp His Pro Glu Leu Ile Val Asp
            515                 520                 525

Glu Ser Asn Leu Arg Val Val Tyr Ala Pro Ser Arg Tyr Phe Ala Ser
            530                 535                 540

Glu Pro Lys Ala Asp Val Ser Leu Ile Leu Arg Asn Pro Lys Ala Met
545                 550                 555                 560

Asp Ser Ala Arg Asn Gln Val Met Phe Ala Leu Asn Asp Tyr Leu Ala
                565                 570                 575

Gly Leu Ala Leu Asp Gln Leu Ser Asn Gln Ala Ser Val Gly Gly Ile
            580                 585                 590

Ser Phe Ser Thr Asn Ala Asn Asn Gly Leu Met Val Asn Ala Asn Gly
            595                 600                 605

Tyr Thr Gln Arg Leu Pro Gln Leu Phe Gln Ala Leu Leu Glu Gly Tyr
            610                 615                 620

Phe Ser Tyr Thr Ala Thr Glu Asp Gln Leu Glu Gln Ala Lys Ser Trp
625                 630                 635                 640

Tyr Asn Gln Met Met Asp Ser Ala Glu Lys Gly Lys Ala Phe Glu Gln
                645                 650                 655

Ala Ile Met Pro Ala Gln Met Leu Ser Gln Val Pro Tyr Phe Ser Arg
            660                 665                 670

Asp Glu Arg Arg Lys Ile Leu Pro Ser Ile Thr Leu Lys Glu Val Leu
            675                 680                 685

Ala Tyr Arg Asp Ala Leu Lys Ser Gly Ala Arg Pro Glu Phe Met Val
            690                 695                 700

Ile Gly Asn Met Thr Glu Ala Gln Ala Thr Thr Leu Ala Arg Asp Val
705                 710                 715                 720

Gln Lys Gln Leu Gly Ala Asp Gly Ser Glu Trp Cys Arg Asn Lys Asp
                725                 730                 735

Val Val Val Asp Lys Lys Gln Ser Val Ile Phe Glu Lys Ala Gly Asn
            740                 745                 750

Ser Thr Asp Ser Ala Leu Ala Ala Val Phe Val Pro Thr Gly Tyr Asp
            755                 760                 765

Glu Tyr Thr Ser Ser Ala Tyr Ser Ser Leu Leu Gly Gln Ile Val Gln
            770                 775                 780

Pro Trp Phe Tyr Asn Gln Leu Arg Thr Glu Glu Gln Leu Gly Tyr Ala
785                 790                 795                 800

Val Phe Ala Phe Pro Met Ser Val Gly Arg Gln Trp Gly Met Gly Phe
                805                 810                 815

Leu Leu Gln Ser Asn Asp Lys Gln Pro Ser Phe Leu Trp Glu Arg Tyr
            820                 825                 830

Lys Ala Phe Phe Pro Thr Ala Glu Ala Lys Leu Arg Ala Met Lys Pro
            835                 840                 845

Asp Glu Phe Ala Gln Ile Gln Gln Ala Val Ile Thr Gln Met Leu Gln
            850                 855                 860

Ala Pro Gln Thr Leu Gly Glu Glu Ala Ser Lys Leu Ser Lys Asp Phe
865                 870                 875                 880

Asp Arg Gly Asn Met Arg Phe Asp Ser Arg Asp Lys Ile Val Ala Gln
                885                 890                 895

Ile Lys Leu Leu Thr Pro Gln Lys Leu Ala Asp Phe Phe His Gln Ala
            900                 905                 910
```

Val Val Glu Pro Gln Gly Met Ala Ile Leu Ser Gln Ile Ser Gly Ser
             915                 920                 925

Gln Asn Gly Lys Ala Glu Tyr Val His Pro Glu Gly Trp Lys Val Trp
         930                 935                 940

Glu Asn Val Ser Ala Leu Gln Gln Thr Met Pro Leu Met Ser Glu Lys
945                 950                 955                 960

Asn Glu

<210> SEQ ID NO 6
<211> LENGTH: 2915
<212> TYPE: DNA
<213> ORGANISM: E. coli

<400> SEQUENCE: 6

| | | | | | |
|---|---|---|---|---|---|
| attccccgca | gcacctggtt | caaagcatta | ttgttgttag | ttgcccttg | ggcacattaa | 60 |
| tgtcaggcag | aaacgggatg | gcagccgatt | caggaaacca | tccgtaaaag | tgataaagat | 120 |
| aaccgccagt | atcaggctat | acgtctggat | aacggtatgg | tggtcttgct | ggtttctgat | 180 |
| ccgcaggcag | ttaaatcgct | ctcggcgctg | gtggtgcccg | ttgggtcgct | ggaagatccc | 240 |
| gaggcgtacc | aggggctggc | acattacctt | gaacatatga | gtctgatggg | gtcgaaaaag | 300 |
| tacccgcagg | ctgacagtct | ggccgaatat | ctcaaaatgc | acggcggtag | tcacaatgcc | 360 |
| agcactgcgc | cgtatcgcac | ggctttctat | ctggaagttg | agaacgacgc | cttgcctggt | 420 |
| gcggtagacc | gcctggccga | tgctattgct | gaacctttgc | tcgacaagaa | atatgccgaa | 480 |
| cgtgagcgta | atgcggtgaa | cgctgaatta | accatggcgc | gtacgcgtga | cgggatgcgc | 540 |
| atggcacagg | tcagcgcaga | aaccattaac | ccggcacacc | ccggttcaaa | gttttctggt | 600 |
| ggtaaccctcg | aaactttaag | cgacaaacct | ggtaatccgg | tgcagcaggc | gctgaaagat | 660 |
| ttccacgaga | agtactattc | cgccaatttg | atgaaggcgg | ttatttacag | taataaaccg | 720 |
| ctgccggagt | tggcaaaaat | ggcggcggac | acctttggtc | gcgtgccgaa | caaagagagc | 780 |
| aaaaaaccgg | aaatcaccgt | gccggtagtc | accgacgcgc | aaaagggcat | tatcattcat | 840 |
| tacgtccctg | cgctgccgcg | taaagtgttg | cgcgttgagt | ttcgcatcga | taacaactca | 900 |
| gcgaagttcc | gtagtaaaac | cgatgaattg | attacctatc | tgattggcaa | tcgcagccca | 960 |
| ggtacacttt | ctgactggct | gcaaaagcag | ggattagttg | agggcattag | cgccaactcc | 1020 |
| gatcctatcg | tcaacggcaa | cagcggcgta | ttagcgatct | ctgcgtcttt | aaccgataaa | 1080 |
| ggcctggcta | tcgcgatca | ggttgtggcg | gcaattttta | gctatctcaa | tctgttacgt | 1140 |
| gaaaaaggca | ttgataaaca | atacttcgat | gaactggcga | atgtgctgga | tatcgacttc | 1200 |
| cgttatccgt | cgatcacccg | tgatatggat | tacgtcgaat | ggctggcaga | taccatgatt | 1260 |
| cgcgttcctg | ttgagcatac | gctggatgca | gtcaatattg | ccgatcggta | cgatgctaaa | 1320 |
| gcagtaaagg | aacgtctggc | gatgatgacg | ccgcagaatg | cgcgtatctg | gtatatcagc | 1380 |
| ccgaaagagc | cgcacaacaa | aacggcttac | tttgtcgatg | cgccgtatca | ggtcgataaa | 1440 |
| atcagcgcac | aaactttcgc | cgactggcag | aaaaagccg | ccgacattgc | gctctctttg | 1500 |
| ccagagctta | acccttatat | tcctgatgat | ttctcgctga | ttaagtcaga | gaagaaatac | 1560 |
| gaccatccag | agctgattgt | tgatgagtcg | aatctgcgcg | tggtgtatgc | gccaagccgt | 1620 |
| tattttgcca | gcgagcccaa | agctgatgtc | agcctgattt | tgcgtaatcc | gaaagccatg | 1680 |
| gacagcgccc | gcaatcaggt | gatgtttgcg | ctcaatgatt | atctcgcagg | gctggcgctt | 1740 |
| gatcagttaa | gcaaccaggc | gtcggttggt | ggcataagtt | tttccaccaa | cgctaacaac | 1800 |

```
ggccttatgg ttaatgctaa tggttacacc cagcgtctgc cgcagctgtt ccaggcattg    1860 ctcgagggt actttagcta taccgctacg aagatcagc ttgagcaggc gaagtcctgg     1920
tataaccaga tgatggattc cgcagaaaag ggtaaagcgt ttgagcaggc gattatgccc    1980
gcgcagatgc tctcgcaagt gccgtacttc tcgcgagatg aacggcgtaa aattttgccc    2040
tccattacgt tgaaagaggt gctggcctat cgcgacgcct taaaatcagg ggctcgacca    2100
gagtttatgg ttatcggcaa catgaccgag gcccaggcaa caacgctggc acgcgatgtg    2160
caaaaacagt gggcgctga tggttcagag tggtgtcgaa acaaagatgt agtggtcgat     2220
aaaaaacaat ccgtcatctt tgaaaaagcc ggtaacagca ccgactccgc actggcagcg    2280
gtatttgtac cgactggcta cgatgaatac accagctcag cctatagctc tctgttgggg    2340
cagatcgtac agccgtggtt ctacaatcag ttgcgtaccg aagaacaatt gggctatgcc    2400
gtgtttgcgt ttccaatgag cgtggggcgt cagtggggca tgggcttcct tttgcaaagc    2460
aatgataaac agccttcatt cttgtgggag cgttacaagg cgttttttccc aaccgcagag    2520 gcaaaattgc gagcgatgaa gccagatgag tttgcgcaaa tccagcaggc ggtaattacc    2580
cagatgctgc aggcaccgca aacgctcggc gaagaagcat cgaagttaag taaagatttc    2640
gatcgcggca atatgcgctt cgattcgcgt gataaaatcg tggcccagat aaaactgctg    2700
acgccgcaaa aacttgctga tttcttccat caggcggtgg tcgagccgca aggcatggct    2760
attctgtcgc agatttccgg cagccagaac gggaaagccg aatatgtaca ccctgaaggc    2820
tggaaagtgt gggagaacgt cagcgcgttg cagcaaacaa tgcccctgat gagtgaaaag    2880
aatgagtgat gtcgccgaga cactagatcc tttgc                              2915

<210> SEQ ID NO 7
<211> LENGTH: 1425
<212> TYPE: DNA
<213> ORGANISM: E. coli

<400> SEQUENCE: 7
atgaaaaaaa ccacattagc actgagtgca ctggctctga gtttaggttt ggcgttatct      60
ccgctctctg caacggcggc tgagacttct tcagcaacga cagcccagca gatgccaagc     120
cttgcaccga tgctcgaaaa ggtgatgcct tcagtggtca gcattaacgt agaaggtagc     180
acaaccgtta tacgccgcg tatgccgcgt aatttccagc agttcttcgg tgatgattct      240
ccgttctgcc aggaaggttc tccgttccag agctctccgt tctgccaggg tggccagggc     300
ggtaatggtg gcgccagca acagaaattc atggcgctgg gttccggcgt catcattgat      360
gccgataaag gctatgtcgt caccaacaac cacgttgttg ataacgcgac ggtcattaaa     420
gttcaactga gcgatggccg taagttcgac gcgaagatgg ttggcaaaga tccgcgctct     480
gatatcgcgc tgatccaaat ccagaacccg aaaaacctga ccgcaattaa gatggcggat    540
tctgatgcac tgcgcgtggg tgattacacc gtagcgattg gtaacccgtt tggtctgggc    600
gagacggtaa cttccgggat tgtctctgcg ctggggcgta gcggcctgaa tgccgaaaac    660
tacgaaaact tcatccagac cgatgcagcg atcaaccgtg gtaactccgg tggtgcgctg    720
gttaacctga cgcgaact gatcggtatc aacaccgcga tcctcgcacc ggacggcggc     780
aacatcggta tcggttttgc tatcccgagt aacatggtga aaaacctgac ctcgcagatg    840
gtggaatacg gccaggtgaa acgcggtgag ctgggtatta ggggactga gctgaactcc    900 gaactggcga aagcgatgaa agttgacgcc cagcgcggtg ctttcgtaag ccaggttctg    960
```

```
cctaattcct ccgctgcaaa agcgggcatt aaagcgggtg atgtgatcac ctcactgaac    1020
ggtaagccga tcagcagctt tgccgcactg cgtgctcagg tgggtactat gccggtaggc    1080
agcaaactga ccctgggctt actgcgcgac ggtaagcagg ttaacgtgaa cctggaactg    1140
cagcagagca gccagaatca ggttgattcc agctccatct tcaacggcat tgaaggcgct    1200
gagatgagca acaaaggcaa agatcagggc gtggtagtga acaacgtgaa aacgggcact    1260
ccggctgcgc agatcggcct gaagaaaggt gatgtgatta ttggcgcgaa ccagcaggca    1320
gtgaaaaaca tcgctgaact gcgtaaagtt ctcgacagca aaccgtctgt gctggcactc    1380
aacattcagc gcggcgacag caccatctac ctgttaatgc agtaa                    1425
```

<210> SEQ ID NO 8
<211> LENGTH: 474
<212> TYPE: PRT
<213> ORGANISM: E. coli

<400> SEQUENCE: 8

```
Met Lys Lys Thr Thr Leu Ala Leu Ser Ala Leu Ala Leu Ser Leu Gly
1               5                   10                  15

Leu Ala Leu Ser Pro Leu Ser Ala Thr Ala Ala Glu Thr Ser Ser Ala
            20                  25                  30

Thr Thr Ala Gln Gln Met Pro Ser Leu Ala Pro Met Leu Glu Lys Val
        35                  40                  45

Met Pro Ser Val Val Ser Ile Asn Val Glu Gly Ser Thr Thr Val Asn
    50                  55                  60

Thr Pro Arg Met Pro Arg Asn Phe Gln Gln Phe Phe Gly Asp Asp Ser
65                  70                  75                  80

Pro Phe Cys Gln Glu Gly Ser Pro Phe Gln Ser Ser Pro Phe Cys Gln
                85                  90                  95

Gly Gly Gln Gly Gly Asn Gly Gly Gln Gln Lys Phe Met Ala
                100                 105                 110

Leu Gly Ser Gly Val Ile Ile Asp Ala Asp Lys Gly Tyr Val Val Thr
            115                 120                 125

Asn Asn His Val Val Asp Asn Ala Thr Val Ile Lys Val Gln Leu Ser
        130                 135                 140

Asp Gly Arg Lys Phe Asp Ala Lys Met Val Gly Lys Asp Pro Arg Ser
145                 150                 155                 160

Asp Ile Ala Leu Ile Gln Ile Gln Asn Pro Lys Asn Leu Thr Ala Ile
                165                 170                 175

Lys Met Ala Asp Ser Asp Ala Leu Arg Val Gly Asp Tyr Thr Val Ala
            180                 185                 190

Ile Gly Asn Pro Phe Gly Leu Gly Glu Thr Val Thr Ser Gly Ile Val
        195                 200                 205

Ser Ala Leu Gly Arg Ser Gly Leu Asn Ala Glu Asn Tyr Glu Asn Phe
    210                 215                 220

Ile Gln Thr Asp Ala Ala Ile Asn Arg Gly Asn Ser Gly Gly Ala Leu
225                 230                 235                 240

Val Asn Leu Asn Gly Glu Leu Ile Gly Ile Asn Thr Ala Ile Leu Ala
                245                 250                 255

Pro Asp Gly Gly Asn Ile Gly Ile Gly Phe Ala Ile Pro Ser Asn Met
            260                 265                 270

Val Lys Asn Leu Thr Ser Gln Met Val Glu Tyr Gly Gln Val Lys Arg
        275                 280                 285

Gly Glu Leu Gly Ile Met Gly Thr Glu Leu Asn Ser Glu Leu Ala Lys
```

```
                        290                 295                 300
Ala Met Lys Val Asp Ala Gln Arg Gly Ala Phe Val Ser Gln Val Leu
305                 310                 315                 320

Pro Asn Ser Ser Ala Ala Lys Ala Gly Ile Lys Ala Gly Asp Val Ile
                325                 330                 335

Thr Ser Leu Asn Gly Lys Pro Ile Ser Ser Phe Ala Ala Leu Arg Ala
            340                 345                 350

Gln Val Gly Thr Met Pro Val Gly Ser Lys Leu Thr Leu Gly Leu Leu
        355                 360                 365

Arg Asp Gly Lys Gln Val Asn Val Asn Leu Glu Leu Gln Gln Ser Ser
    370                 375                 380

Gln Asn Gln Val Asp Ser Ser Ile Phe Asn Gly Ile Glu Gly Ala
385                 390                 395                 400

Glu Met Ser Asn Lys Gly Lys Asp Gln Gly Val Val Asn Asn Val
                405                 410                 415

Lys Thr Gly Thr Pro Ala Ala Gln Ile Gly Leu Lys Lys Gly Asp Val
            420                 425                 430

Ile Ile Gly Ala Asn Gln Gln Ala Val Lys Asn Ile Ala Glu Leu Arg
        435                 440                 445

Lys Val Leu Asp Ser Lys Pro Ser Val Leu Ala Leu Asn Ile Gln Arg
    450                 455                 460

Gly Asp Ser Thr Ile Tyr Leu Leu Met Gln
465                 470

<210> SEQ ID NO 9
<211> LENGTH: 1425
<212> TYPE: DNA
<213> ORGANISM: E. coli

<400> SEQUENCE: 9
atgaaaaaaa ccacattagc actgagtgca ctggctctga gtttaggttt ggcgttatct      60
ccgctctctg caacggcggc tgagacttct tcagcaacga cagcccagca gatgccaagc     120
cttgcaccga tgctcgaaaa ggtgatgcct tcagtggtca gcattaacgt agaaggtagc     180
acaaccgtta atacgccgcg tatgccgcgt aatttccagc agttcttcgg tgatgattct     240
ccgttctgcc aggaaggttc tccgttccag agctctccgt tctgccaggg tggccagggc     300
ggtaatggtg gcggccagca acagaaattc atggcgctgg ttccggcgt catcattgat      360 gccgataaag ctatgtcgt caccaacaac acgttgttg ataacgcgac ggtcattaaa      420
gttcaactga gcgatggccg taagttcgac gcgaagatgg ttggcaaaga tccgcgctct     480
gatatcgcgc tgatccaaat ccagaacccg aaaaacctga ccgcaattaa gatggcggat     540
tctgatgcac tgcgcgtggg tgattacacc gtagcgattg taacccgtt tggtctgggc     600 gagacggtaa cttccgggat tgtctctgcg ctggggcgta gcggcctgaa tgccgaaaac     660
tacgaaaact tcatccagac cgatgcagcg attaatcgtg taacgccgg tggtgcgctg     720 gttaacctga cggcgaact gatcggtatc aacaccgcga tcctcgcacc ggacggcggc     780
aacatcggta tcggttttgc tatcccgagt aacatggtga aaaacctgac ctcgcagatg     840
gtggaatacg ccaggtgaa acgcggtgag ctggtatta ggggactga gctgaactcc      900 gaactggcga aagcgatgaa agttgacgcc cagcgcggtg cttttcgtaag ccaggttctg     960 cctaattcct ccgctgcaaa agcgggcatt aaagcgggtg atgtgatcac ctcactgaac    1020
ggtaagccga tcagcagctt tgccgcactg cgtgctcagg tgggtactat gccggtaggc    1080
```

```
agcaaactga ccctgggctt actgcgcgac ggtaagcagg ttaacgtgaa cctggaactg    1140
cagcagagca gccagaatca ggttgattcc agctccatct tcaacggcat tgaaggcgct    1200
gagatgagca acaaaggcaa agatcagggc gtggtagtga acaacgtgaa aacgggcact    1260
ccggctgcgc agatcggcct gaagaaaggt gatgtgatta ttggcgcgaa ccagcaggca    1320
gtgaaaaaca tcgctgaact gcgtaaagtt ctcgacagca aaccgtctgt gctggcactc    1380
aacattcagc gcggcgacag caccatctac ctgttaatgc agtaa                   1425

<210> SEQ ID NO 10
<211> LENGTH: 474
<212> TYPE: PRT
<213> ORGANISM: E. coli

<400> SEQUENCE: 10
```

Met Lys Lys Thr Thr Leu Ala Leu Ser Ala Leu Ala Leu Ser Leu Gly
1               5                   10                  15

Leu Ala Leu Ser Pro Leu Ser Ala Thr Ala Ala Glu Thr Ser Ser Ala
            20                  25                  30

Thr Thr Ala Gln Gln Met Pro Ser Leu Ala Pro Met Leu Glu Lys Val
        35                  40                  45

Met Pro Ser Val Val Ser Ile Asn Val Glu Gly Ser Thr Thr Val Asn
    50                  55                  60

Thr Pro Arg Met Pro Arg Asn Phe Gln Gln Phe Phe Gly Asp Asp Ser
65                  70                  75                  80

Pro Phe Cys Gln Glu Gly Ser Pro Phe Gln Ser Ser Pro Phe Cys Gln
                85                  90                  95

Gly Gly Gln Gly Gly Asn Gly Gly Gln Gln Gln Lys Phe Met Ala
            100                 105                 110

Leu Gly Ser Gly Val Ile Ile Asp Ala Asp Lys Gly Tyr Val Val Thr
        115                 120                 125

Asn Asn His Val Val Asp Asn Ala Thr Val Ile Lys Val Gln Leu Ser
    130                 135                 140

Asp Gly Arg Lys Phe Asp Ala Lys Met Val Gly Lys Asp Pro Arg Ser
145                 150                 155                 160

Asp Ile Ala Leu Ile Gln Ile Gln Asn Pro Lys Asn Leu Thr Ala Ile
                165                 170                 175

Lys Met Ala Asp Ser Asp Ala Leu Arg Val Gly Asp Tyr Thr Val Ala
            180                 185                 190

Ile Gly Asn Pro Phe Gly Leu Gly Glu Thr Val Thr Ser Gly Ile Val
        195                 200                 205

Ser Ala Leu Gly Arg Ser Gly Leu Asn Ala Glu Asn Tyr Glu Asn Phe
    210                 215                 220

Ile Gln Thr Asp Ala Ala Ile Asn Arg Gly Asn Ala Gly Gly Ala Leu
225                 230                 235                 240

Val Asn Leu Asn Gly Glu Leu Ile Gly Ile Asn Thr Ala Ile Leu Ala
                245                 250                 255

Pro Asp Gly Gly Asn Ile Gly Ile Gly Phe Ala Ile Pro Ser Asn Met
            260                 265                 270

Val Lys Asn Leu Thr Ser Gln Met Val Glu Tyr Gly Gln Val Lys Arg
        275                 280                 285

Gly Glu Leu Gly Ile Met Gly Thr Glu Leu Asn Ser Glu Leu Ala Lys
    290                 295                 300

Ala Met Lys Val Asp Ala Gln Arg Gly Ala Phe Val Ser Gln Val Leu
305                 310                 315                 320

```
Pro Asn Ser Ser Ala Ala Lys Ala Gly Ile Lys Ala Gly Asp Val Ile
                325                 330                 335

Thr Ser Leu Asn Gly Lys Pro Ile Ser Ser Phe Ala Ala Leu Arg Ala
            340                 345                 350

Gln Val Gly Thr Met Pro Val Gly Ser Lys Leu Thr Leu Gly Leu Leu
        355                 360                 365

Arg Asp Gly Lys Gln Val Asn Val Asn Leu Glu Leu Gln Gln Ser Ser
370                 375                 380

Gln Asn Gln Val Asp Ser Ser Ile Phe Asn Gly Ile Glu Gly Ala
385                 390                 395                 400

Glu Met Ser Asn Lys Gly Lys Asp Gln Gly Val Val Val Asn Asn Val
                405                 410                 415

Lys Thr Gly Thr Pro Ala Ala Gln Ile Gly Leu Lys Lys Gly Asp Val
            420                 425                 430

Ile Ile Gly Ala Asn Gln Gln Ala Val Lys Asn Ile Ala Glu Leu Arg
        435                 440                 445

Lys Val Leu Asp Ser Lys Pro Ser Val Leu Ala Leu Asn Ile Gln Arg
            450                 455                 460

Gly Asp Ser Thr Ile Tyr Leu Leu Met Gln
465                 470

<210> SEQ ID NO 11
<211> LENGTH: 107
<212> TYPE: PRT
<213> ORGANISM: Artificial Sequence
<220> FEATURE:
<223> OTHER INFORMATION: hTNF40-gL1

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105

<210> SEQ ID NO 12
<211> LENGTH: 118
<212> TYPE: PRT
<213> ORGANISM: Artificial Sequence
<220> FEATURE:
<223> OTHER INFORMATION: gh3h TNF40.4

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
```

```
                    35                  40                  45
Gly Trp Ile Asn Thr Tyr Ile Gly Glu Pro Ile Tyr Ala Asp Ser Val
 50                  55                  60

Lys Gly Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Arg Ser Tyr Ala Met Asp Tyr Trp Gly Gln Gly Thr
            100                 105                 110

Leu Val Thr Val Ser Ser
            115

<210> SEQ ID NO 13
<211> LENGTH: 214
<212> TYPE: PRT
<213> ORGANISM: Artificial Sequence
<220> FEATURE:
<223> OTHER INFORMATION: Grafted Light Chain

<400> SEQUENCE: 13

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Gly Thr Asn
             20                  25                  30

Val Ala Trp Tyr Gln Gln Lys Pro Gly Lys Ala Pro Lys Ala Leu Ile
         35                  40                  45

Tyr Ser Ala Ser Phe Leu Tyr Ser Gly Val Pro Tyr Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ile Tyr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 229
<212> TYPE: PRT
<213> ORGANISM: Artificial Sequence
<220> FEATURE:
<223> OTHER INFORMATION: Grafted Heavy Chain

<400> SEQUENCE: 14
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Ala Ala
225

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 15
gcatcataat tttcttttta cctc                                          24

<210> SEQ ID NO 16
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 16
gggaaatgaa cctgagcaaa acgc                                          24

<210> SEQ ID NO 17
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 17
```

```
gtgccaggag atgcagcagc ttgc                                          24

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 18
tttgcagcca gtcagaaagt g                                             21

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 19
ctgcctgcga ttttcgccgg aacg                                          24

<210> SEQ ID NO 20
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 20
cgcatggtac gtgccacgat atcc                                          24

<210> SEQ ID NO 21
<211> LENGTH: 66
<212> TYPE: DNA
<213> ORGANISM: Escherichia coli
<220> FEATURE:
<221> NAME/KEY: exon
<222> LOCATION: (4)..(66)

<400> SEQUENCE: 21 tga atg ccc cgc agc acc tgg ttc aaa gca tta ttg ttg tta gtt gcc    48
    Met Pro Arg Ser Thr Trp Phe Lys Ala Leu Leu Leu Leu Val Ala
    1               5                   10                  15 ctt tgg gca ccc tta agt                                             66
Leu Trp Ala Pro Leu Ser
            20

<210> SEQ ID NO 22
<211> LENGTH: 66
<212> TYPE: DNA
<213> ORGANISM: Escherichia coli
<220> FEATURE:
<221> NAME/KEY: exon
<222> LOCATION: (4)..(60)
<220> FEATURE:
<221> NAME/KEY: exon
<222> LOCATION: (64)..(66)

<400> SEQUENCE: 22 tga att ccc cgc agc acc tgg ttc aaa gca tta ttg ttg tta gtt gcc    48
    Ile Pro Arg Ser Thr Trp Phe Lys Ala Leu Leu Leu Leu Val Ala
    1               5                   10                  15 ctt tgg gca cat taa tgt                                             66
Leu Trp Ala His     Cys
                20
```

```
<210> SEQ ID NO 23
<211> LENGTH: 66
<212> TYPE: DNA
<213> ORGANISM: Escherichia coli
<220> FEATURE:
<221> NAME/KEY: exon
<222> LOCATION: (1)..(66)

<400> SEQUENCE: 23 atg aac atg ttt ttt agg ctt acc gcg tta gct ggc ctg ctt gca ata       48
Met Asn Met Phe Phe Arg Leu Thr Ala Leu Ala Gly Leu Leu Ala Ile
1               5                   10                  15 gca ggc cag acc ttc gct                                               66
Ala Gly Gln Thr Phe Ala
            20

<210> SEQ ID NO 24
<211> LENGTH: 66
<212> TYPE: DNA
<213> ORGANISM: Escherichia coli
<220> FEATURE:
<221> NAME/KEY: exon
<222> LOCATION: (1)..(27)
<220> FEATURE:
<221> NAME/KEY: exon
<222> LOCATION: (31)..(45)
<220> FEATURE:
<221> NAME/KEY: exon
<222> LOCATION: (49)..(60)
<220> FEATURE:
<221> NAME/KEY: exon
<222> LOCATION: (64)..(66)

<400> SEQUENCE: 24 atg aat tcg ttt tta ggc tta ccg cgt tag ctg gcc tgc ttg caa tag       48
    Met Asn Ser Phe Leu Gly Leu Pro Arg     Leu Ala Cys Leu Gln
    1               5                           10 cag gcc aga cat taa ttg                                               66
Gln Ala Arg His     Leu
15

<210> SEQ ID NO 25
<211> LENGTH: 33
<212> TYPE: DNA
<213> ORGANISM: Escherichia coli
<220> FEATURE:
<221> NAME/KEY: exon
<222> LOCATION: (1)..(33)

<400> SEQUENCE: 25 gat gca gcg atc aac cgt ggt aac tcc ggt ggt                           33
Asp Ala Ala Ile Asn Arg Gly Asn Ser Gly Gly
1               5                   10

<210> SEQ ID NO 26
<211> LENGTH: 33
<212> TYPE: DNA
<213> ORGANISM: Escherichia coli
<220> FEATURE:
<221> NAME/KEY: exon
<222> LOCATION: (1)..(33)

<400> SEQUENCE: 26 gat gca gcg att aat cgt ggt aac gcc ggt ggt                           33
Asp Ala Ala Ile Asn Arg Gly Asn Ala Gly Gly
1               5                   10
```